United States Patent [19]

Thorpe et al.

[11] Patent Number: 5,660,827
[45] Date of Patent: Aug. 26, 1997

[54] ANTIBODIES THAT BIND TO ENDOGLIN

[75] Inventors: Philip E. Thorpe, Dallas, Tex.; Francis J. Burrows, San Diego, Calif.

[73] Assignee: Board of Regents, The University of Texas System, Austin, Tex.

[21] Appl. No.: 457,229

[22] Filed: Jun. 1, 1995

Related U.S. Application Data

[60] Division of Ser. No. 350,212, Dec. 5, 1994, which is a continuation-in-part of Ser. No. 205,330, Mar. 2, 1994, which is a continuation-in-part of Ser. No. 295,868, Sep. 6, 1994, which is a continuation-in-part of Ser. No. 846,349, Mar. 5, 1992, abandoned.

[51] Int. Cl.$^6$ ......................... A61K 39/395; C07K 16/00
[52] U.S. Cl. ..................... 424/152.1; 424/141.1; 424/130.1; 424/138.1; 530/387.1; 530/388.1
[58] Field of Search ........................ 530/387.1, 388.1, 530/388.85; 424/130.1, 138.1, 141.1, 152.1

[56] References Cited

U.S. PATENT DOCUMENTS

| | | |
|---|---|---|
| 4,456,550 | 6/1984 | Dvorak et al. |
| 4,472,509 | 9/1984 | Gansow et al. |
| 5,021,236 | 6/1991 | Gries et al. |
| 5,081,034 | 1/1992 | Bevilacqua et al. |

FOREIGN PATENT DOCUMENTS

| | | | |
|---|---|---|---|
| WO81/01145 | 4/1981 | WIPO | C07C 103/52 |
| WO90/13300 | 11/1990 | WIPO | |
| WO90/12585 | 11/1990 | WIPO | |
| WO92/12729 | 8/1992 | WIPO | |
| WO92/19646 | 11/1992 | WIPO | |
| WO93/08210 | 4/1993 | WIPO | |
| WO93/08473 | 4/1993 | WIPO | |
| WO93/17715 | 9/1993 | WIPO | A61K 47/48 |
| WO94/05328 | 3/1994 | WIPO | A61K 39/395 |
| WO94/11499 | 5/1994 | WIPO | |
| WO94/10202 | 5/1994 | WIPO | |

OTHER PUBLICATIONS

Burrows et al., "A Murine Model for Antibody-Directed Targeting of Vascular Endothelial Cells in Solid Tumors," *Cancer Research*, 52:5954–5962, Nov. 1992.

Burrows and Thorpe, "Targeting the Vasculature of Solid Tumors," *Journal of Controlled Release*, 28:195–202, Jan. 1994.

Clauss et al., "A Polypeptide Factor Produced by Fibrosarcoma Cells That Induces Endothelial Tissue Factor and Enhances the Procoagulant Response to Tumor Necrosis Factor/Cachetin," *The Journal of Biological Chemistry*, 265(12):7078–7083, Apr. 1990.

Thorpe and Burrows, "Antibody-Directed Targeting of the Vasculature of Solid Tumors," *Breast Cancer Research and Treatment*, 36(2):237–251, 1995.

Yamazaki et al., "Bispecific Monoclonal Antibodies with Specificities for Activated Platelets and Thrombolytic Agents, Their Production and Use," Abstract for Canadian Patent Application CA 2039259; Chem Abstracts, 117(11), Abstract #109988.

Osborn et al., "Leukocyte Adhesion to Endothelium in Inflammation," *Cell*, 62:3–6, 1990.

June et al., "Role of the CD28 Receptor in T–Cell Activation," *Immunology Today*, 11(6):211–216, 1990.

Denekamp, "Vascular Attack as a Therapeutic Strategy for Cancer," *Cancer and Metastasis Reviews*, 9:267–282, 1990.

Scott et al., "Anti–CD3 Antibody Induces Rapid Expression of Cytokine Genes In Vivo," *The Journal of Immunology*, 145(7):2183–2188, 1990.

O'Connell & Edidin, "A Mouse Lymphoid Endothelial Cell Line Immortalized by Simian Virus 40 Binds Lymphocytes and Retains Functional Characteristics of Normal Endothelial Cells," *The Journal of Immunology*, 144(2):521–525, 1990.

Ledbetter et al., "CD 28 Ligation in T–Cell Activation: Evidence for Two Signal Transduction," Abstract only, *Blood*, 75(7):1531–1539, 1990.

Watanabe et al., "Exogenous Expression of Mouse Interferon γ cDNA in Mouse Neuroblastoma C1300 Cells Results in Reduced Tumorigenicity by Augmented Anti–Tumor Immunity," *Proceedings of the National Academy of Scientists*, 86:9456–9460, 1989.

Schütt et al., "Human Monocyte Activation Induced by an Anti–CD14 Monoclonal Antibody," *Immunology Letters*, 19:321–328, 1988.

Thorpe et al., "Improved Antitumor Effects of Immunotoxins Prepared with Deglycosylated Ricin A–Chain and Hindered Disulfide Linkages," *Cancer Research*, 48:6396–6403, 1988.

Glennie et al., "Preparation and Performance of Bispecific (F(ab'γ)$_2$ Antibody Containing Thioether–Linked Fab'γ Fragments," *The Journal of Immunology*, 139(7):2367–2375, 1987.

Bevilacqua, et al., "Identification of an Inducible Endothelial–Leukocyte Adhesion Molecule," *Proceedings of the National Academy of Scientists*, 84:9238–9242, 1987.

Cotran et al., "Induction and Detection of a Human Endothelial Activation Antigen In Vivo," Abstract only, *The Journal of Experimental Medicine*, 164(2):661–666, 1986.

Groenewegen et al., "Lymphokine Dependence of In Vivo Expression of MHC Class II Antigens by Endothelium," *Nature*, 316:361–263, 1985.

Moretta et al., Abstract only, *The Journal of Experimental Medicine*, 162(3):823–838, 1985.

(List continued on next page.)

*Primary Examiner*—Lila Feisee
*Assistant Examiner*—Ray F. Ebert
*Attorney, Agent, or Firm*—Arnold, White & Durkee

[57] ABSTRACT

Disclosed are antibodies that specifically bind to endoglin. Conjugates of the antibodies linked to diagnostic or therapeutic agents are also provided. Methods of using the antibodies and conjugates are also disclosed, including methods of targeting the vasculature of solid tumors through recognition of the tumor vasculature-associated antigen, endoglin.

30 Claims, 25 Drawing Sheets

OTHER PUBLICATIONS

Vaickus & Foon, "Overview of Monoclonal Antibodies in the Diagnosis and Therapy of Cancer," *Cancer Investigation*, 93(2):295–209, 1991.

Hagemeier et al., "A Monoclonal Antibody Reacting with Endothelial Cells of Budding Vessels in Tumors and Inflammatory Tissues, and Non–Reactive with Normal Adult Tissues," *International Journal of Cancer*, 38:481–488, 1986.

Duijvestijn et al., "Lymphoid Tissue–and Inflammation–Specific Endothelial Cell Differentiation defined by Monoclonal Antibodies," *The Journal of Immunology*, 138(3):713–719, 1987.

Murray et al., "Vascular Markers for Murine Tumours," *Radiotherapy and Oncology*, 16:221–234, 1989.

Schlingemann et al., "Monoclonal Antibody PAL–E Specific for Endothelium," *Laboratory Investigation*, 52(1):71–76, 1985.

Bruland et al., "New Monoclonal Antibodies Specific for Human Sarcomas," *International Journal of Cancer*, 38:27–31, 1986.

Reisfeld et al., "Human Tumor–Associated Antigens Defined by Monoclonal Antibodies," *CRC Critical Reviews in Immunology*, 5(1):27–53, 1984.

Schlom et al., "Monoclonal Antibodies Reactive with Breast Tumor–Associated Antigens," *Advances in Cancer Research*, 43:143–173, 1985.

Kaplan, "The Diagnostic and Therapeutic Use of Monoclonal Antibodies in Colorectal Cancer," *Hematology/Oncology Clinics of North American*, 3(1):125–134, 1989.

Smith & Teng, "Clinical Applications of Monoclonal Antibodies in Gynecologic Oncology," *Cancer*, 60:2068–2074, 1987.

Stavrou, "Monoclonal Antibodies in Neuro–Oncology," *Neurosurgery Review*, 13:7–18, 1990.

Shepard et al., "Monoclonal Antibody Therapy of Human Cancer: Taking the HEr2 Protooncogene to the Clinic," *Journal of Clinical Immunology*, 11(3):117–127, 1991.

Szymendera, "Clinical Usefulness of Three Monoclonal Antibody–Defined Tumor Markers: CA 19–9, CA 50, and CA 125," *Tumour Biology*, 7:333–342, 1986.

Catane & Longo, "Monoclonal Antibodies for Cancer Therapy," *Israel Jorunal of Medical Sciences*, 24:471–476, 1988.

Greiner et al., "Applications of Monoclonal Antibodies and Recombinant Cytokines for the Treatment of Human Colorectal and Other Carcinomas," *Journal of Surgical Oncology Supplement*, 2:9–13, 1991.

Thor & Edgerton, "Monoclonal Antibodies Reactive with Human Breast or Ovarian Carcinoma: In Vivo Applications," *Seminars in Nuclear Medicine*, 19(4):295–308, 1989.

Thorpe et al., "Selective Killing of Proliferating Vascular Endothelial Cells by an Anti–Fibronectin Receptor Immunotoxin," *16th LH Gray Conference*, University of Manchester Institute of Science and Technology, Sep. 17–21, 1990.

Thorpe et al., "Targeting To Proliferating Vascular Endothelium," *International Symposium on Angiogenesis*, St. Gallen, Switzerland, Abstract, Mar. 13–15, 1991.

Ghose, Tarun I. et al., "Preparation of Antibody–Linked Cytotoxic Agents," *Methods in Enzymology*, 93:280–333, 1983.

Knowles, Phillip P. and Thorpe, Philip E., "Purification of Immunotoxins Containing Ricin A–Chain and Abrin–A–Chain Using Blue Sepharose CL–6B," *Analytical Biochemistry*, 160:440–443, 1987.

Wang, Theodore S.T. et al., "Photoreactive In–Cyclodextrin Inclusion Complex: a New Heterobifunctional Reagent for Antibody Labeling," *Nuclear Medicine and Biology*, 19(8):897–902, 1992.

PCT Search Report mailed Jun. 25, 1993.

Alvarez, J.A. et al., "Localization of Basic Fibroblast Growth Factor and Vascular Endothelial Growth Factor in Human Glial Neoplasms," *Modern Pathology*, 5(3):303–307, 1992.

Brown, Lawrence F. et al., "Expression of Vascular Permeability Factor (Vascular Endothelial Growth Factor) and Its Receptors in Adenocarcinomas of the Gastrointestinal Tract," *Cancer Research*, 53:4727–4735, 1993.

Kim, K. Jin et al., "Inhibition of vascular endothelial growth factor–induced angiogenesis suppresses tumor growth in vivo," *Nature*, 362:841–843, 1993.

Dvorak, Harold F. et al., "Distribution of Vascular Permeability Factor (Vascular Endothelial Growth Factor) in Tumors: Concentration in Tumor Blood Vessels," *J. Exp. Med.*, 174:1275–1278, 1991.

Gerlach, Herwig et al., "Enhanced Responsiveness of Endothelium in the Growing/Motile State to Tumor Necrosis Factor/Cachetin," *J. Exp. Med.*, 170:913–931, 1989.

Gougos, Anne et al., "Identification of distinct epitopes of endoglin, an RGD–containing glycoprotein of endothelial cells, leukemic cells, and synctiotrophoblasts," *International Immunology*, 4(1):83–92, 1991.

Gougos, Anne et al., "Identification of a Human Endothelial Cell Antigen with Monoclonal Antibody 44G4 Produced Against a Pre–B Leukemic Cell Line," *The Journal of Immunology*, 141:1925–1933, 1988.

Gougos, Anne et al., "Biochemical Characterization of the 44G4 Antigen from the Hoon Pre–B Leukemic Cell Line," *The Journal of Immunology*, 141:1934–1940, 1988.

Jakeman, Lyn B. et al., "Binding Sites for Vascular Endothelial Growth Factor Are Localized on Endothelial Cells in Adult Rat Tissues," *J. Clin. Invest.*, 89:244–253, 1992.

Nabel, Elizabeth G. et al., "Recombinant fibroblast growth factor–1 promotes intimal hyperplasia and angiogenesis in arteries in vivo," *Nature*, 362:844, 1993.

O'Connell, P.J. et al., "Endoglin: a 180–kD endothelial cell and macrophage restricted differentiation molecule," *Clin. Exp. Immunol.*, 90:154–159, 1992.

Plate, K.H. et al., "Up–Regulation of Vascular Endothelial Growth Factor and Its Cognate Receptors in a Rat Glioma Model of Tumor Angiogenesis," *Cancer Research*, 53(23):5822–5827, 1993.

Plate, Karl H. et al., "Vascular endothelial growth factor is a potential tumour angiogenesis factor in human gliomas in vivo," *Nature*, 359:845–848, 1992.

Rettig, Wolfgang J. et al., "Identification of endosialin, a cell surface glycoprotein of vascular endothelial cells in human cancer," *Proc. Natl. Acad. Sci. USA*, 89:10832–10836, 1992.

Sarma, Vidya et al., "Cloning of a Novel Tumor Necrosis Factor–α–Inducible Primary Response Gene that is Differentially Expressed in Development and Capillary Tube–Like Formation in vitro," *The Journal of Immunology*, 148:3302–3312, 1992.

Senger, Donald R. et al., "Vascular permeability factor (VPF, VEGF) in tumor biology," *Cancer and Metatasts Reviews*, 12:303–324, 1993.

Shweiki, Dorit et al., "Vascular endothelial growth factor induced by hypoxia may mediate hypoxia–initiated angiogenesis," *Nature*, 359:843–845, 1992.

Wang, J.M. et al., "A Monoclonal Antibody Detects Heterogeneity in Vascular Endothelium of Tumours and Normal Tissues," *Int. J. Cancer*, 54:363–370, 1993.

Westphal, Johan R. et al., "A New 180–kDa Dermal Endothelial Cell Activation Antigen: In Vitro and In Situ Characteristics," *The Journal of Investigative Dermatology*, 100(1):27–34, 1993.

Yeo, Kiang–Teck et al., "Vascular Permeability Factor (Vascular Endothelial Growth Factor) in Guinea Pig and Human Tumor and Inflammatory Effusions," *Cancer Research*, 53:2912–2918, 1993.

Büring et al., "Endoglin is expressed on a subpopulation of immature erythroid cells of normal human bone marrow," *Leukemia*, 5(10):841–847, 1991.

Dvorak et al., "Structure of Solid Tumors and Their Vasclature: Implications for Therapy with Monoclonal Antibodies," *Cancer Cells*, 3(3):77–85, 1991.

Gougos & Letarte, "Primary Structure of Endoglin, an RGD–containing Glycoprotein of Human Endothelial Cells," *The Journal of Biological Chemistry*, 265(15):8361–8364, 1990.

UTSD:344; U.S. Serial No. 08/295,868, Nationalization of PCT/US/01956; U.S. Filing date Sep. 6, 1994.

UTSD:393; U.S. Serial No. 08/205,330; filed Mar. 2, 1994.

UTSD:430; U.S. Serial No. 08/350,212; filed Dec. 5, 1994.

UTSD:451; U.S. Serial No. 08/456,495, filed Jun. 1, 1995; Divisional of UTSD:430.

UTSD:452; U.S. Serial No. 08/457,487, filed Jun. 1, 1995; Divisional of UTSD:430.

UTSD:454; U.S. Serial No. 08/457,031, filed Jun. 1, 1995; Divisional of UTSD:430.

UTSD:455; U.S. Serial No. 08/457,869, filed Jun. 1, 1995; Divisional of UTSD:430.

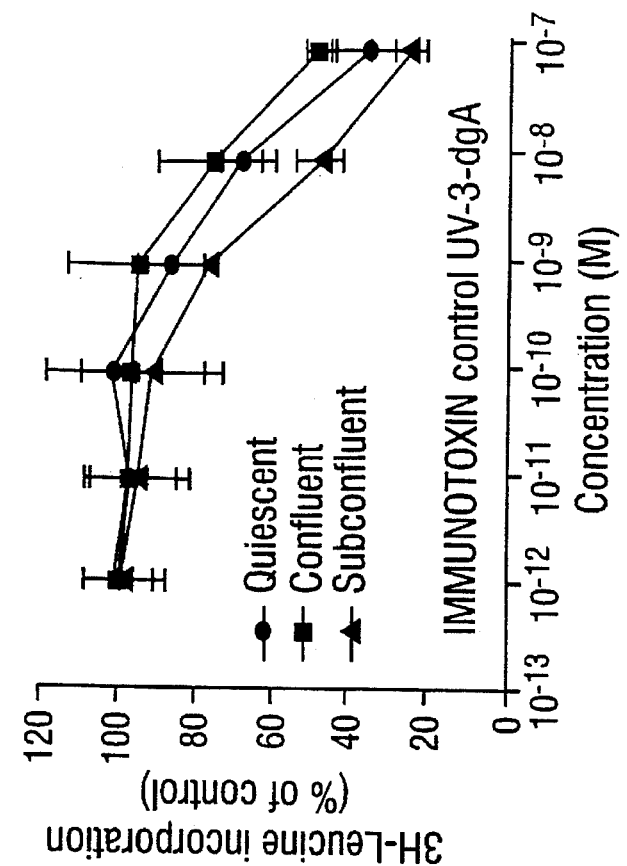
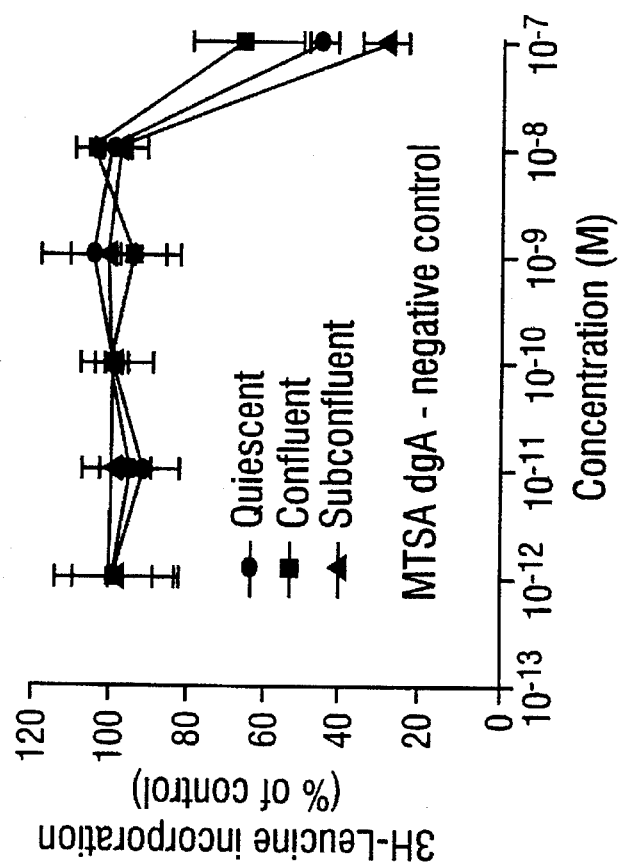

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Ala Pro Met Ala Glu Gly Glu Gln Lys Pro Arg Glu Val Val Lys Phe
 1               5                  10                 15
Met Asp Val Tyr Lys Arg Ser Tyr Cys
             20                  25
```

( 2 ) INFORMATION FOR SEQ ID NO:2:

( i ) SEQUENCE CHARACTERISTICS:
      ( A ) LENGTH: 26 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

```
Ala Pro Met Ala Glu Gly Gly Gly Gln Asn His His Glu Val Val Lys
 1               5                  10                 15
Phe Met Asp Val Tyr Gln Arg Ser Tyr Cys
                 20                  25
```

( 2 ) INFORMATION FOR SEQ ID NO:3:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

```
Met Ala Ala Gly Ser Ile Thr Thr Leu Pro Ala Leu Pro Glu Gly Gly
 1               5                  10                 15
Asp Gly Gly Ala Phe Ala Pro Gly Cys
             20                  25
```

ANTIBODIES THAT BIND TO ENDOGLIN

The present application is a Divisional of U.S. Ser. No. 08/350,212, filed Dec. 5, 1994; which is a continuation-in-part of U.S. Ser. No. 08/205,330, filed Mar. 2, 1994; which is a continuation-in-part of U.S. Ser. No. 08/295,868, filed Sep. 6, 1994 (nationalized from PCT US93/01956, filed Mar. 5, 1993); which is a continuation-in-part of U.S. Ser. No. 07/846,349, filed Mar. 5, 1992, now abandoned.

The U.S. government owns rights in the present invention pursuant to NIH Grant CA-28149 and NIH Grant CA54168.

BACKGROUND OF THE INVENTION

1. Field of the Invention

The present invention relates generally to methods and compositions for targeting the vasculature of solid tumors using immunological and growth factor-based reagents. In particular aspects, antibodies carrying diagnostic or therapeutic agents are targeted to the vasculature of solid tumor masses through recognition of tumor vasculature-associated antigens, such as endoglin, or through the specific induction of other antigens on vascular endothelial cells in solid tumors.

2. Description of Related Art

Over the past 30 years, fundamental advances in the chemotherapy of neoplastic disease have been realized. While some progress has been made in the development of new chemotherapeutic agents, the more startling achievements have been made in the development of effective regimens for concurrent administration of drugs, and our knowledge of the basic science, e.g., the underlying neoplastic processes at the cellular and tissue level, and the mechanism of action of basic antineoplastic agents. As a result of the fundamental achievement, we can point to significant advances in the chemotherapy of a number of neoplastic diseases, including choriocarcinoma, Wilm's tumor, acute leukemia, rhabdomyosarcoma, retinoblastoma, Hodgkin's disease and Burkitt's lymphoma, to name just a few. Despite the impressive advances that have been made in a few tumors, though, many of the most prevalent forms of human cancer still resist effective chemotherapeutic intervention.

The most significant underlying problem that must be addressed in any treatment regimen is the concept of "total cell kill." This concept holds that in order to have an effective treatment regimen, whether it be a surgical or chemotherapeutic approach or both, there must be a total cell kill of all so-called "clonogenic" malignant cells, that is, cells that have the ability to grow uncontrolled and replace any tumor mass that might be removed. Due to the ultimate need to develop therapeutic agents and regimens that will achieve a total cell kill, certain types of tumors have been more amenable than others to therapy. For example, the soft tissue tumors (e.g., lymphomas), and tumors of the blood and blood-forming organs (e.g., leukemias) have generally been more responsive to chemotherapeutic therapy than have solid tumors such as carcinomas. One reason for this is the greater physical accessibility of lymphoma and leukemic cells to chemotherapeutic intervention. Simply put, it is much more difficult for most chemotherapeutic agents to reach all of the cells of a solid tumor mass than it is the soft tumors and blood-based tumors, and therefore much more difficult to achieve a total cell kill. The toxicities associated with most conventional antitumor agents then become a limiting factor.

A key to the development of successful antitumor agents is the ability to design agents that will selectively kill tumor cells, while exerting relatively little, if any, untoward effects against normal tissues. This goal has been elusive to achieve, though, in that there are few qualitative differences between neoplastic and normal tissues. Because of this, much research over the years has focused on identifying tumor-specific "marker antigens" that can serve as immunological targets both for chemotherapy and diagnosis. Many tumor-specific, or quasi-tumor-specific ("tumor-associated"), markers have been identified as tumor cell antigens that can be recognized by specific antibodies. Unfortunately, it is generally the case that tumor specific antibodies will not in and of themselves exert sufficient antitumor effects to make them useful in cancer therapy.

Over the past fifteen years, immunotoxins have shown great promise as a means of selectively targeting cancer cells. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. Although early immunotoxins suffered from a variety of drawbacks, more recently, stable, long-lived immunotoxins have been developed for the treatment of a variety of malignant diseases. These "second generation" immunotoxins employ deglycosylated ricin A chain to prevent entrapment of the immunotoxin by the liver and hepatotoxicity (Blakey et al., 1987). They employ new crosslinkers which endow the immunotoxins with high in vivo stability (Thorpe et al., 1988) and they employ antibodies which have been selected using a rapid indirect screening assay for their ability to form highly potent immunotoxins (Till et al., 1988).

Immunotoxins have proven highly effective at treating lymphomas and leukemias in mice (Thorpe et al., 1988; Ghetie et al., 1991; Griffin et al., 1988) and in man (Vitetta et al., 1991). Lymphoid neoplasias are particularly amenable to immunotoxin therapy because the tumor cells are relatively accessible to blood-borne immunotoxins; also, it is possible to target normal lymphoid antigens because the normal lymphocytes which are killed along with the malignant cells during therapy are rapidly regenerated from progenitors lacking the target antigens. In Phase I trials where patients had large bulky tumor masses, greater than 50% tumor regressions were achieved in approximately 40% of the patients (Vitetta et al., 1991). It is predicted that the efficacy of these immunotoxins in patients with less bulky disease will be even better.

In contrast with their efficacy in lymphomas, immunotoxins have proved relatively ineffective in the treatment of solid tumors such as carcinomas (Weiner et al., 1989; Byers et al., 1989). The principal reason for this is that solid tumors are generally impermeable to antibody-sized molecules: specific uptake values of less than 0.001% of the injected dose/g of tumor are not uncommon in human studies (Sands et al., 1988; Epenetos et al., 1986). Furthermore, antibodies that enter the tumor mass do not distribute evenly for several reasons. Firstly, the dense packing of tumor cells and fibrous tumor stromas present a formidable physical barrier to macromolecular transport and, combined with the absence of lymphatic drainage, create an elevated interstitial pressure in the tumor core which reduces extravasation and fluid convection (Baxter et al., 1991; Jain, 1990). Secondly, the distribution of blood vessels in most tumors is disorganized and heterogeneous, so some tumor cells are separated from extravasating antibody by large diffusion distances (Jain, 1990). Thirdly, all of the antibody entering the tumor may become adsorbed in perivascular regions by the first tumor cells encountered, leaving none to reach tumor cells at more distant sites (Baxter et al., 1991; Kennel et al., 1991). Finally, antigen-deficient mutants can escape being killed by the immunotoxin and regrow (Thorpe et al., 1988).

Thus, it is quite clear that a significant need exists for the development of novel strategies for the treatment of solid tumors. One approach would be to target cytotoxic agents or coagulants to the vasculature of the tumor rather than to the tumor. Indeed, it has been observed that many existing therapies may already have, as part of their action, a vascular-mediated mechanism of action (Denekamp, 1990). The present inventors propose that this approach offers several advantages over direct targeting of tumor cells. Firstly, the target cells are directly accessible to intravenously administered therapeutic agents, permitting rapid localization of a high percentage of the injected dose (Kennel et al., 1991). Secondly, since each capillary provides oxygen and nutrients for thousands of cells in its surrounding 'cord' of tumor, even limited damage to the tumor vasculature could produce an avalanche of tumor cell death (Denekamp, 1990; Denekamp, 1984). Finally, the outgrowth of mutant endothelial cells lacking the target antigen is unlikely because they are normal cells.

For tumor vascular targeting to succeed, antibodies are required that recognize tumor endothelial cells but not those in normal tissues. Although several antibodies have been raised (Duijvestijn et al., 1987; Hagemeier et al., 1986; Bruland et al., 1986; Murray et al., 1989; Schlingemann et al., 1985) none has shown a high degree of specificity.

The antibodies termed TP-1 and TP-3, which were raised against human osteosarcoma cells, have been reported to react with the same antigen present on proliferating osteoblasts in normal degenerating bone tissue. They also cross-react with capillary buds in a number of tumor types and in placenta, but apparently not with capillaries in any of the normal adult tissues examined (Bruland et al., 1986). It remains to be seen whether the TP-1/TP-3 antigen is present on the surface of endothelial cells or whether the antibodies cross-react with gut endothelial cells, as was found with another antibody against proliferating endothelium (Hagemeier et al., 1986). This antibody described by Hagemeier and colleagues (1986), termed EN7/44, reacts with a predominantly intracellular antigen whose expression appears to be linked to migration rather than proliferation (Hagemeier et al., 1986).

Immunotoxins in which the antibody portion is directed against the fibronectin receptor have also been proposed for use in killing proliferating vascular endothelial cells (Thorpe et al., 1990). However, intravenous administration of an immunotoxin containing dgA linked to the anti-fibronectin receptor antibody termed PB1 did not result in reduced vascularization of tumors (Thorpe et al., 1990). Unfortunately, further studies also revealed that fibronectin receptors were too ubiquitous to enable good targeting of tumor vasculature.

Other molecular markers have been described that are specific for endothelial cells, although not for tumor endothelial cells. For example, an endothelial-leukocyte adhesion molecule, termed ELAM-1, has been identified that can be induced on the surface of endothelial cells through the action of cytokines such as IL-1, TNF, lymphotoxin or bacterial endotoxin (Bevilacqua et al., 1987). However, the art currently lacks methods by which such inducible molecules could be effectively employed in connection with an anti-cancer strategy. Thus, unfortunately, while vascular targeting presents promising theoretical advantages, no effective strategies incorporating these advantages have been developed.

SUMMARY OF THE INVENTION

The present invention addresses one or more of the foregoing or other disadvantages in the prior art, by providing a series of novel approaches for the treatment and/or diagnosis (imaging) of vascularized solid tumors. The invention rests in a general and overall sense on the use of reagents, particularly immunological reagents, to target therapeutic or diagnostic agents to tumor-associated vascular endothelial cells, alone or in combination with the direct targeting of tumor cells.

Such antibodies or growth factors will be referred to herein as "targeting agents". Thus, the targeting compounds of the invention may be either targeting agent/therapeutic agent compounds or targeting agent/diagnostic agent compounds. Further, a targeting agent/therapeutic agent compound comprises a targeting agent operatively attached to a therapeutic agent, wherein the targeting agent recognizes and binds to a tumor-associated endothelial cell marker. A targeting agent/diagnostic agent compound comprises a targeting agent operatively attached to a diagnostic agent, wherein the targeting agent recognizes and binds to a tumor-associated endothelial cell marker. The targeting agent/therapeutic agent compounds of the invention may be produced using either standard recombinant DNA techniques or standard synthetic chemistry techniques, both of which are well known to those of skill in the art.

In the case of diagnostic agents, the constructs will have the ability to provide an image of the tumor vasculature, for example, through magnetic resonance imaging, x-ray imaging, computerized emission tomography and the like.

In the case of therapeutic agents, constructs are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis. In animal model systems, the inventors have achieved truly dramatic tumor regressions, with some cures being observed in combination therapy with anti-tumor directed therapy.

It is proposed that the various methods and compositions of the invention will be broadly applicable to the treatment or diagnosis of any tumor mass having a vascular endothelial component. Typical vascularized tumors are the solid tumors, particularly carcinomas, which require a vascular component for the provision of oxygen and nutrients. Exemplary solid tumors to which the present invention is directed include but are not limited to carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like.

A preferred method of the invention includes preparing an antibody that recognizes an antigen or other ligand associated with the vascular endothelial cells of the vascularized tumor mass, linking, or operatively attaching the antibody to the selected agent to form an antibody-agent conjugate, and introducing the antibody-agent conjugate into the bloodstream of an animal, such as a human cancer patient or a test animal in an animal model system. As used however, the term "antibody" is intended to refer broadly to any immunologic binding agent such as IgG, IgM, IgA, IgE, F(ab')$_2$, a univalent fragment such as Fab', Fab, Dab, as well as engineered antibodies such as recombinant antibodies, humanized antibodies, bispecific antibodies, and the like.

Alternatively, growth factors, rather than antibodies, may be utilized as the reagents to target therapeutic or diagnostic agents to tumor-associated vascular endothelial cells, alone, or in combination with the direct targeting of tumor cells. Any growth factor may be used for such a targeting purpose, so long as it binds to a tumor-associated endothelial cell, generally by binding to a growth factor receptor present on the surface of such a tumor-associated endothelial cell. Suitable growth factors for targeting include, but are not limited to, VEGF/VPF (vascular endothelial growth factor/vascular permeability factor), FGF (which, as used herein, refers to the fibroblast growth factor family of proteins), TFGβ (transforming growth factor β), and pleitotropin. Preferably, the growth factor receptor to which the targeting growth factor binds should be present at a higher concentration on the surface of tumor-associated endothelial cells than on non-tumor associated endothelial cells. Most preferably, the growth factor receptor to which the targeting growth factor binds should, further, be present at a higher concentration on the surface of tumor-associated endothelial cells than on any non-tumor associated cell type.

The agent that is linked to the antibody or growth factor targeting agent will, of course, depend on the ultimate application of the invention. Where the aim is to provide an image of the tumor, one will desire to use a diagnostic agent that is detectable upon imaging, such as a paramagnetic, radioactive or fluorogenic agent. Many diagnostic agents are known in the art to be useful for imaging purposes, as are methods for their attachment to antibodies (see, e.g., U.S. Pat. Nos. 5,021,236 and 4,472,509, both incorporated herein by reference). In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). Moreover, in the case of radioactive isotopes for therapeutic and/or diagnostic application, one might mention iodine$^{131}$, iodine$^{123}$, technicium$^{99m}$, indium$^{111}$, rhenium$^{188}$, rhenium$^{186}$, gallium$^{67}$, copper$^{67}$, yttrium$^{90}$, iodine$^{125}$, or astatine$^{211}$ (for a review of the use of monoclonal antibodies in the diagnosis and therapy of cancer, see Vaickus et al., 1991).

For certain applications, it is envisioned that the therapeutic agents will be pharmacologic agents will serve as useful agents for attachment to antibodies or growth factors, particularly cytotoxic or otherwise anticellular agents having the ability to kill or suppress the growth or cell division of endothelial cells. In general, the invention contemplates the use of any pharmacologic agent that can be conjugated to a targeting agent, preferably an antibody, and delivered in active form to the targeted endothelium. Exemplary anticellular agents include chemotherapeutic agents, radioisotopes as well as cytotoxins. In the case of chemotherapeutic agents, the inventors propose that agents such as a hormone such as a steroid; an antimetabolite such as cytosine arabinoside, fluorouracil, methotrexate or aminopterin; an anthracycline; mitomycin C; a vinca alkaloid; demecolcine; etoposide; mithramycin; or an antitumor alkylating agent such as chlorambucil or melphalan, will be particularly preferred. Other embodiments may include agents such as a coagulant, a cytokine, growth factor, bacterial endotoxin or the lipid A moiety of bacterial endotoxin. In any event, it is proposed that agents such as these may, if desired, be successfully conjugated to a targeting agent, preferably an antibody, in a manner that will allow their targeting, internalization, release or presentation to blood components at the site of the targeted endothelial cells as required using known conjugation technology (see, e.g., Ghose et al., 1983 and Ghose et al., 1987).

In certain preferred embodiments, therapeutic agents will include generally a plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. The use of toxin-antibody constructs is well known in the art of immunotoxins, as is their attachment to antibodies. Of these, a particularly preferred toxin for attachment to antibodies will be a deglycosylated ricin A chain. Deglycosylated ricin A chain is preferred because of its extreme potency, longer half-life, and because it is economically feasible to manufacture it a clinical grade and scale.

The present invention contemplates two separate and distinct approaches to the targeting of targeting agents, preferably antibodies, to the tumor vasculature. The first approach involves a targeting agent having a binding affinity for a marker found, expressed, accessible to binding, or otherwise localized on the cell surfaces of tumor-associated vascular endothelial cells as compared to normal, non-tumor associated vasculature. Further, certain markers for which a targeting agent has a binding affinity may be associated with the tumor-associated vasculature rather than on the tumor-associated endothelial cells, themselves. For example, such markers may be located on basement membranes or tumor-associated connective tissue. It is preferred that targeting agents specific for such non-endothelial cell markers be operatively attached to agents such as radioisotopes.

In the case of antibody targeting agents, such an approach involves the preparation of an antibody having a binding affinity for antigenic markers found, expressed, accessible to binding or otherwise localized on the cell surfaces of tumor-associated vascular endothelium as compared to normal vasculature. Such a targeting agent, preferably an antibody, is then employed to deliver the selected diagnostic or therapeutic agent to the tumor vasculature.

Naturally, where a therapeutic as opposed to diagnostic application is envisioned it will be desirable to prepare and employ an antibody having a relatively high degree of tumor vasculature selectivity, which might be expressed as having little or no reactivity with the cell surface of normal endothelial cells as assessed by immunostaining of tissue sections. Of course, with certain agents such as DNA synthesis inhibitors, and, more preferably, antimetabolites, the requirement for selectivity is not as necessary as it would be, for example, with a toxin, because a DNA synthesis inhibitor would have relatively little effect on the vascularization of normal tissues because the capillary endothelial cells are not dividing. Further, such a degree of selectivity is not a requirement for imaging purposes since cell death, and hence toxicity, is not the ultimate goal. In the case of diagnostic application, it is proposed that targeting agents, such as antibodies, having a reactivity for the tumor vasculature of at least two-fold higher than for normal endothelial cells, as assessed by immunostaining, will be useful.

This aspect of the invention rests on the proposition that because of their proximity to the tumor itself, tumor-associated vascular endothelial cells are constantly exposed to many tumor-derived products such as cytokines (including lymphokines, monokines, colony-stimulating factors and growth factors), angiogenic factors, and the like, that will bind to and serve to selectively elicit the expression of tumor endothelium-specific cell surface markers. For use in the present invention, the anti-tumor vasculature antibodies may be directed to any of the tumor-derived antigens which bind to the surface of vascular endothelial cells, and particularly to tumor-derived ligands, such as growth factors, which bind to specific cell surface receptors of the endothelial cells.

In connection with certain aspects of the invention, antibodies directed against tumor vasculature may be prepared by using endothelial cells isolated from a tumor of an animal, or by "mimicking" the tumor vasculature phenomenon in vitro. As such, endothelial cells may be subjected to tumor-derived products, such as might be obtained from tumor-conditioned media. Thus, this method involves generally stimulating endothelial cells with tumor-conditioned medium and employing the stimulated endothelial cells as immunogens to prepare a collection of antibodies, for example, by utilizing conventional hybridoma technology or other techniques, such as combinatorial immunoglobulin phagemid libraries prepared from RNA isolated from the spleen of the immunized animal. One will then select from the antibody collection an antibody that recognizes the tumor-stimulated vascular endothelium to a greater degree than it recognizes non-tumor-stimulated vascular endothelium, and reacts more strongly with tumor-associated endothelial cells in tissue sections than with those in normal adult human tissues, and producing the antibody, e.g., by culturing a hybridoma to provide the antibody.

Stimulated endothelial cells contemplated to be of use in this regard include, for example, human umbilical vein endothelial cells (RHVE), human dermal microvascular endothelial cells (HDEMC), human saphenous vein endothelial cells, human omental fat endothelial cells, other human microvascular endothelial cells, human brain capillary endothelial cells, and the like. It is also contemplated that even endothelial cells from another species may stimulated by tumor-conditioned media and employed as immunogens to generate hybridomas to produce an antibodies in accordance herewith, i.e., to produce antibodies which cross react with tumor-stimulated human vascular endothelial cells, and/or antibodies for use in pre-clinical models.

As used herein, "tumor-conditioned medium" is defined as a composition or medium, such as a culture medium, which contains one or more tumor-derived cytokines, lymphokines or other effector molecules. Most typically, tumor-conditioned medium is prepared from a culture medium in which selected tumor cells have been grown, and will therefore be enriched in such tumor-derived products. The type of medium is not believed to be particularly important, so long as it at least initially contains appropriate nutrients and conditions to support tumor cell growth. It is also, of course, possible to extract and even separate materials from tumor-conditioned media and employ one or more of the extracted products for application to the endothelial cells.

As for the type of tumor used for the preparation of the media, one will, of course, prefer to employ tumors that mimic or resemble the tumor that will ultimately be subject to analysis or treatment using the present invention. Thus, for example, where one envisions the development of a protocol for the treatment of breast cancer, one will desire to employ breast cancer cells such as ZR-75-1, T47D, SKBR3, MDA-MB-231. In the case of colorectal tumors, one may mention by way of example the HT29 carcinoma, as well as DLD-1, MCT116 or even SW48 or SW122. In the case of lung tumors, one may mention byway of example NCI-H69, SW2, NCI H23, NCI M460, NCI M69, or NCI H82. In the case of melanoma, good examples are DX.3, A375, SKMEL-23, HMB-2, MJM, T8 or indeed VUP. In any of the above cases, it is further believed that one may even employ cells produced from the tumor that is to be treated, i.e., cells obtained from a biopsy.

Once prepared, the tumor-conditioned media is then employed to stimulate the appearance of tumor endothelium-specific marker(s) on the cell surfaces of endothelial cells, e.g., by culturing selected endothelial cells in the presence of the tumor-conditioned media (or products derived therefrom). Again, it is proposed that the type of endothelial cell that is employed is not of critical importance, so long as it is generally representative of the endothelium associated with the vasculature of the particular tumor that is ultimately to be treated or diagnosed. The inventors prefer to employ human umbilical vein endothelial cells (EUVE), or human dermal microvascular endothelial cells (HDMEC, Karasek, 1989), in that these cells are of human origin, respond to cytokine growth factors and angiogenic factors and are readily obtainable. However, it is proposed that any endothelial cell that is capable of being cultured in vitro may be employed in the practice of the invention and nevertheless achieve benefits in accordance with the invention. One may mention by way of example, cells such as EA.hy9.26, ECV304, human saphenous vein endothelial cells, and the like.

Once stimulated using the tumor-derived products, the endothelial cells are then employed as immunogens in the preparation of monoclonal antibodies. The technique for preparing monoclonal antibodies against antigenic cell surface markers is quite straightforward, and may be readily carried out using techniques well known to those of skill in the art, as exemplified by the technique of Kohler & Milstein (1975). Generally speaking, the preparation of monoclonal antibodies using stimulated endothelial cells involves the following procedures. Cells or cell lines derived from human tumors are grown in tissue culture for $\geq 4$ days. The tissue culture supernatant ('tumor-conditioned medium') is removed from the tumor cell cultures and added to cultures of RHVEC at a final concentration of 50% (v/v). After 2 days culture the HUVEC are harvested non-enzymatically and $1-2\times10^6$ cells injected intraperitoneally into mice. This process is repeated three times at two-weekly intervals, the final immunization being by the intravenous route. Three days later the spleen cells are harvested and fused with SP2/0 myeloma cells by standard protocols (Kohler & Milstein, 1975): Hybridomas producing antibodies with the appropriate reactivity are cloned by limiting dilution.

From the resultant collection of hybridomas, one will then desire to select one of more hybridomas that produce an antibody that recognizes the activated vascular endothelium to a greater extent than it recognizes non-activated vascular endothelium. Of course, the ultimate goal is the identification of antibodies having virtually no binding affinity for normal endothelium. However, for imaging purposes this property is not so critical. In any event, one will generally identify suitable antibody-producing hybridomas by screening using, e.g., an ELISA, RIA, IRMA, IIF, or similar immunoassay, against one or more types of tumor-activated endothelial cells. Once candidates have been identified, one will desire to test for the absence of reactivity for non-activated or "normal" endothelium or other normal tissue or cell type. In this manner, hybridomas producing antibodies having an undesirably high level of normal cross-reactivity for the particular application envisioned may be excluded.

The inventors have applied the foregoing technique successfully, in that antibodies having relative specificity for tumor vascular endothelium have been prepared and isolated. In one particular example, the inventors employed the HT29 carcinoma to prepare the conditioned medium, which was then employed to stimulate HUVE cells in culture. The resultant HT29-activated HUVE cells were then employed as immunogens in the preparation of a hybridoma bank, which was ELISA-screened using HT29-activated HUVE cells and by immunohistologic analysis of sections of human tumors and normal tissues. From this bank, the inventors have selected antibodies that recognized a tumor vascular endothelial cell antigen.

The two most preferred monoclonal antibodies prepared by the inventors using this technique are referred to as tumor endothelial cell antibody 4 and 11 (TEC4 and TEC11). The antigen recognized by TEC4 and TEC11 was initially believed to migrate as a doublet of about 43 kilodaltons (kD), as assessed by SDS/PAGE. However, as detailed herein, the present inventors subsequently determined this antigen to be the molecule endoglin, which migrates as a 95 kD species on SDS/PAGE under reducing conditions. The epitopes on endoglin recognized by TEC4 and TEC11 are present on the cell surface of stimulated HUVE cells, and only minimally present (or immunologically accessible) on the surface of non-stimulated cells.

Monoclonal antibodies have previously been raised against endoglin (Gougos and Letarte, 1988; Gougos et al., 1992; O'Connel et al., 1992; Bühring et al., 1991). However, analyzing the reactivity with HUVEC or TCM-activated HUVEC cell surface determinants by FACS or indirect immunofluorescence shows the epitopes recognized by TEC-4 and TEC-11 to be distinct from those of a previous antibody termed 44G4 (Gougos and Letarte, 1988).

The TEC-4 and TEC-11 mAbs are envisioned to be particularly suitable for targeting human tumor vasculature as they label capillary and venular endothelial cells moderately to strongly in a broad range of solid tumors (and in several chronic inflammatory conditions and fetal placenta), but display relatively weak staining of vessels in the majority of normal, healthy adult tissues. TEC-11 is particularly preferred as it shows virtually no reactivity with non-endothelial cells. Furthermore, both TEC-4 and TEC-11 are complement-fixing, which imparts to them the potential to also induce selective lysis of endothelial cells in the tumor vascular bed.

In addition to their use in therapeutic embodiments, TEC-4 and TEC-11 antibodies may also be used for diagnostic, prognostic and imaging purposes. For example, TEC-4 and TEC-11 may be employed to identify tumors with high vessel density, which is known to correlate with metastatic risk and poor prognosis. This is a marked advance over the laborious enumeration of capillaries labelled with pan-endothelial cell markers or the use of complex and subjective in vivo assays of angiogenesis. Indeed, studies are disclosed herein which indicate that TEC-4 and TEC-11 can distinguish between intraductal carcinoma in situ (CIS), an aggressive preneoplastic lesion and lobular CIS, which is associated with a more indolent clinical course.

TEC-4 or TEC-11 antibodies may be linked to a paramagnetic, radioactive or fluorogenic ion and employed in tumor imaging in cancer patients, where it is contemplated that they will result in rapid imaging due to the location of endoglin on the luminal face of endothelial cells.

Furthermore, TEC-4 and TEC-11 are of the IgM isotype, which limits extravasation and enables more specific imaging of antigens in the intravascular compartment. This is in contrast to 44G4 which is an IgG1 antibody.

The present invention therefore encompasses anti-endoglin antibodies and antibody-based compositions, including antibody conjugates linked to paramagnetic, radioactive or fluorogenic ions and anti-cellular agents such as anti-metabolites, toxins and the like, wherein the antibodies bind to endoglin at the same epitope as either of the MAbs TEC-4 and TEC-11. Such antibodies may be of the polyclonal or monoclonal type, with monoclonals being generally preferred, especially for use in preparing endoglin-directed antibody conjugates, immunotoxins and compositions thereof.

The identification of an antibody or antibodies that bind to endoglin at the same epitopes as TEC-4 or TEC-11 is a fairly straightforward matter. This can be readily determined using any one of variety of immunological screening assays in which antibody competition can be assessed. For example, where the test antibodies to be examined are obtained from a different source to that of TEC-4 or TEC-11, e.g., a rabbit, or are even of a different isotype, for example, IgG1 or IgG3, a competition ELISA may be employed. In one such embodiment of a competition ELISA one would pre-mix TEC-4 or TEC-11 with varying amounts of the test antibodies prior to applying to the antigen-coated wells in the ELISA plate. By using either anti-murine or anti-IgM secondary antibodies one will be able to detect only the bound TEC-4 or TEC-11 antibodies—the binding of which will be reduced by the presence of a test antibody which recognizes the same epitope as either TEC-4 or TEC-11.

To conduct an antibody competition study between TEC-4 or TEC-11 and any test antibody, one may first label TEC-4 or TEC-11 with a detectable label, such as, e.g., biotin or an enzymatic or radioactive label, to enable subsequent identification. In these cases, one would incubate the labelled antibodies with the test antibodies to be examined at various ratios (e.g., 1:1, 1:10 and 1:100) and, after a suitable period of time, one would then assay the reactivity of the labelled TEC-4 or TEC-11 antibodies and compare this with a control value in which no potentially competing antibody (test) was included in the incubation.

The assay may be any one of a range of immunological assays based upon antibody binding and the TEC-4 or TEC-11 antibodies would be detected by means of detecting their label, e.g., using streptavidin in the case of biotinylated antibodies or by using a chromogenic substrate in connection with an enzymatic label or by simply detecting the radiolabel. An antibody that binds to the same epitope as TEC-4 or TEC-11 will be able to effectively compete for binding and thus will significantly reduce TEC-4 or TEC-11 binding, as evidenced by a reduction in labelled antibody binding. In the present case, after mixing the labelled TEC-4 or TEC-11 antibodies with the test antibodies, suitable assays to determine the remaining reactivity include, e.g., ELISAs, RIAs or western blots using human endoglin; immunoprecipitation of endoglin; ELISAs, RIAs or immunofluorescent staining of recombinant cells expressing human endoglin; indirect immunofluorescent staining of tumor vasculature endothelial cells; reactivity with HUVEC or TCM-activated MUVEC cell surface determinants indirect immunofluorescence and FACS analysis. This latter method is most preferred and was employed to show that the epitopes recognized by TEC-4 and TEC-11 are distinct from that of 44G4 (Gougos and Letarte, 1988).

The reactivity of the labelled TEC-4 or TEC-11 antibodies in the absence of any test antibody is the control high value.

The control low value is obtained by incubating the labelled antibodies with unlabelled antibodies of the same type, when competition would occur and reduce binding of the labelled antibodies. A significant reduction in labelled antibody reactivity in the presence of a test antibody is indicative of a test antibody that recognizes the same epitope, i.e., one that "cross-reacts" with the labelled antibody. A "significant reduction" in this aspect of the present application may be defined as a reproducible (i.e., consistently observed) reduction in binding of at least about 10%–50% at a ratio of about 1:1, or more preferably, of equal to or greater than about 90% at a ratio of about 1:100.

The present invention further encompasses antibodies which are specific for epitopes present only on growth factor/growth factor receptor complexes, while being absent from either the individual growth factor or growth factor receptor. Thus, such antibodies will recognize and bind a growth factor/growth factor receptor complex while not recognizing or binding either the growth factor molecule or growth factor receptor molecule while these molecules are not in growth factor/growth factor receptor complex form. A "growth factor/growth factor receptor complex" as used herein refers to a growth factor ligand bound specifically to its growth factor receptor, such as, by way of example only, a VEGF/VEGF receptor complex.

As it is envisioned that the growth factor/growth factor receptor complexes to which these antibodies specifically bind are present in significantly higher number on tumor-associated endothelial cells than on non-tumor associated endothelial cells, such antibodies, when used as targeting agents, serve to further increase the targeting specificity of the agents of the invention. Such antibodies may be of the polyclonal or monoclonal type, with monoclonals being generally preferred.

The second overall general approach presented by the present invention involves the selective elicitation of vascular endothelial antigen targets on the surface of tumor-associated vasculature. This approach targets known endothelial antigens that are present, or inducible, on the cell surface of endothelial cells. The key to this aspect of the invention is the successful manipulation of antigenic expression or surface presentation such that the target antigen is expressed or otherwise available on the surface of tumor associated vasculature and not expressed or otherwise available for binding, or at least to a lesser extent, on the surface of normal endothelium.

A variety of endothelial cell markers are known that can be employed as inducible targets for the practice of this aspect of the invention, including endothelial-leukocyte adhesion molecule (ELAM-1; Bevilacqua et al., 1987); vascular cell adhesion molecule-1 (VCAM-1; Dustin et al., 1986); intercellular adhesion molecule-1 (ICAM-1; Osborn et al., 1989); the agent for leukocyte adhesion molecule-1 (LAM-1 agent), or even a major histocompatibility complex (MHC) Class II antigen, such as HLA-DR, HLA-DP or HLA-DQ (dollins et al., 1984). Of these, the targeting of ELAM-1 or an MHC Class II antigen will likely be preferred for therapeutic application, with ELAM-1 being particularly preferred, since the expression of these antigens will likely be the most direct to promote selectively in tumor-associated endothelium.

The targeting of an antigen such as ELAM-1 is the most straightforward since ELAM-1 is not expressed on the surfaces of normal endothelium. ELAM-1 is an adhesion molecule that can be induced on the surface of endothelial cells through the action of cytokines such as IL-1, TNF, lymphotoxin or bacterial endotoxin (Bevilacqua et al., 1987). In the practice of the present invention, the expression of ELAM-1 is selectively induced in tumor endothelium through the use of a bispecific antibody having the ability to cause the selective release of one or more of the foregoing or other appropriate cytokines in the tumor environment, but not elsewhere in the body. This bispecific antibody is designed to cross-link cytokine effector cells, such as cells of monocyte/macrophage lineage, T cells and/or NK cells or mast cells, with tumor cells of the targeted solid tumor mass. This cross-linking is intended to effect a release of cytokine that is localized to the site of cross-linking, i.e., the tumor.

Bispecific antibodies useful in the practice of this aspect of the invention, therefore, will have a dual specificity, recognizing a selected tumor cell surface antigen on the one hand, and, on the other hand, recognizing a selected "cytokine activating" antigen on the surface of a selected leukocyte cell type. As used herein, the term "cytokine activating" antigen is intended to refer to any one of the various known molecules on the surfaces of leukocytes that, when bound by an effector molecule such as an antibody or a fragment thereof or a naturally-occurring agent or synthetic analog thereof, be it a soluble factor or membrane-bound counter-receptor on another cell, will promote the release of a cytokine by the leukocyte cell. Examples of cytokine activating molecules include CD14 and FcR for IgE, which will activate the release of IL-1 and TNF$\alpha$; and CD16, CD2 or CD3 or CD28, which will activate the release of IFN$\gamma$ and TNF$\beta$, respectively.

Once introduced into the bloodstream of an animal bearing a tumor, such a bispecific construct will bind to tumor cells within the tumor, cross-link those tumor cells with, e.g., monocytes/macrophages that have infiltrated the tumor, and thereafter effect the selective release of cytokine within the tumor. Importantly, however, without cross-linking of the tumor and leukocyte, the bispecific antibody will not effect the release of cytokine. Thus, no cytokine release will occur in parts of the body removed from the tumor and, hence, expression of ELAM-1 will occur only within the tumor endothelium.

A number of useful "cytokine activating" antigens are known, which, when cross-linked with an appropriate bispecific antibody, will result in the release of cytokines by the cross-linked leukocyte. The most preferred target for this purpose is CD14, which is found on the surface of monocytes and macrophages. When CD14 is cross linked it will stimulate the monocyte/macrophage to release IL-1, and possibly other cytokines, which will, in turn stimulate the appearance of ELAM-1 on nearby vasculature. Other possible targets for cross-linking in connection with ELAM-1 targeting includes FcR for IgE, found on Mast cells; FcR for IgG (CD16), found on NK cells; as well as CD2, CD3 or CD28, found on the surfaces of T cells. Of these, CD14 targeting will be the most preferred due to the relative prevalence of monocyte/macrophage infiltration of solid tumors as opposed to the other leukocyte cell types.

In that MHC Class II antigens are expressed on "normal" endothelium, their targeting is not quite so straightforward as ELAM-1. However, the present invention takes advantage of the discovery that immunosuppressants such as Cyclosporin A (CsA) have the ability to effectively suppress the expression of Class II molecules in the normal tissues. There are various other cyclosporins related to CsA, including cyclosporins A, B, C, D, G, and the like, which have immunosuppressive action, and will likely also demonstrate an ability to suppress Class II expression. Other agents that might be similarly useful include FK506 and rapamycin.

Thus, the practice of the MHC Class II targeting embodiment requires a pretreatment of the tumor-bearing animal with a dose of CsA or other Class II immunosuppressive agent that is effective to suppress Class II expression. In the case of CsA, this will typically be on the order of about 10 to 30 mg/kg. Once suppressed in normal tissues, Class II antigens can be selectively induced in the tumor endothelium through the use of a bispecific antibody, this one having specificity for the tumor cell as well as an activating antigen found on the surface of helper T cells. Note that in this embodiment, it is necessary that T cells, or NK cells if CD16 is used, be present in the tumor to produce the cytokine intermediate in that Class II antigen expression is achieved using IFN-γ, but is not achieved with the other cytokines. Thus, for the practice of this aspect of the invention, one will desire to select CD2, CD3 or CD28 (most preferably CD28) as the cytokine activating antigen.

An alternative approach to using "cytokine-activating" bispecific antibodies might be to activate the patients peripheral blood leukocytes or tumor-infiltrating lymphocytes in vitro (using IL-2 or autologous tumor cells for instance), reinfuse them into the patient and then localize them in the tumor with a bispecific antibody against any reliable leukocyte-specific marker, including CD5, CD8, CD11/CD18, CD15, CD32, CD44, CD45 or CD64. In order to selectively localize those leukocytes that had become activated from within a mixed population, it is recommended that the anti-leukocyte arm of the bispecific antibody should recognize a marker restricted to activate cells, such as CD25, CD30, CD54 or CD71. Neither of these approaches is favored as much as the 'cytokine-activating' antibody approach because cross-linking to tumor cells is not a prerequisite for cytokine secretion and thus the resultant induction of cytokine-induced endothelial cell antigens may not be confined to the tumor.

The targeting of the other adhesion molecules, ICAM-1, VCAM-1 and LAM-1 agent, will typically not be preferred for the practice of therapeutic embodiments, in that these targets are constitutively expressed in normal endothelium. Thus, these adhesion molecules will likely only be useful in the context of diagnostic embodiments. Furthermore, it is unlikely that ICAM-1 or VCAM-1 expression by normal endothelial cells would be inhibited in vivo by CsA because low levels of expression of both markers are constitutive properties of human endothelial cells (Burrows et al., 1991). However, it may still be possible to utilize one of these molecules in diagnostic or even therapeutic embodiments because their level of expression on the endothelial cell surface is increased 10–50 fold by cytokines. As a consequence, there may be a therapeutic or diagnostic 'window' enabling use of anti-ICAM-1 or anti-VCAM-1 conjugates in an analogous way to the proven clinical utility of some antibodies against 'tumor-associated' antigens whose expression differ quantitatively but not qualitatively from normal tissues.

The tumor antigen recognized by the bispecific antibodies employed in the practice of the present invention will be one that is located on the cell surfaces of the tumor being targeted. A large number of solid tumor-associated antigens have now been described in the scientific literature, and the preparation and use of antibodies are well within the skill of the art (see, e.g., Table II hereinbelow). Of course, the tumor antigen that is ultimately selected will depend on the particular tumor to be targeted. Most cell surface tumor targets will only be suitable for imaging purposes, while some will be suitable for therapeutic application. For therapeutic application, preferred tumor antigens will be TAG 72 or the HER-2 proto-oncogene protein, which are selectively found on the surfaces of many breast, lung and colorectal cancers (Thor et al., 1986; Colcher et al., 1987; Shepard et al., 1991). Other targets that will be particularly preferred include milk mucin core protein, human milk fat globule (Miotti et al., 1985; Burchell et al., 1983) and even the high Mr melanoma antigens recognized by the antibody 9.2.27 (Reisfeld et al., 1982).

In still further embodiments, the inventors contemplate an alternative approach for suppressing the expression of Class II molecules, and selectively eliciting Class II molecule expression in the locale of the tumor. This embodiment takes advantage of the fact that the expression of Class II molecules can be effectively inhibited by suppressing IFN-γ production by T-cells, e.g., through use of an anti-CD4 antibody (Street et al., 1989). Thus, in this embodiment, one will desire to pretreat with a dose of anti-CD4 that is effective to suppress IFN-γ production and thereby suppress the expression of Class II molecules (for example, on the order of 4 to 10 mg/kg). After Class II expression is suppressed, one will then prepare and introduce into the bloodstream an IFN-γ-producing T-cell clone (e.g., $T_1 1$ or CTL) specific for an antigen expressed on the surface of the tumor cells.

A preferred means of producing the IFN-γ-producing T-cell clone is by a method that includes removing a portion of the tumor mass from the patient, extracting tumor infiltrating leukocytes from the tumor, and expanding the tumor infiltrating leukocytes in vitro to provide the IFN-γ producing clone. This clone will necessarily be immunologically compatible with the patient, and therefore should be well tolerated by the patient. It is proposed that particular benefits will be achieved by further selecting a high IFN-γ producing T-cell clone from the expanded leukocytes by determining the cytokine secretion pattern of each individual clone every 14 days. To this end, rested clones will be mitogenically or antigenically-stimulated for 24 hours and their culture supernatants assayed by a specific sandwich ELISA technique (Cherwinski et al., 1989) for the presence of IL-2, IFN-γ, IL-4, IL-5 and IL-10. Those clones secreting high levels of IL-2 and IFN-γ, the characteristic cytokine secretion pattern of TH1 clones, will be selected. Tumor specificity will be confirmed using proliferation assays. Furthermore, one will prefer to employ as the anti-CD4 antibody an anti-CD4 Fab, because it will be eliminated from the body within 24 hours after injection and so will not cause suppression of the tumor recognizing T cell clones that are subsequently administered. The preparation of T-cell clones having tumor specificity is generally known in the art, as exemplified by the production and characterization of T cell clones from lymphocytes infiltrating solid melanoma tumors (Maeda et al., 1991).

The invention contemplates that still further advantages will be realized through combination regimens wherein both the tumor endothelial vasculature and the tumor itself are targeted. Combination regimens may thus include targeting of the tumor directly with either conventional antitumor therapy, such as with radiotherapy or chemotherapy, or through the use of a second immunological reagent such as an antitumor immunotoxin. In fact, dramatic, synergistic antitumor effects were seen by the inventors when solid tumors were targeted with both an antitumor endothelial cell immunotoxin and an antitumor cell immunotoxin. Such combination therapy is founded theoretically on 1) the use of the endothelial-directed immunotoxin to kill those tumor cells that depend upon vascular oxygen and nutrients, and 2) the use of the tumor-directed immunotoxin to kill those tumor cells that may have an alternate source of oxygen and nutrients (i.e., those tumor cells lining the vasculature and those forming the outer boundary of the tumor mass). Thus, it is proposed that particular advantages will be realized through the targeting of agents both to tumor cell targets as well as to tumor endothelial cell targets.

The invention further contemplates the selected combinations of agents particularly adapted for use in connection with the methods of the present invention, defined as including a first pharmaceutical composition which includes a bispecific antibody recognizing an activating antigen on the cell surface of a leukocyte cell and a tumor antigen on the cell surface of tumor cells of a vascularized solid tumor, together with a second pharmaceutical composition comprising a second antibody or fragment thereof linked to a selected therapeutic or diagnostic agent that recognizes the induced endothelial antigen. In accordance with one aspect of the invention, these agents may be conveniently packaged together, being suitably aliquoted into separate containers, and the separate containers dispensed in a single package.

In particular embodiments, the activating antigen induced by the bispecific antibody will be CD2, CD3, CD14, CD16, FcR for IgE, CD28 or the T-cell receptor antigen, as may be the case. However, preferably, the bispecific antibody will recognize CD14, and induce the expression of IL-1 by monocyte/macrophage cells in the tumor, or recognize CD28 and induce the expression of IFN-γ by T-cells in the tumor. Where IL-1 is the cytokine intermediate, the second antibody will preferably be one that recognizes ELAM-1, since this adhesion molecule will be induced on the surface of endothelial cells by IL-1. In contrast, where IFN-γ is the intermediate, the second antibody will preferably be one that recognizes an MHC Class II antigen. In the later case, one might desire to include with the combination a third pharmaceutical composition comprising one of the cyclosporins, or another immunosuppressive agent useful for suppressing Class II expression.

Furthermore, in that the invention contemplates combination regimens as discussed above, particular embodiments of the invention will involve the inclusion of a third pharmaceutical composition comprising an antitumor antibody conjugated to a selected agent, such as an anti-tumor immunotoxin. In these embodiments, particularly preferred will be the targeting of tumor antigens such as p185$^{HER2}$, milk mucin core protein, TAG-72, Lewis a, carcinoembryonic antigen (CEA), the high Mr melanoma antigens recognized by the 9.2.27 antibody, or the ovarian-associated antigens recognized by OV-TL3 or MOV18. These same antigens will also be preferred as the target for the bispecific antibody. Of course, where such a bispecific antibody is employed in combination with an antitumor antibody, it may be desirable to target different tumor antigens with the bispecific and antitumor antibody.

BRIEF DESCRIPTION OF THE DRAWINGS

FIG. 19a. No significant killing of proliferating HUVEC by MTSA-dgA. Quiescent (●), confluent (■) or subconfluent (▲) HUVEC cultures were incubated for 48 hours with a negative control immunotoxin (MTSA-dgA). Protein synthesis was estimated from the uptake of $^3$H-leucine during the last 24 hours of culture. Points and bars: mean and standard error of 6 individual studies.

FIG. 19b. Significant killing of proliferating RIJVEC by UV-3-dgA. Quiescent (●), confluent (■) or subconfluent (▲) PrUVEC cultures were incubated for 48 hours with a positive control immunotoxin (UV-3-dgA). Protein synthesis was estimated from the uptake of $^3$H-leucine during the last 24 hours of culture. Points and bars: mean and standard error of 6 individual studies.

DETAILED DESCRIPTION OF THE PREFERRED EMBODIMENTS

Figure 1A:
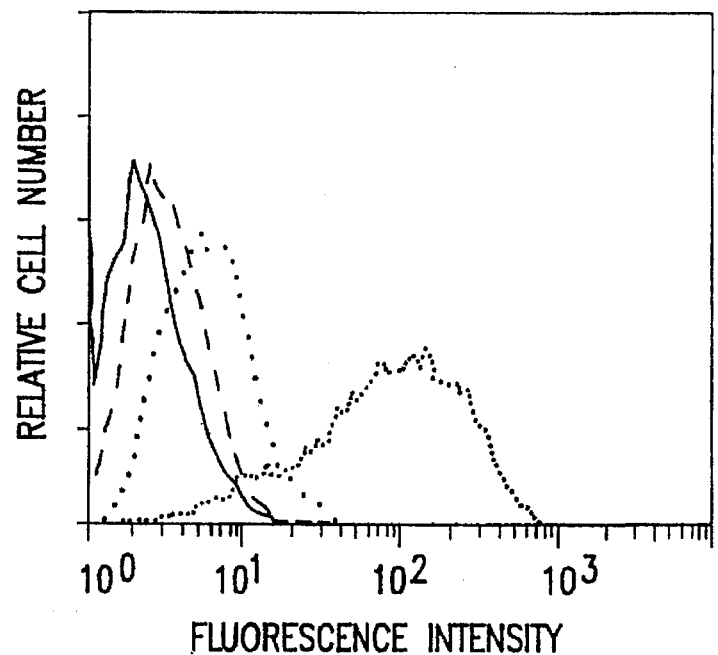
FIG. 1a. Induction of I-E$^k$ on SVEC cells by IFN-γ in regular medium, r.IFN-γ, or r.IFN-γ plus excess neutralizing anti-IFN-γ antibody. SVEC cells were cultured for 72 hours in regular medium ( - - - ), r.IFN-γ ( . . . ) or r.IFN-γ plus excess neutralizing anti-IFN-γ antibody ( . . . ). Their expression of I-E$^k$ was then measured by M5/114 antibody binding by indirect immunofluorescence using the FACS (fluorescence-activated cell sorter). Other cultures were treated with r. IFN-γ and stained with an isotype-matched control antibody ( . . . ).

Although they show great promise in the therapy of lymphomas and leukemias (Lowder et al., 1987; Vitetta et al., 1991), monoclonal antibodies (mAbs), immunotoxins (ITs) and other immunoconjugates have thus far proved relatively ineffective in clinical trials against carcinomas and other solid tumors (Byers and Baldwin, 1988; Abrams and Oldham, 1985), which account for more than 90% of all cancers in man (Shockley et al., 1991). A principal reason for this is that macromolecules do not readily extravasate into solid tumors (Sands, 1988; Epenetos et al., 1986) and, once within the tumor mass, fail to distribute evenly due to the presence of tight junctions between tumor cells (Dvorak et al., 1991), fibrous stroma (Baxter and Jain, 1991), interstitial pressure gradients (Jain, 1990) and binding site barriers (Juweid et al., 1992).

A solution to the problem of poor penetration of antibodies into solid tumors is to attack the endothelial cells (EC) lining the blood vessels in the tumor. This approach offers several advantages over direct targeting of tumor cells. Firstly, the target cells are directly accessible to intravenously administered therapeutic agents, permitting rapid localization of a high percentage of the injected dose (Burrows et al., 1990; Kennel, et al., 1991). Secondly, since each capillary provides oxygen and nutrients for thousands of cells in its surrounding 'cord' of tumor, even limited damage to the tumor vasculature could produce an avalanche of tumor cell death (Denekamp, 1984; 1986; 1990; Burrows and Thorpe, 1993). The outgrowth of mutant endothelial cells lacking the target antigen is unlikely because endothelial cells are normal and not neoplastic cells. Finally, endothelial cells are similar in different tumors, making it feasible to develop a single reagent for treating numerous types of cancer.

For tumor vascular targeting to succeed, targeting agents, such as antibodies, are required that recognize tumor endothelial cells but not those in normal tissues. Differences between tumor blood vessels and normal ones have been documented (reviewed in Denekamp, 1990; Dvorak et al., 1991; and Jain, 1988) which suggested to the inventors that antigenic differences might exist. For example, tumors elaborate angiogenic factors (Kandel et al., 1991; Folkman, 1985) and cytokines (Burrows et al., 1991; Ruco et al., 1990; Borden et al., 1990) which alter the behavior and phenotype of local endothelial cells. Vascular endothelial cells in tumors proliferate at a rate 30-fold greater than those in miscellaneous normal tissues (Denekamp et al., 1982), suggesting that proliferation-linked determinants could serve as markers for tumor vascular endothelial cells.

Nevertheless, despite fairly intensive efforts in several laboratories (Duijvestijn et al., 1987, Hagemeier et al., 1986; Schlingmann et al., 1985), antibodies have not yet been obtained which clearly distinguish tumor from normal vasculature. Migration-linked endothelial markers have been described, but as yet none has been found to be reliably and selectively expressed in the tumor vasculature (Gerlach et al., 1989; Hagemeier et al., 1986; Sarma et al., 1992). For example, the antigen recognized by the antibody termed EN7/44 (Hagemeier et al., 1986) appears to be linked to migration rather than to proliferation, and, since it is almost entirely cytoplasmically located, is not believed to be a good candidate for tumor vasculature targeting.

VEGF receptors are known to be upregulated on tumor endothelial cells as opposed to endothelial cells in normal tissues, both in rodents and man. Possibly, this is a consequence of hypoxia—a characteristic of the tumor microenvironment. FGI receptors are also upregulated three-fold on endothelial cells exposed to hypoxia, and so are probably upregulated in tumors.

Both VEGF and bFGF are concentrated in or on tumor vasculature and potentially provide a target for attack on tumor vasculature. TGF β receptor (endoglin) on endothelial cells is upregulated on dividing cells (as shown herein), explaining the greater binding on TEC-11 to tumor vasculature where endothelial cells are dividing.

Tumor endothelial markers could potentially be induced directly by tumor-derived cytokines (Burrows et al., 1991; Ruco et al., 1990) or angiogenic factors (Mignatti et al., 1991). In support of the existence of tumor vasculature markers, two antibodies against unrelated antigens of unknown function that are expressed in the vasculature of human tumors but not in most normal tissues have been described subsequent to the present invention (Rettig et al., 1992; Wang et al., 1993).

The present inventors have developed a variety of strategies for specifically targeting the targeting agents, such as antibodies, to tumor vasculature that address the shortcomings in the prior approaches. One strategy for vascular targeting presented by the invention involves the use of a targeting agent, such as an antibody directed against a tumor vasculature-associated antigen, whether specifically bound to the vasculature surface or expressed by an endothelial cell, to target deliver a selected therapeutic or diagnostic agent to the tumor. In addition to an antibody, the targeting agent may be a growth factor which specifically binds a growth factor receptor present on the surface of a tumor-associated endothelial cell. A second approach involves the selective induction of MHC Class II molecules on the surfaces of tumor-associated endothelia which can then serve as endothelial cell targets. A third, related but distinct approach involves the selective elicitation of an endothelial marker in the tumor vascular endothelium and the targeting of such as antigen with an appropriate antibody. Naturally, the existence of endothelial markers, such as ELAM-1, VCAM-1, ICAM-1 and the like, has been documented, however exploiting such molecules by selective induction and subsequent targeting has not been described previously.

A. IDENTIFICATION OF EXISTING TUMOR VASCULATURE MARKERS

The present inventors developed a novel approach to identify tumor vascular antigens which employs tumor-conditioned cell culture media to induce specific antigens on vascular endothelial cells. The conditioned media, which undoubtedly includes numerous cytokines, growth factors and tumor-specific products, mimics the solid tumor vascular environment and thereby promotes the appearance of specific tumor vascular antigen markers. This approach allows specific markers of tumor vasculature to be identified and then targeted with a targeting agent, such as a specific antibody, linked, or operatively attached to, a selected therapeutic or diagnostic agent.

The generation of antibodies against specific markers of tumor vasculature generally involves using the stimulated endothelial cells as immunogens in an animal system. The methods of generating polyclonal antibodies in this manner are well known, as are the techniques of preparing monoclonal antibodies via standard hybridoma technology. The inventors also contemplate the use of a molecular cloning approach to generate monoclonals. For this, combinatorial immunoglobulin phagemid libraries are prepared from RNA isolated from the spleen of the immunized animal, and phagemids expressing appropriate antibodies are selected by panning on normal-versus-tumor endothelium. The advantages of this approach over conventional hybridoma techniques are that approximately $10^4$ times as many antibodies can be produced and screened in a single round, and that new specificities are generated by H and L chain combination which further increases the chance of finding appropriate antibodies.

In one of the studies disclosed herein, the inventors report the development and characterization of two murine IgM monoclonal antibodies, TEC-4 and TEC-11, which are envisioned to be suitable for targeting the tumor vasculature of humans. TEC-4 and TEC-11 were initially believed to recognize an antigen that migrated as a 43 kD doublet on SDS/PAGE. However, as detailed herein, the present inventors subsequently determined this antigen to be the molecule endoglin, which is a dimeric glycoprotein consisting of 95 kDa disulfide-linked subunits whose primary sequence is known (Gougos, 1990). Monoclonal antibodies have previously been raised against endoglin (Gougos and Letarte, 1988; Gougos et al., 1992; O'Connel et al., 1992; Bühring et al., 1991). However, TEC-4 and TEC-11 are believed to recognize distinct epitopes, as shown, for example, by the failure of 44G4 to block TEC-4 or TEC-11, even at high ratios.

Endoglin is expressed on human endothelial cells, fetal syncytiotrophoblast (Gougos et al., 1992), some macrophages (O'Connell et al., 1992), immature erythroid cells (Bühring et al., 1991), and some leukemic and hemopoietic cell lines (Gougos and Letarte, 1988; Gougos et al., 1992; O'Connel et al., 1992; BGhring et al., 1991). Its expression on dermal endothelium has recently been demonstrated to be upregulated in several chronic inflammatory skin lesions (Westphal et al., 1993).

Using the TEC-4 and TEC-11 antibodies, the inventors report herein that endoglin is upregulated on activated and dividing HUVEC in culture, and is strongly expressed in human tissues on endothelial cells at sites of neovascularization, including a broad range of solid tumors and fetal placenta. In contrast, endothelial cells in the majority of miscellaneous non-malignant adult tissues, including preneoplastic lesions, were only weakly positive or not stained by TEC-4 and TEC-11. Importantly, TEC-4 and TEC-11 antibody binding is also shown to correlate with neoplastic progression in the breast: benign fibroadenomas, and early carcinoma-in-situ bound low levels of TEC-4 and TEC-11 whereas late stage intraductal carcinomas and invasive carcinomas bound high levels of the antibodies.

HUVEC in sections of umbilical vein react weakly with TEC-4 and TEC-11, whereas proliferating EUVEC in tissue culture react strongly and uniformly. HUVEC cultures grown to confluence and then rested contain two subpopulations having high and low levels of endoglin expression. Multiparameter analysis by FACS revealed that a significant proportion of cells with high endoglin expression are cycling, having markedly increased levels of cellular protein, RNA and DNA by comparison with low endoglin-expressing cells, which appear all to be non-cycling. Taken together, the increased binding of TEC-4 and TEC-11 to tumor vasculature and to dividing as opposed to non-cycling HUVEC in vitro indicates that endoglin is an endothelial cell proliferation-associated marker. Anti-endoglin antibodies are thus proposed to have broad-based applicability in the diagnosis, imaging and therapy of solid tumors in man. Furthermore, the uniformity of staining of vessels in different tumors and within any individual tumor indicates that TEC-4 and TEC-11 compare favorably with various other antibodies, such as, e.g., FB-5 (Rettig et al., 1992) and E9 (Wang et al., 1993).

An additional concept of one of the present inventors is the use of "tumor-derived endothelial cell binding factors"

as a means of distinguishing between tumor vasculature and the vasculature of normal tissues. That is, if tumors secrete factors for which vascular endothelial cells have receptors, the endothelial cells in the tumor will capture that factor and display it on their surface. In contrast, endothelial cells in normal tissues will bind relatively little of the factor because it is diluted within the blood pool or because the receptors on normal endothelial cells are not upregulated as they are on tumor endothelial cells. Thus, operationally, the tumor-derived factor will also constitute a tumor endothelial cell marker.

Such tumor-derived endothelial cell binding factors can be manufactured by the tumor cells themselves, by cells (e.g. macrophages, mast cells) which have infiltrated tumors or by platelets which become activated within the tumor. It is proposed that an antibody or other ligand which recognizes that factor will home selectively to tumor vasculature after injection. Such an antibody or ligand should thus enable the imaging or targeting of drugs or other agents to solid tumors. Further, such an antibody may be specific for a factor/factor receptor complex present on the surface of the tumor vasculature, so that the antibody recognizes only a factor/factor receptor complex, while not binding to either the factor or the factor receptor individually.

Various candidate factors include, for example, vascular endothelial cell growth factor (VEGF), also called vascular permeability factor (VPF); members of the fibroblast growth factor (FGF) family, e.g., basic FGF; Tumor necrosis factor-α (TNF-α); transforming growth factor-α (TGF-α) and transforming growth factor-α (TGF-α); angiogenic; angiotropin; and platelet-derived endothelial cell growth factor (PD-ECGF).

B. SELECTIVE INDUCTION OF OTHER TUMOR VASCULATURE MARKERS

Another approach to targeting tumor vasculature involves the selective induction of a molecule that is capable of acting as a marker for subsequent tumor endothelial cell targeting. Within this general strategy, the inventors have focused on both the induction of MHC Class II molecules and the induction of endothelial cell adhesion molecules. The MEC Class II approach, however, requires that MHC Class II expression be effectively inhibited in normal tissues. It is known that CsA and related immunosuppressants have this capability via inhibition of T cell activation, and can therefore be employed to pretreat the patient or animal to inhibit Class II expression. Alternatively, it is proposed that inhibition of Class II expression can be achieved using anti-CD4 in that CD4 directed antibodies are known to additionally suppress T cell function (Street et al., 1989). Then, Class II targets are selectively induced in the tumor-associated vascular endothelium through a locally released cytokine intermediate (IFN-γ).

To use the related approach of selectively eliciting an endothelial marker in tumor vascular endothelium, one may exploit one or more of the various endothelial adhesion molecules. The expression of an endothelial adhesion molecule, such as ELAM-1, VCAM-1, ICAM-1, LAM-1 ligand etc., may thus be selectively induced and then targeted with an appropriate antibody. Of these, ELAM-1 is the preferred target in that it is quite clear that this antigen is not expressed in normal endothelial vasculature (Cotran et al., 1986). The other adhesion molecules appear to be expressed to varying degrees in other normal tissues, generally in lymphoid organs and on endothelium, making their targeting perhaps appropriate only in diagnostic embodiments.

In either case, the key is the use of a bispecific "cytokine-inducing" antibody that will selectively induce the release of the appropriate cytokine in the locale of the tumor. This specifically localized release of cytokine is achieved through a bispecific antibody having the ability to "cross-link" cytokine-producing leukocytes to cells of the tumor mass. The preparation and use of bispecific antibodies such as these is predicated in part on the fact that cross-linking antibodies recognizing CD3, CD14, CD16 and CD28 have previously been shown to elicit cytokine production selectively upon cross-linking with the second antigen (Qian et al., 1991). In the context of the present invention, since only successfully tumor cell-crosslinked leukocytes will be activated to release the cytokine, cytokine release will be restricted to the locale of the tumor. Thus, expression of ELAM-1 will be similarly limited to the endothelium of the tumor vasculature.

An overview of various exemplary inducible vascular endothelial targets, as well as the mechanisms for their induction, is set forth in Table I. This Table lists various potential endothelial cell targets, such as ELAM-1, VCAM-1, etc., the inducing intermediate cytokine, such as IL-1, IFN-γ, etc., and the leukocyte cell type and associated cytokine activating molecule whose targeting will result in the release of the cytokine. Thus, for example, a bispecific antibody targeted to an appropriate solid tumor antigen and CD14, will promote the release of IL-1 by tumor-localized monocytes and macrophages, resulting in the selective expression of the various adhesion molecules in the tumor vascular endothelium. Alternatively, the bispecific antibody may be targeted to FcR for IgE, FcR for IgG (CD16), CD2, CD3, or CD28, and achieve a similar result, with the cytokine intermediate and cytokine-producing leukocyte being different or the same.

TABLE I

POSSIBLE INDUCIBLE VASCULAR TARGETS

| INDUCIBLE ENDOTHELIAL CELL MOLECULES | ACRONYM | SUBTYPES/ALIASES (MOLECULAR FAMILY) | INDUCING CYTOKINES | LEUKOCYTES WHICH PRODUCE THOSE CYTOKINES | LEUKOCYTE MOLECULES WHICH, WHEN CROSSLINKED BY MONOCLONAL ANTIBODIES ACTIVATE THE CELLS TO PRODUCE CYTOKINES |
|---|---|---|---|---|---|
| Endothelial-Leukocyte Adhesion Molecule-1 | ELAM-1 | — (Selectin) | IL-1, TNF-α, (TNF-β) (Bacterial Endotoxin) | monocytes macrophages mast cells | CD14 CD14 FcR for IgE |
| Vascular Cell Adhesion | VCAM-1 | Inducible Cell Adhesion | (Bacterial Endotoxin) | monocytes macrophages | CD14 CD14 |

TABLE I-continued

POSSIBLE INDUCIBLE VASCULAR TARGETS

| INDUCIBLE ENDOTHELIAL CELL MOLECULES | ACRONYM | SUBTYPES/ALIASES (MOLECULAR FAMILY) | INDUCING CYTOKINES | LEUKOCYTES WHICH PRODUCE THOSE CYTOKINES | LEUKOCYTE MOLECULES WHICH, WHEN CROSSLINKED BY MONOCLONAL ANTIBODIES ACTIVATE THE CELLS TO PRODUCE CYTOKINES |
|---|---|---|---|---|---|
| Molecule-1 | | Molecule-110 (INCAM-110) (Immunoglobulin Family) | IL-1, TNF-α | mast cells | FcR for IgE |
| | | | TNF-β, IL-4 | helper T cells | CD2, CD3, CD28 |
| Intercellular Adhesion Molecule-1 | ICAM-1 | — (Immunoglobulin Family) | TNF | NK cells | FcR for IgG (CD16) |
| | | | IL-1, TNFα (Bacterial Endotoxin) | monocytes | CD14 |
| | | | | macrophages | CD15 |
| | | | | mast cells | FcR for IgE |
| | | | TNF-β, IFNγ | T helper cells | CD2, CD3, CD28 |
| | | | | NK cells | FcR for IgG (CD16) |
| The Agent for Leukocyte Adhesion Molecule-1 | LAM-1 Agent | MEL-14 Agent (Mouse) | Il-1, TNFα (Bacterial Endotoxin) | monocytes | CD14 |
| | | | | macrophages | CD14 |
| | | | | mast cells | FcR for IgE |
| Major Histocompatibility Complex Class II Antigen | MHC Class II | HLA-DR HLA-DP - Human HLA-DQ I-A - Mouse I-E | IFN-γ | helper T cells | CD2, CD3, CD28 |
| | | | | NK cells | FcR for IgG (CD16) |

As pointed out, the distinction between the selective activation of ELAM-1 and the MHC Class II molecules rests on the fact that ELAM-1 is not normally expressed in normal epithelium, whereas Class II molecules are normally expressed in normal endothelium. Thus, when one seeks to target MHC Class II antigens, it will be important to first inhibit their expression in normal tissues using CsA or a similar immunosuppressant agent having the ability to suppress MHC Class II expression. Then, MHC Class II molecules can be selectively induced in the tumor vasculature using, e.g., a bispecific antibody against a solid tumor antigen that activates $T_h1$ cells in the tumor in a CsA-independent fashion, such as CD28. Such an antibody will trigger the release of IFN-γ which, in turn, will result in the selective expression of Class II molecules in the tumor vasculature.

An alternative approach that avoids both the use of CsA and a bispecific activating antibody involves the use of anti-CD4 to suppress IFN-γ production, followed by introduction of an IFN-γ-producing T-cell clone (e.g., $T_h1$ or cytotoxic T-lymphocytes (CTLs)) that is specific for a selected tumor antigen. In this embodiment, the T-cell clone itself localizes to the tumor mass due to its antigen recognition capability, and only upon such recognition will the T-cell clone release IFN-γ. In this manner, cytokine release is again restricted to the tumor, thus limiting the expression of Class II molecules to the tumor vasculature.

T lymphocytes from the peripheral blood (Mazzocchi et al., 1990) or within the tumor mass (Fox et al., 1990) will be isolated by collagenase digestion where necessary, and density gradient centrifugation followed by depletion of other leukocyte subsets by treatment with specific antibodies and complement. In addition, CD4⁺ or CD8⁺ T cell subsets may be further isolated by treatment with anti-CD8 or anti-CD4 and complement, respectively. The remaining cells will be plated at limiting dilution numbers in 96-well (round bottom) plates, in the presence of $2 \times 10^5$ irradiated (2500 rad) tumor cells per well. Irradiated syngeneic lymphocytes ($2 \times 10^5$ per well) and interleukin-2 (10 U/ml) will also be included. Generally, clones can be identified after 14 days of in vitro culture. The cytokine secretion pattern of each individual clone will be determined every 14 days. To this end, rested clones will be mitogenically or antigenically-stimulated for 24 hours and their culture supernatants assayed for the presence of IL-2, IFN-γ, IL-4, IL-5 and IL-10. Those clones secreting high levels of IL-2 and IFN-γ, the characteristic cytokine secretion pattern of $T_{H1}$ clones, will be selected. Tumor specificity will be confirmed utilizing proliferation assays.

Supernatants obtained after 24 hour mitogen or antigen-stimulation will be analyzed in the following cytokine assays: IL-2, IFN-γ, IL-4, IL-5 and IL-10. The levels of IL-2 and IL-4 will be assayed using the HT-2 bioassay in the presence of either anti-IL-2, anti-IL-4 antibodies or both. The remaining cytokines will be assayed using specific two-site sandwich ELISAs (Cherwinski et al., 1989). Cytokines in the unknown samples will be quantitated by comparison with standard curves, by using either linear or four-parameter curve-fitting programs.

A few generalizations can be made as to which approach would be the more appropriate for a given solid tumor type. Generally speaking, the more "immunogenic" tumors would be more suitable for the MHC Class II approach involving, e.g., the cross-linking of T-cells in the tumor through an anti-CD28/anti-tumor bispecific antibody, because these tumors are more likely to be infiltrated by T cells, a prerequisite. Examples of immunogenic solid tumors include renal carcinomas, melanomas, a minority of breast and colon cancers, as well as possibly pancreatic, gastric, liver, lung and glial tumor cancers. These tumors are referred to as "immunogenic" because there is evidence that they elicit immune responses in the host and they have been found to be amenable to cellular immunotherapy (Yamaue et al., 1990). In the case of melanomas and large bowel cancers, the most preferred antibodies for use in these instances would be B72.3 (anti-TAG-72) and PRSC5/PR4C2 (anti-Lewis a) or 9.2.27 (anti-high Mr melanoma antigen).

For the majority of solid tumors of all origins, an anti-CD14 approach that employs a macrophage/monocyte intermediate would be more suitable. This is because most tumors are rich in macrophages. Examples of macrophage-rich tumors include most breast, colon and lung carcinomas. Examples of preferred anti-tumor antibodies for use in these instances would be anti-HER-2, B72.3, SM-3, HMFG-2, and SWA11 (Smith et al., 1989).

The inventors have recently developed a model system in the mouse in which to demonstrate and investigate immunotoxin-mediated targeting of vascular endothelial cells in solid tumors. A neuroblastoma transfected with the murine interferon-γ (IFN-γ) is grown in SCID or BALB/c nude mice reared under germ-free conditions. The IFN-γ secreted by the tumor cells induces the expression of MHC Class II antigens on the vascular endothelial cells in the tumor. Class II antigens are absent from the vasculature of normal tissues in germ-free SCID and nude mice although they are present on certain non-life-sustaining normal cells (such as on B lymphocytes and monocytes) and some epithelial cells.

When mice with large (1.2 cm diameter) tumors were injected with anti-Class II-ricin A chain immunotoxin, dramatic anti-tumor effects were observed. Histological examination of tumors taken from mice at various times after injecting the immunotoxin revealed that vascular endothelial cell degeneration was the first discernable event followed by platelet deposition on the injured vessels and coagulation of the tumor blood supply. This was followed by extensive tumor cell degeneration which occurred within 24 hours after injection of the immunotoxin. By 72 hours, no viable tumor cells remained apart from a few cells on the edge of the tumor where it penetrated into the normal tissues. These surviving tumor cells could be killed by administering an immunotoxin directed against the tumor cells themselves, resulting in lasting complete tumor regressions in a third of the animals.

These background studies have demonstrated the feasibility of targeting tumor vasculature through targeting of MHC Class II or adhesion molecules such as ELAM-1.

C. MHC CLASS II

Class II antigens are expressed on vascular endothelial cells in most normal tissues in several species, including man. Studies in vitro (Collins et al., 1984; Daar et al., 1984; O'Connell et al., 1990) and in vivo (Groenewegen et al., 1985) have shown that the expression of Class II antigens by vascular endothelial cells requires the continuous presence of IFN-γ which is elaborated by $T_{H1}$ cells and, to a lesser extent, by NK cells and CD8$^+$ T cells. As shown in the dog (Groenewegen et al., 1985) and as confirmed by the inventors in normal mice, Class II expression through the vasculature is abolished when CsA is administered. The CsA acts by preventing the activation of T cells and NK cells (Groenewegen et al., 1985; DeFranco, 1991), thereby reducing the basal levels of IFN-γ below those needed to maintain Class II expression on endothelium.

A strategy for confining Class II expression to tumor vasculature is to suppress IFN-γ production through out the animal by administering CsA and then to induce IFN-γ production specifically in the tumor by targeting a CsA-resistant T cell activator to the tumor. A bispecific (Fab'—Fab') antibody having one arm directed against a tumor antigen and the other arm directed against CD28 should localize in the tumor and then crosslink CD28 antigens on T cells in the tumor. Crosslinking of CD28, combined with a second signal (provided, for example, by IL-1 which is commonly secreted by tumor cells (Burrows et al., 1991; Ruco et al., 1990) has been shown to activate T cells through a CA2+-independent non-CsA-inhibitable pathway (Hess et al., 1991; June et al., 1987; Bjorndahl et al., 1989). The T cells that should be activated in the tumor are those adjacent to the vasculature since this is the region most accessible to cells and is also where the bispecific antibody will be most concentrated. The activated T cells should then secrete IFN-γ which induces Class II antigens on the adjacent tumor vasculature.

MHC Class II antigens are not unique to vascular endothelial cells. They are expressed constitutively on B cells, activated T cells, cells of monocyte/macrophage linage and on certain epithelial cells both in mice (Hammerling, 1976) and in man (Daar et al., 1984). It would therefore be anticipated that damage to these normal tissues would result if anti-Class II immunotoxin were to be administered. However this presumption is not correct, at least in mice. Anti-Class II immunotoxins administered intravenously to germ-free SCID or BALB/c nude mice are no more toxic to the mice than are immunotoxins having no reactivity with mouse tissues. There are a number of possible explanations for this surprising result. First, anti-Class II antibodies injected intravenously do not appear to reach the epithelial cells or the monocytes/macrophages in organs other than the liver and spleen. Presumably this is because the vascular endothelium in most organs is tight, not fenestrated as it is in the liver and spleen, and so the antibodies must diffuse across basement membranes to reach the Class Ii-positive cells.

Secondly, hepatic Kupffer cells and probably other cells of monocyte/macrophage lineage are not killed by the anti-Class II immunotoxin even though it binds to them. No morphological changes in the Kupffer cells are visible even several days after administration of the immunotoxin. This is probably because cells of monocyte/macrophage linage are generally resistant to immunotoxin-mediated killing (Engert et al., 1991). Cells of monocyte/macrophage lineage appear to bind and internalize immunotoxins but route them to the lysosomes where they are destroyed, unlike other cell types which route immunotoxins to the trans-Golgi region or the E.R. which are thought to be 10 site(s) from which ricin A chain enters the cytosol (Van Deurs et al., 1986; Van Deurs et al., 1988).

Finally, there were little morphological evidence of splenic damage despite the fact that the immunotoxin bound to the B cells and that the cells are sensitive to anti-Class II immunotoxins (Lowe et al., 1986; Wu et al., 1990). It is possible that the B cells were killed, but, being metabolically inactive, they degenerated very slowly. In any event, B cell elimination is unlikely to be a significant problem in mice or in man because the cells would be replenished from Class II negative progenitors (Lowe et al., 1986); indeed, in B lymphoma patients and normal monkeys treated with anti-B cell immunotoxins, B cell killing definitely occurs but causes no obvious harm (Vitetta et al., 1991).

D. ELAM-1

In contrast to Class II, ELAM-1 is not found on the vasculature of normal tissues in humans and is absent from any other cell types (Cotran et al., 1986). It is induced on vascular endothelial cells by IL-1 and TNV but not by IFN-γ (Wu et al., 1990). Its induction is rapid, peaking at 4-6 hours and, thereafter, it is rapidly lost, being hardly detectable by 24 hours (Bevilacqua et al., 1987).

With ELAM-1, the strategy is to induce its expression selectively on tumor vasculature using a bispecific antibody that will home to the tumor and activate monocytes/macrophages within the tumor. The bispecific antibody will have one Fab' arm directed against a tumor antigen and the other directed against CD14 (the LPS receptor). After localizing in the tumor, the bispecific antibody should crosslink CD14 receptors on monocytes and the macrophages within the tumor. This should result in powerful activation of these cells (Schutt et al., 1988; Chen et al., 1990) and the production of IL-1 and TNF which will induce ELAM-1 on tumor vascular endothelial cells.

E. PREPARATION OF TARGETING AGENT ANTIBODIES

The origin or derivation of the targeting agent antibody or antibody fragment (e.g., Fab', Fab or F(ab')$_2$) is not believed to be particularly crucial to the practice of the invention, so long as the antibody or fragment that is actually employed for the preparation of bispecific antibodies otherwise exhibit the desired activating or binding properties. Thus, where monoclonal antibodies are employed, they may be of human, murine, monkey, rat, hamster, chicken or even rabbit origin. The invention contemplates that the use of human antibodies, "humanized" or chimeric antibodies from mouse, rat, or other species, bearing human constant and/or variable region domains, single domain antibodies (e.g., DABs), Fv domains, as well as recombinant antibodies and fragments thereof. Of course, due to the ease of preparation and ready availability of reagents, murine monoclonal antibodies will typically be preferred.

In general, the preparation of bispecific antibodies is also well known in the art, as exemplified by Glennie et al. (1987), as is their use in the activation of leukocytes to release cytokines (Qian et al., 1991). Bispecific antibodies have even been employed clinically, for example, to treat cancer patients (Bauer et al., 1991). Generally speaking, in the context of the present invention the most preferred method for their preparation involves the separate preparation of antibodies having specificity for the targeted tumor cell antigen, on the one hand, and the targeted activating molecule on the other. While numerous methods are known in the art for the preparation of bispecific antibodies, the Glennie et al. (1987) method preferred by the inventors involves the preparation of peptic F(ab'γ)$_2$ fragments from the two chosen antibodies (e.g., an antitumor antibody and an anti-CD14 or anti-CD28 antibody), followed by reduction of each to provide separate Fab'$_{γSH}$ fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired F(ab'γ)$_2$ heteroconjugate.

While, due to ease of preparation and high yield and reproducibility, the Glennie et al. (1987) method is preferred for the preparation of bispecific antibodies, there are of course numerous other approaches that can be employed and that are envisioned by the inventors. For example, other techniques are known wherein crosslinking with SPDP or protein A is carried out, or a trispecific construct is prepared (Titus et al., 1987; Tutt et al., 1991). Furthermore, recombinant technology is now available for the preparation of antibodies in general, allowing the preparation of recombinant antibody genes encoding an antibody having the desired dual specificity (Van Duk et al., 1989). Thus, after selecting the monoclonal antibodies having the most preferred binding and activation characteristics, the respective genes for these antibodies can be isolated, e.g., by immunological screening of a phase expression library (Oi & Morrison, 1986; Winter & Milsrein, 1991). Then, through rearrangement of Fab coding domains, the appropriate chimeric construct can be readily obtained.

The preparation of starting antibodies against the various cytokine activating molecules is also well known in the art. For example, the preparation and use of anti-CD14 and anti-CD28 monoclonal antibodies having the ability to induce cytokine production by leukocytes has now been described by several laboratories (reviewed in Schutt et al., 1988; Chen et al., 1990, and June et al., 1990, respectively). Moreover, the preparation of monoclonal antibodies that will stimulate leukocyte release of cytokines through other mechanisms and other activating antigens is also known (Clark et al., 1986; Geppert et al., 1990).

Similarly, there is a very broad array of antibodies known in the art that have immunological specificity for the cell surface of virtually any solid tumor type, as a vast number of solid tumor assorted antigens have been identified (see, e.g., Table II). Methods for the development of antibodies that are "custom-tailored" to the patient's tumor are likewise known (Stevenson et al., 1990). Of course, not all antibodies will have sufficient selectivity, specificity, affinity and toxin-delivering capability to be of use in the practice of the invention. These properties can be readily evaluated using conventional immunological screening methodology.

TABLE II

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| A: Gynecological | | | |
| GY | 'CA 125' >200 kD mucin GP | OC 125 | Kabawat et al., Int. J. Gynecol. Pathol, 4:265, 1983; Szymendera, Tumour Biology, 7:333, 1986 |
| ovarian | 80 Kd GP | OC 133 | Masuko et al, Cancer Res., 44:2813, 1984 |
| ovarian | 'SGA' 360 Kd GP | OMI | de Krester et al., Int. J. Cancer, 37:705, 1986 |
| ovarian | High M$_r$ mucin | Mo v1 | Miotti et al, Cancer Res., 65:826, 1985 |
| ovarian | High M$_r$ mucin/ glycolipid | Mo v2 | Miotti et al, Cancer Res., 65:826, 1985 |
| ovarian | NS | 3C2 | Tsuji et al., Cancer Res., 45:2358, 1985 |

TABLE II-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| ovarian | NS | 4C7 | Tsuji et al., Cancer Res., 45:2358, 1985 |
| ovarian | High $M_r$ mucin | ID$_3$ | Gangopadhyay et al., Cancer Res., 45:1744, 1985 |
| ovarian | High $M_r$ mucin | DU-PAN-2 | Lan et al, Cancer Res., 45:305, 1985 |
| GY | 7700 Kd GP | F 36/22 | Croghan et al., Cancer Res., 44:1954, 1984 |
| ovarian | 'gp 68' 48 Kd GP | 4F$_7$/7A$_{10}$ | Bhattacharya et al., Cancer Res., 44:4528, 1984 |
| GY | 40, 42kD GP | OV-TL3 | Poels et al., J. Natl. Cancer, 76:781, 1986 |
| GY | 'TAG-72' High $M_r$ mucin | B72.3 | Thor et al., Cancer Res., 46:3118, 1986 |
| ovarian | 300–400 Kd GP | DF$_3$ | Kufe et al., Hybridoma, 3:223, 1984 |
| ovarian | 60 Kd GP | 2C$_8$/2F$_7$ | Bhattacharya et al., Hybridoma, 4:153, 1985 |
| GY | 105 Kd GP | MF 116 | Mattes et al., PNAS, 81:568, 1984 |
| ovarian | 38–40 kD GP | MOv18 | Miotti et al., Int. J. Cancer 39:297, 1987 |
| GY | 'CEA' 180 Kd GP | CEA 11-H5 | Wagener et al., Int. J. Cancer, 33:469, 1984 |
| ovarian | CA 19-9 or GICA | CA 19-9 (1116NS 19-9) | Atkinson et al., Cancer Res., 62:6820, 1982 |
| ovarian | 'PLAP' 67 Kd GP | H17-E2 | McDicken et al., Br. J. Cancer, 52:59, 1985 |
| ovarian | 72 Kd | 791T/36 | Perkins et al., Eur. J. Nucl. Med., 10:296, 1985 |
| ovarian | 69 Kd PLAP | NDOG$_2$ | Sunderland et al., Cancer Res., 44:4496, 1984 |
| ovarian | unknown $M_r$ PLAP | H317 | Johnson et al., Am. J. Reprod. Immunol., 1:246, 1981 |
| ovarian | p185$^{HER2}$ | 4D5, 3H4, 7C2, 6E9, 2C4, 7F3, 2H11, 3E8, 5B8, 7D3, SB8 | Shepard et al., J. Clin. Immunol., 11(3):117, 1991 |
| uterus ovary | HMFG-2 | HMFG2 | Epenetos et al., Lancet, Nov. 6, 1000–1004, 1982 |
| GY | HMFG-2 | 3.14.A3 | Burchell et al., J. Immunol., 131:508, 1983 |
| B: BREAST | | | |
|  | 330–450 Kd GP | DF3 | Hayes et al., J. Clin. Invest., 75:1671, 1985 |
|  | NS | NCRC-11 | Ellis et al., Histopathol., 8:501, 1984 |
|  | 37kD | 3C6F9 | Mandeville et al., Cancer Detect. Prev., 10:89, 1987 |
|  | NS | MBE6 | Teramoto et al., Cancer, 50:241, 1982 |
|  | NS | CLNHS | Glassy et al., PNAS, 80:63227, 1983 |
|  | 47 Kd GP | MAC 40/43 | Kjeldsen et al, 2nd Int. Wkshop of MAbs & Breast Cancer, San Fran., Nov. 1986 |
|  | High $M_r$ GP | EMA | Sloane et al., Cancer, 17:1786, 1981 |
|  | High $M_r$ GP | HMFG1 HFMG2 | Arklie et al., Int. J. Cancer, 28:23, 1981 |
|  | NS | 3.15.C3 | Arklie et al., Int. J. Cancer, 28:23, 1981 |
|  | NS | M3, M8, M24 | Foster et al., Virchows Arch. (Pathol. Anat. Histopathol.), 394:295, 1982 |
|  | 1 (Ma) blood group Ags | M18 | Foster et al., HumanPathol., 15:502, 1984 |
|  | NS | 67-D-11 | Rasmussen et al., Breast Cancer Res. Treat., 2:401, 1982 |
|  | oestrogen receptor | D547Sp, D75P3, H222 | Kinsel et al., Cancer Res., 49:1052, 1989 |
|  | EGF Receptor | Anti-EGF | Sainsbury et al, Lancet, 1:364, 1985 |
|  | Laminin Receptor | LR-3 | Horan Hand et al., Cancer Res., 45:2713, 1985 |
|  | erb B-2 p185 | TA1 | Gusterson et al., Br. J. Cancer, 58:453, 1988 |
|  | NS | H59 | Hendler et al., Trans. Assoc. Am. Physicians, 94:217, 1981 |
|  | 126 Kd GP | 10-3D-2 | Soule et al., PNAS, 80:1332, 1983 |
|  | NS | HmAB1,2 | Imam et al., cited in Schlom et al., Adv. Cancer Res., 43:143, 1985 |
|  | NS | MBR 1,2,3 | Menard et al., Cancer Res., 63:1295, 1983 |
|  | 95 Kd | 24.17.1 | Thompson et al., J. Natl. Cancer Inst., 70:409, 1983 |
|  | 100 Kd | 24.17.2 (3E1.2) | Croghan et al., Cancer Res., 43:4980, 1983 |
|  | NS | F36/22.M7/105 | Croghan et al., Cancer Res., 44:1954, 1984 |
|  | 24 Kd | C11, G3, H7 | Adams et al., Cancer Res., 43:6297, 1983 |
|  | 90 Kd GP | B6.2 | Colcher et al., PNAS, 78:3199, 1981 |
|  | CEA & 180 Kd GP | B1.1 | Colcher et al., Cancer Invest., 1:127, 1983 |
|  | colonic & pancreatic mucin similar to Ca 19-9 | Cam 17-1 | Imperial Cancer Research Technology MAb listing |
|  | milk mucin core protein | SM3 | Imiperial Cancer Research Technology Mab listing |

TABLE II-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| | milk mucin core protein | SM4 | Imperial Cancer Research Techology Mab listing |
| | affinity-purified milk mucin | C-Mul (566) | Imperial Cancer Research Technology Mab listing |
| | p185$^{HER2}$ | 4D5 3H4, 7C2, 6E9, 2C4, 7F3, 2H11, 3E8, 5B8, 7D3, 5B8 | Shepard et al., J. Clin. Immnunol., 11(3):117, 1991 |
| | CA 125 >200 Kd GP | OC 125 | Kabawat et al., Int. J. Gynecol. Pathol., 4:245, 1985 |
| | High $M_r$ mucin/ glycolipid | MO v2 | Miotti et al., Cancer Res., 45:826, 1985 |
| | High $M_r$ mucin | DU-PAN-2 | Lan et al., Cancer Res., 44:1954, 1984 |
| | 'gp48' 48 Kd GP | 4F$_7$/7A$_{10}$ | Bhattacharya et al., Cancer Res., 44:4528, 1984 |
| | 300–400 Kd GP | DF$_3$ | Kufe et al., Hybridoma, 3:223, 1984 |
| | 'TAG-72' high $M_r$ mucin | B72-3 | Thor et al., Cancer Res., 46;3118, 1986 |
| | 'CEA' 180 Kd GP | ccccCEA 11 | Wagener et al., Int. J. Cancer, 33:469, 1984 |
| | 'PLAP' 67 Kd GP | H17-E2 | McDicken et al., Br. J. Cancer, 52:59, 1985 |
| | HMFG-2 >400 Kd GP | 3.14.A3 | Burchell et al., J. Imminol., 131:508, 1983 |
| | NS | FO23C5 | Riva et al., Int. J. Cancer, 2:114, 1988 (Suppl.) |
| C: COLORECTAL | | | |
| | TAG-72 High $M_r$ mucin | B72.3 | Colcher et al., Cancer Res., 47:1185 & 4218, 1987 |
| | GP37 | (17-1A) 1083-17-1A | Paul et al., Hybridoma, 5:171, 1986 |
| | Surface GP | CO17-1A | LoBuglio et al., JNCl, 80:932, 1988 |
| | CEA | ZCE-025 | Patt et al., Cancer Bull., 40:218, 1988 |
| | CEA | AB2 | Griffin et al., Proc. 2nd Conf. on Radioimmunodetection & Therapy of Cancer, 82, 1988 |
| | cell surface AG | HT-29-15 | Cohn et al., Arch. Surg. 122:1425, 1987 |
| | secretory epithelium | 250-30.6 | Leydem et al., Cancer, 57:1135, 1986 |
| | surface glycoprotein | 44 × 14 | Gallagher et al., J. Surg. Res., 40:159, 1986 |
| | NS | A7 | Takahashi et al., Cancer, 61:881, 1988 |
| | NS | GA73.3 | Munz et al., J. Nucl, Med., 27:1739, 1986 |
| | NS | 791T/36 | Farrans et al., Lancet, 2:397, 1982 |
| | cell membrane & cytoplasmic Ag | 28A32 | Smith et al., Proc. Am. Soc. Clin. O. col., 6:250, 1987 |
| | CEA & vindesine | 28.19.8 | Corvalen, Cancer Immuno., 24:133, 1987 |
| | gp72 | X MMCO-791 | Byers et al., 2nd Int. Conf. Mab Immmocon. Cancer, 41:1987 |
| | high $M_r$ mucin | DU-PAN-2 | Lan et al., Cancer Res., 45:305, 1985 |
| | high $M_r$ mucin | ID$_3$ | Gangopadhyay et al., Cancer Res., 45:1744, 1985 |
| | CEA 180 Kd GP | CEA 11-H5 | Wagener et al., Int. J. Cancer, 33:469, 1984 |
| | 60 Kd GP | 2C$_8$/2F$_7$ | Bhattacharya et al., Hybridoma, 4:153, 1985 |
| | CA-19-9 (or GICA) | CA-19-9 (1116NS 19-9) | Atkinson et al., Cancer Res., 62:6820, 1982 |
| | Lewis a | PR5C5 | Imperial Cancer Research Technology Mab Listing |
| | Lewis a | PR4D2 | Imperial Cancer Research Technology Mab Listing |
| | colonic mucus | PR4D1 | Imperial Cancer Research Technology Mab Listing |
| D. MELANOMA | | | |
| | p97$^a$ | 4.1 | Woodbury et al., PNAS, 77:2183, 1980 |
| | p97$^a$ | 8.2 M$_{17}$ | Brown, et al., PNAS, 78:539, 1981 |
| | p97$^b$ | 96.5 | Brown, et al., PNAS, 78:539, 1981 |
| | p97$^c$ | 118.1, 133.2, (113.2) | Brown, et al., PNAS, 78:539, 1981 |
| | p97$^c$ | L$_1$, L$_{10}$, R$_{10}$(R$_{19}$) | Brown et al., J. Immunol., 127:539, 1981 |
| | P97$^d$ | I$_{12}$ | Brown et al., J. Immunol., 127:539, 1981 |
| | p97$^e$ | K$_5$ | Brown et al., J. Immunol., 127:539, 1981 |
| | p155 | 6.1 | Loop et al., Int. J. Cancer, 27:775, 1981 |
| | G$_{D3}$ disialogan-glioside | R24 | Dippold et al., PNAS, 77:6115, 1980 |

TABLE II-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| | p210, p60, p250 | 5.1 | Loop et al., Int. J. Cancer, 27:775, 1981 |
| | p280 p440 | 225.28S | Wilson et al., Int. J. Cancer, 28:293, 1981 |
| | 2GP 94, 75, 70 & 25 | 465.12S | Wilson et al., Int. J. Cancer, 28:293, 1981 |
| | P240–P250, P450 | 9.2.27 | Reisfeld et al., Melanoma Ags & Abs, 1982 pp. 317 - |
| | 100, 77, 75 Kd | F11 | Chee et al., Cancer Res., 42:3142, 1982 |
| | 94 Kd | 376.96S | Imai et al., JNCI, 68:761, 1982 |
| | 4 GP chains | 465.12S | Imai et al., JNCI, 68:761, 1982; Wilson et al., Int. J. Cancer, 28:293, 1981 |
| | GP 74 | 15.75 | Johnson & Reithmuller, Hybridoma, 1:381, 1982 |
| | GP 49 | 15.95 | Johnson & Reithmuller, Hybridoma, 1:381, 1982 |
| | 230 Kd | Mel-14 | Carrel et al., Hybridoma, 1:387, 1982 |
| | 92 Kd | Mel-12 | Carrel et al., Hybridoma, 1:387, 1982 |
| | 70 Kd | Me3-TB7 | Carrel et al., Hybridoma, 1:387, 1982 |
| | HMW MAA similar to 9.2.27 AG | 225.28SD | Kantor et al., Hybridoma, 1:473, 1982 |
| | HMW MAA similar to 9.2.27 AG | 763.24TS | Kantor et al., Hybridoma, 1:473, 1982 |
| | GP95 similar to 376.96S 465.12S | 705F6 | Stuhlmiller et al., Hybridoma, 1:447, 1982 |
| | GP125 | 436910 | Saxton et al., Hybridoma, 1:433, 1982 |
| | CD41 | M148 | Imperial Cancer Research Technology Mab listing |
| E: GASTROINTESTINAL | | | |
| pancreas, stomach gall bladder | high $M_r$ mucin | ID$_3$ | Gangopadhyay et al., Cancer Res., 45:1744, 1985 |
| pancreas, stomach | high $M_r$ mucin | DU-PAN-2 | Lan et al., Cancer Res., 45:305, 1985 |
| pancreas | NS | OV-TL3 | Poels et al., J. Natl. Cancer Res., 44:4528, 1984 |
| pancreas, stomach, oesophagus | 'TAG-72' high $M_r$ mucin | B72.3 | Thor et al., Cancer Res., 46:3118, 1986 |
| stomach | 'CEA' 180 Kd GP | CEA 11-H5 | Wagener et al., Int. J. Cancer, 33:469, 1984 |
| pancreas | HMFG-2 >400 Kd GP | 3.14.A3 | Burchell et al., J. Immunol., 131:508, 1983 |
| G.I. | NS | C COLI | Lemkin et al., Proc. Am. Soc. Clin. Oncol., 3:47, 1984 |
| pancreas, stomach | CA 19-9 (or GICA) | CA-19-9 (1116NS 19-9) and CA50 | Szymendera, Tumour Biology, 7:333, 1986 |
| pancreas | CA125 GP | OC125 | Szymendera, Tumour Biology, 7:333, 1986 |
| F: LUNG | | | |
| non-small cell lung carcinoma | p185$^{HER2}$ | 4D5 3H4, 7C2, 6E9, 2C4, 7F3, 2H11, 3E8, 5B8, 7D3, SB8 | Shepard et al., J. Clin. Immunol., 11(3):117, 1991 |
| | high $M_r$ mucin/ glycolipid | MO v2 | Miolti et al., Cancer Res., 65:826, 1985 |
| | 'TAG-72' high $M_r$ mucin | B72.3 | Thor et al., Cancer Res., 46:3118, 1986 |
| | high $M_r$ mucin | DU-PAN-2 | Lan et al., Cancer Res., 45:305, 1985 |
| | 'CEA' 180 kD GP | CEA 11-H5 | Wagener et al, Int. J. Cancer., 33:469, 1984 |
| Malignant Gliomas | cytoplasmic antigen from 85HG-22 cells | MUC 8-22 | Stavrou, Neurosurg. Rev., 13:7, 1990 |
| | cell surface Ag from 85HG-63 cells | MUC 2-63 | Stavrou, Neurosurg. Rev. 13:7, 1990 |
| | cell surface Ag from 86HG-39 cells | MUC 2-39 | Stavrou, Neurosurg. Rev., 13:7, 1990 |
| | cell surface Ag from 86HG-39 cells | MUC 7-39 | Stavrou, Neurosurg. Rev., 13:7, 1990 |
| G: MISCELLANEOUS | | | |
| | p53 | PAb 240 PAb 246 PAb 1801 | Imperial Cancer Research Technology MaB Listing |
| small round cell tumors | neural cell adhesion | ERIC.1 | Imperial Cancer Research Technology MaB Listing |

TABLE II-continued

MARKER ANTIGENS OF SOLID TUMORS AND CORRESPONDING MONOCLONAL ANTIBODIES

| Tumor Site | Antigen Identity/ Characteristics | Monoclonal Antibodies | Reference |
|---|---|---|---|
| | molecule | | |
| medulloblastoma neuroblastoma rhabdomyosarcoma | | M148 | Imperial Cancer Research Technology MaB Listing |
| neuroblastoma | | FMH25 | Imperial Cancer Research Technology MaB Listing |
| renal cancer & glioblastomas | p155 | 6.1 | Loop et al., Int. J. Cancer, 27:775, 1981 |
| bladder & laryngeal cancers | "Ca Aotigen" 350–390 kD | CA1 | Ashall et al., Lancet, July 3, 1, 1982 |
| neuroblastoma | GD2 | 3F8 | Cheung et al., Proc. AACR, 27:318, 1986 |
| Prostate | gp48 48 kD GP | $4F_7/7A_{10}$ | Bhattacharya et al., Cancer Res. 44:4528, 1984 |
| Prostate | 60 kD GP | $2C_3/2F_7$ | Bhattacharya et al., Hybridoma, 4:153, 1985 |
| Thyroid | 'CEA' 180 kD GP | CEA 11-H5 | Wagener et al., Int. J. Cancer, 33:469, 1984 | abbreviations:
Abs, antibodies; Ags, antigens; EGF, epidermal growth factor; GI, gastrointestinal; GICA, gastrointestinal-associated antigen; GP, glycoprotein; GY, gynecological; HMFG, human milk fat globule; Kd, kilodaltons; Mabs, monoclonal antibodies; $M_r$, molecular weight; NS, not specified; PLAP, placental alkaline phosphatase; TAG, tumor-associated glycoprotein; CEA, carcinoembryonic antigen.
footnotes:
the CA 19-9 Ag (GICA) is sialosylfucosyllactotetraosylceramide, also termed sialylated Lewis pentaglycosyl ceramide or sialylated lacto-N-fucopentaose II; p97 Ags are believed to be chondroitin sulphate proteoglycan; antigens reactive with Mab 9.2.27 are believed to be sialylated glycoproteins associated with chondroitin sulphate proteoglycan; unless specified, GY can include cancers of the cervix, endocervix, endometrium, fallopian tube, ovary, vagina or mixed Mullerian tumor; unless specified GI can include cancers of the liver, small intestine, spleen, pancreas, stomach and oesophagus.

Generally speaking, antibodies of the present invention will preferably exhibit properties of high affinity, such as exhibiting a $K_d$ of <200 nM, and preferably, of <100 nM, and will not show significant reactivity with life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The "life-sustaining" tissues that are the most important for the purposes of the present invention, from the standpoint of low reactivity, include heart, kidney, central and peripheral nervous system tissues and liver. The term "significant reactivity", as used herein, refers to an antibody or antibody fragment, which, when applied to the particular tissue under conditions suitable for immunohistochemistry, will elicit either no staining or negligible staining with only a few positive cells scattered among a field of mostly negative cells. Many of the antibodies listed in Table II will not be of sufficient tumor specificity to be of use therapeutically. An example is MUC8-22 which recognizes a cytoplasmic antigen. Antibodies such as these will be of use only in diagnostic or investigational embodiments such as in model systems or screening assays.

Particularly promising antibodies from the stand point of therapeutic application of the present invention are those having high selectivity for the solid tumor, such as B72.3, PR5C5 or PR4D2 for colorectal tumors; HMFG-2, TAG 72, SM-3, or anti-p $185^{Her2}$ for breast tumors; anti-p $185^{Her2}$ for lung tumors; 9.2.27 for melanomas; and MO v18 and OV-TL3 for ovarian tumors.

The listing of potential solid tumor cell surface antigen targets in Table II is intended to be illustrative rather than exhaustive. Of course, in the practice of the invention, one will prefer to ensure in advance that the clinically-targeted tumor expresses the antigen ultimately selected. This is a fairly straightforward assay, involving antigenically testing a tumor tissue sample, for example, a surgical biopsy, or perhaps testing for circulating shed antigen. This can readily be carried out in an immunological screening assay such as an ELISA (enzyme-linked immunosorbent assay), wherein the binding affinity of antibodies from a "bank" of hybridomas are tested for reactivity against the tumor. Antibodies demonstrating appropriate tumor selectivity and affinity are then selected for the preparation of bispecific antibodies of the present invention. Antitumor antibodies will also be useful in the preparation of antitumor antibody conjugates for use in combination regimens, wherein tumor endothelium and the solid tumor itself are both targeted (see, e.g., FIG. 12).

F. PREPARATION OF TARGETING AGENT/ TOXIN COMPOUNDS; INCLUDING IMMUNOTOXINS

Methods for the production of the target agent/toxin agent compounds of the invention are described herein. The targeting agents, such as antibodies, of the invention may be linked, or operatively attached, to the toxins of the invention by either crosslinking or via recombinant DNA techniques, to produce, for example, targeted immunotoxins.

While the preparation of immunotoxins is, in general, well known in the art (see, e.g., U.S. Pat. No. 4,340,535, and EP 44167, both incorporated herein by reference), the inventors are aware that certain advantages may be achieved through the application of certain preferred technology, both in the preparation of the immunotoxins and in their purification for subsequent clinical administration. For example, while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Additionally, while numerous types of disulfide-bond containing linkers are known which can successfully be employed to conjugate the toxin moiety with the targeting agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action. Furthermore, while certain advantages in accordance with the invention will be realized through the use of any of a number of toxin moieties, the inventors have found that the use of ricin A chain, and even more preferably deglycosylated A chain, will provide particular benefits.

A wide variety of cytotoxic agents are known that may be conjugated to anti-endothelial cell antibodies. Examples include numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases such as placental ribonuclease, angiogenic, diphtheria toxin, and *pseudomonas* exotoxin, to name just a few. The most preferred toxin moiety for use in connection with the invention is toxin A chain which has been treated to modify or remove carbohydrate residues, so called deglycosylated A chain. The inventors have had the best success through the use of deglycosylated ricin A chain (dgA) which is now available commercially from Inland Laboratories, Austin, Tex.

However, it may be desirable from a pharmacologic standpoint to employ the smallest molecule possible that nevertheless provides an appropriate biological response. One may thus desire to employ smaller A chain peptides which will provide an adequate anti-cellular response. To this end, it has been discovered by others that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional significant benefits in accordance the invention. In that the cloning and expression of biologically active ricin A chain has now been enabled through the publications of others (O'Hare et al., 1987; Lamb et al., 1985; Halling et al., 1985), it is now possible to identify and prepare smaller or otherwise variant peptides which nevertheless exhibit an appropriate toxin activity. Moreover, the fact that ricin A chain has now been cloned allows the application of site-directed mutagenesis, through which one can readily prepare and screen for A chain derived peptides and obtain additional useful moieties for use in connection with the present invention.

The cross-linking of the toxin A chain region of the conjugate with the targeting agent region is an important aspect of the invention. In certain cases, it is required that a cross-linker which presents disulfide function be utilized for the conjugate to have biological activity. The reason for this is unclear, but is likely due to a need for certain toxin moieties to be readily releasable from the targeting agent once the agent has "delivered" the toxin to the targeted cells. Each type of cross-linker, as well as how the cross-linking is performed, will tend to vary the pharmacodynamics of the resultant conjugate. Ultimately, in cases where a releasable toxin is contemplated, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Cross-linking reagents are used to form molecular bridges that tie together functional groups of two different proteins (e.g., a toxin and a binding agent). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., dgA).

The spacer arm between these two reactive groups of any cross-linkers may have various length and chemical composition. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

The most preferred cross-linking reagent is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a clearable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane (Wawrzynczak & Thorpe, 1987). The use of such cross-linkers is well understood in the art.

Once conjugated, it will be important to purify the conjugate so as to remove contaminants such as unconjugated toxin or targeting agent. It is important to remove unconjugated A chain because of the possibility of increased toxicity. Moreover, it is important to remove unconjugated targeting agent to avoid the possibility of competition for the antigen between conjugated and unconjugated species. In any event, a number of purification techniques are disclosed in the Examples below which have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates (Knowles & Thorpe, 1987). The use of Blue-Sepharose combines the properties of ion exchange with A chain binding to provide good separation of conjugated from unconjugated binding.

The Blue-Sepharose allows the elimination of the free (non conjugated) targeting agent (e.g., the antibody or fragment) from the conjugate preparation. To eliminate the free (unconjugated) toxin (e.g., dgA) a molecular exclusion chromatography step is preferred using either conventional gel filtration procedure or high performance liquid chromatography. One may also use the methods disclosed in U.S. patent application Ser. No. 08/147,768, incorporated herein by reference, which enables the production of immunotoxins bearing one, two or three toxin chains per antibody molecule.

Standard recombinant DNA techniques that are well known to those of skill in the art may be utilized to express nucleic acids encoding the targeting agent/toxin compounds of the invention. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989; and Ausubel et al., 1989).

When produced via recombinant DNA techniques such as those described herein, the targeting agent/toxin compounds of the invention may be referred to herein as "fusion proteins". It is to be understood that such fusion proteins contain at least a targeting agent and a toxin of the invention, operatively attached. The fusion proteins may also include additional peptide sequences, such as peptide spacers which operatively attach the targeting agent and toxin compound, as long as such additional sequences do not appreciably affect the targeting or toxin activities of the fusion protein.

Depending on the specific toxin compound used as part of the fusion protein, it may be necessary to provide a peptide spacer operatively attaching the targeting agent and the toxin compound which is capable of folding into a disulfide-bonded loop structure. Proteolytic cleavage within the loop would then yield a heterodimeric polypeptide wherein the targeting agent and the toxin compound are linked by only a single disulfide bond. See, for example, Lord et al. (1992). An example of such a toxin is a Ricin A-chain toxin.

When certain other toxin compounds are utilized, a non-cleavable peptide spacer may be provided to operatively attach the targeting agent and the toxin compound of the fusion protein. Toxins which may be used in conjunction with non-clearable peptide spacers are those which may, themselves, be converted by proteolytic cleavage, into a cytotoxic disulfide-bonded form (see for example, Ogata et al., 1990). An example of such a toxin compound is a Pseudonomas exotoxin compound.

Nucleic acids that may be utilized herein comprise nucleic acid sequences that encode a targeting agent of interest and nucleic acid sequences that encode a toxin agent of interest. Such target agent-encoding and toxin agent-encoding nucleic acid sequences are attached in a manner such that translation of the nucleic acid yields the targeting agent/toxin compounds of the invention.

Standard techniques, such as those described above may be used to construct expression vectors containing the above-described nucleic acids and appropriate transcriptional/translational control sequences. A variety of host-expression vector systems may be utilized. These include but are not limited to microorganisms such as bacteria (e.g., E. coli, B. subtilis) transformed with recombinant bacteriophage DNA, plasmid DNA or cosmid DNA expression vectors containing targeting agent/toxin coding sequences; yeast (e.g., Saccharomyces, Pichia) transformed with recombinant yeast expression vectors containing targeting agent/toxin coding sequences; insect cell systems infected with recombinant virus expression vectors (e.g., baculovirus) containing the targeting agent/toxin coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the targeting agent/toxin coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems a number of expression vectors may be advantageously selected depending upon the use intended for the targeting agent/toxin compound being expressed. For example, when large quantities of targeting agent/toxin compound are to be produced for the generation of antibodies or to screen peptide libraries, vectors which direct the expression of high levels of fusion protein products that are readily purified may be desirable. Such vectors include but are not limited to the E. coli expression vector pUR278 (Ruther et al., 1983), in which the targeting agent/toxin coding sequence may be ligated individually into the vector in frame with the lac Z coding region so that a fusion protein additionally containing a portion of the lac Z product is provided; pIN vectors (Inouye et al., 1985; Van Heeke et al., 1989); and the like. pGEX vectors may also be used to express foreign polypeptides, such as the targeting agent/toxin compounds as fusion proteins additionally containing glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the targeting agent/toxin protein of the fusion protein can be released from the GST moiety.

In an insect system, Autograph californica nuclear polyhidrosis virus (AcNPV) is used as a vector to express foreign genes. The virus grows in Spodoptera frugiperda cells. The targeting agent/toxin coding sequences may be cloned into non-essential regions (for example the polyhedrin gene) of the virus and placed under control of an AcNPV promoter (for example the polyhedrin promoter). Successful insertion of the targeting agent/toxin coding sequences will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983; Smith U.S. Pat. No. 4,215,051).

In mammalian host cells, a number of viral based expression systems may be utilized. In cases where an adenovirus is used as an expression vector, the targeting agent/toxin coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing targeting agent/toxin proteins in infected hosts (e.g., see Logal et al., 1984). Specific initiation signals may also be required for efficient translation of inserted targeting agent/toxin coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, etc. For long-term, high-yield production of recombinant proteins, stable expression is preferred. For example, cell lines which stably express constructs encoding the targeting agent/toxin compounds may be engineered. Rather than using expression vectors which contain viral origins of replication, host cells can be transformed with targeting agent/toxin DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase (Wigler et al., 1977), hypoxanthineoguanine phosphoriboxyltransferase (Szybalska et ai., 1962), and adenine phsophoribosyltransferase genes (Lowy et al., 1980) can be employed in tk-, hgprt- or aprt-cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colberre-Garapin et al., 1981); and hygro, which confers resistance to hygromycin (Santerre et al., 1984).

After a sufficiently purified compound has been prepared, one will desire to prepare it into a pharmaceutical composition that may be administered parenterally. This is done by using for the last purification step a medium with a suitable pharmaceutical composition.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

A preferred parenteral formulation of the targeting agent/toxin compounds, including immunotoxins, in accordance with the present invention is 0.25 to 2.5 mg conjugate/ml in 0.15M NaCl aqueous solution at pH 7.5 to 9.0. The preparations may be stored frozen at −10° C. to −70° C. for at least 1 year.

G. ATTACHMENT OF OTHER AGENTS TO TARGETING AGENTS

It is contemplated that most therapeutic applications of the present invention will involve the targeting of a toxin moiety to the tumor endothelium. This is due to the much greater ability of most toxins to deliver a cell killing effect as compared to other potential agents. However, there may be circumstances, such as when the target antigen does not internalize by a route consistent with efficient intoxication by targeting agent/toxin compounds, such as immunotoxins, where one will desire to target chemotherapeutic agents such as antitumor drugs, other cytokines, antimetabolites, alkylating agents, hormones, and the like. The advantages of these agents over their non-targeting agent conjugated counterparts is the added selectivity afforded by the targeting agent, such as an antibody. One might mention by way of example agents such as steroids, cytosine arabinoside, methotrexate, aminopterin, anthracyclines, mitomycin C, vinca alkaloids, demecolcine, etoposide, mithramycin, and the like. This list is, of course, merely exemplary in that the technology for attaching pharmaceutical agents to targeting agents, such as antibodies, for specific delivery to tissues is well established (see, e.g., Ghose & Blair, 1987).

It is proposed that particular benefits may be achieved through the application of the invention to tumor imaging. Imaging of the tumor vasculature is believed to provide a major advantage when compared to present imaging techniques, in that the cells are readily accessible. Moreover, the technology for attaching paramagnetic, radioactive and even fluorogenic ions to targeting agents, such as antibodies, is well established. Many of these methods involve the use of a metal chelate complex employing, for example, an organic chelating agent such a DTPA attached to the antibody (see, e.g., U.S. Pat. No. 4,472,509). In the context of the present invention the selected ion is thus targeted to the tumor endothelium by the targeting agent, such as an antibody, allowing imaging to proceed by means of the attached ion.

A variety of chemotherapeutic and other pharmacologic agents have now been successfully conjugated to antibodies and shown to function pharmacologically (see, e.g., Vaickus et al., 1991). Exemplary antineoplastic agents that have been investigated include doxorubicin, daunomycin, methotrexate, vinblastine, and various others (Dillman et al., 1988; Pietersz et al., 1988). Moreover, the attachment of other agents such as neocarzinostatin (Kimura et al., 1983), macromycin (Manabe et al., 1984), trenimon (Ghose, 1982) and α-amanitin (Davis & Preston, 1981) has been described.

In addition to chemotherapeutic agents, the inventors contemplate that the invention will be applicable to the specific delivery of a wide variety of other agents to tumor vasculature. For example, under certain circumstances, one may desire to deliver a coagulant such as Russell's Viper Venom, activated Factor IX, activated Factor X or thrombin to the tumor vasculature. This will result in coagulation of the tumor's blood supply. One can also envisage targeting a cell surface lyric agent such as phospholipase C (Flickinger & Trost, 1976) or cobra venom factor (CVF) (Vogel & Muller-Eberhard, 1981) which should lyse the tumor endothelial cells directly. The operative attachment of such structures to targeting agents, such as antibodies, may be readily accomplished, for example, by protein-protein coupling agents such as SMPT. Moreover, one may desire to target growth factors, other cytokines or even bacterial endotoxin or the lipid A moiety of bacterial endotoxin to a selected cell type, in order, e.g., to achieve modulation of cytokine release. The attachment of such substances is again well within the skill in the art as exemplified by Ghose & Blair (1987).

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent (see preceding section on immunotoxins). In the case of doxorubicin and daunomycin, attachment may be achieved by means of an acid labile acyl hydrazone or cis aconityl linkage between the drug and the antibody. Finally, in the case of methotrexate or aminopterin, attachment is achieved through a peptide spacer such as L—Leu—L—Ala—L—Leu—L—Ala, between the γ-carboxyl group of the drug and an amino acid of the antibody. For a general overview of linking technology, one may wish to refer to Ghose & Blair (1987).

Alternatively, any such structures which are nucleic acid-encoded structures may be operatively attached to the targeting agents of the invention by standard recombinant DNA techniques, such as, for example, those discussed above, in the previous section.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLE I

A Murine Model for Antibody-Directed Targeting of Vascular Endothelial Cells in Solid Tumors This example describes the development of a model system in which to investigate the antibody-directed targeting of vascular endothelial cells in solid tumors in mice. A neuroblastoma transfected with the mouse interferon-γ (IFN-γ) gene, C1300(Muγ), was grown in SCID and antibiotic-treated BALB/c nude mice. The INF-γ secreted by the tumor induces the expression of MHC Class II antigens on the tumor vascular endothelium. Class II antigens are absent from the vasculature of normal tissues, although they are present oh B-lymphocytes, cells of monocyte/macrophage. lineage and some epithelial cells. Intravenously-administered anti-Class II antibody strongly stains the tumor vasculature whereas an anti-tumor antibody, directed against a MHC Class I antigen of the tumor allograft, produces classical perivascular tumor cell staining.

MATERIALS AND METHODS

1. Animals

BALB/c nu/nu mice were purchased from Simonsen (Gilroy, Calif.). SCID mice were from the UT Southwestern Medical Center breeding colony. All animals were maintained in microisolation units on sterilized food and water. Where indicated, tetracycline—HCl (Vedeo, St. Joseph, Mo.) was added to drinking water to a final concentration of 1.1 mg/ml (Harkness et al., 1983). Both strains carry the $H-2^d$ haplotype.

2. Cells and Culture Conditions

All cell lines used in this study were cultured in modified Eagle's medium (MEM) supplemented with 10% (v/v) fetal calf serum, 2.4 mM L-glutamine, 200 units/ml penicillin and 100 μg/ml streptomycin. Cultures were maintained at 37° C. in a humidified atmosphere of 90% air/10 $CO_2$. The C1300 neuroblastoma line was established from a spontaneous tumor which arose in an A/Jax mouse in 1940 (Dunham et al., 1953). The C1300(Muγ)12 line, hereafter abbreviated to C1300 (Muγ), was derived by transfection of C1300 cells with murine IFN-γ gene using the IFN-γ expression retrovirus pSVX (Muγδ$A_s$) (Watanabe et al., 1988; Watanabe et al., 1989), and was cultured in MEM as above containing 1 mg/ml G418 (Geneticin, Sigma). Both lines carry the MHC haplotype $H-2K^k$, $I-A^k$, $I-E^k$, $D^d$. C1300 and C1300(Muγ) cells were grown in regular tissue culture flasks or, when large quantities were required for in vivo studies, in cell factories (Baxter, Grand Prairie, Tex.). Cells from subcutaneous tumors were recovered for in vitro analysis by gentle mincing in MEM. After tumor cells had adhered overnight the monolayers were washed twice with MEM to remove nonadherent contaminant host cells.

Tumor conditioned media were prepared by seeding C1300 and C1300(MuAγ) cells at 25% of confluent density and culturing them for four days. Conditioned media were dialyzed for 16 hours against MEM without FCS to remove G418, filtered through a 0.22 μM membrane and stored at 4° C. for no more than one week before assay. Aliquots of anti-IFN-γ antibodies (see 'Monoclonal Antibodies') sufficient to neutralize 200 international units (I.U.) of murine IFN-γ/ml of conditioned medium were added to some samples 24 hours before assay. The SVEC-10 murine endothelial cell line, hereafter abbreviated to SVEC, was kindly provided to Dr. M. Edidin, Department of Biology, Johns Hopkins University, Baltimore, Md. and was derived by immortalization of lymph node endothelial cells from a C3H ($H-2^k$) mouse with SV40 (O'Connell et al., 1990). For some studies, SVEC cells were cultured for 72 hours with 100 I.U./ml recombinant murine IFN-γ, (r.IFN-γ, a generous gift from Dr. F. Balkwill, Imperial Cancer Research Fund, London, England) or tumor-conditioned medium. In addition, 200 I.U./ml anti-IFN-γ antibody was added to some flasks at the beginning of the 72 hour culture period.

3. Monoclonal Antibodies

The M5/114.15.2 (hereafter abbreviated to M5/114) and 11-4.1 hybridomas were purchased from the American Type Collection (Rockville, Md.) and were grown in MEM-10% FCS. The antibodies were purified from culture supernatant by precipitation in 50% ammonium sulphate and affinity chromatography on Protein A. The rat IgG2b antibody, M5/114, detects an Ia specificity on I-A$^b$, I-A$^q$, I-A$^d$, I-E$^d$ and I-E$^k$ molecules (Bhattacharya etal., 1981). Thus, the antibody recognizes I-E$^k$ molecules on SVEC (H-2$^k$) cells and I-A$^d$ and I-E$^d$, hereafter referred to collectively as Ia$^d$, on cells from BALB/C nu/nu or SCID mice (both H-2$^d$). The anti-Ia$^d$ reactivity of M5/114 was confirmed in this study by FACS analyses with the Ia$^d$ expressing B-lymphoma line, A20/25 (Kim, 1978). The mouse IgG2a antibody 11-4.1 recognizes H-2K$^k$ but not H-2K$^d$ molecules (Oi et al., 1978) and so binds to H-2K$^k$ on C1300 and C1300(Muγ) cells but is unreactive with MHC antigens from BALB/c nu/nu or SCID mice. Isotype-matched control antibodies of irrelevant specificity were CAMPATH-2 (rat IgG2b, anti-human CD7 (Bindon et al., 1988) and WT-1 (mouse IgG2a, anti-human CD7 (Tax et al., 1984). Purified preparations of CAMPATH-2 and WT-1 were generous gifts from Dr. G. Hale (Department of Pathology, Cambridge, England) and Dr. W. Tax (Sint Radboudzeikenhuis, Nijmegen, the Netherlands) respectively.

Rat anti-mouse endothelial cell antibody MECA-20 (Duijvestijn et al., 1987) was donated as a concentrated culture supernatant by Dr. A. Duijvestijn (University of Limburg, the Netherlands) and used at a dilution of 1/200 for indirect immunoperoxidase staining. Rat antibodies against mouse macrophages (M1) and mouse CD3 (KT 31.1) were generously provided by Dr. P. Beverley (Imperial Cancer Research Fund, London, England). Hamster anti-mouse IFN-γ antibody 1222-00 (Sanchez-Madrid, 1983), used for specific neutralization of IFN-γ in vitro, was purchased from Genzyme (Boston, Mass.). Anti-mouse IFN-γ antibodies, XMG1.2 and R46A2, used in IFN-γ ELISAs, were kindly provided by Dr. N. Street (U.T. Southwestern Medical Center, Dallas, Tex.). Purified 11-4.1, WT-1 and XMG1.2 antibodies were biotinylated by incubation with a 12.5 fold molar excess of N-hydroxysuccinimidobiotin amidocaproate (Sigma) for one hour at room temperature followed by dialysis against two changes of PBS.

4. ELISA for murine IFN-γ

Sandwich ELISAs for murine IFN-γ were carried out as described by (Cherwinski et al., 1989). The wells of flexible PVC microtiter plates (Dynatech, Alexandria, Va.) were coated with 50 μl/well of a 2 μg/ml solution of capture anti-iFN-γ antibody, R46A2, in PBS for 2 hours at room temperature. Non-specific protein binding sites were blocked with 20% FCS in PBS for 15 minutes at 37° C. The plates were washed three times in PBS containing 0.05% (v/v) Tween 20 (Sigma) (PBS-T) and 25 μl/well control and test samples in MEM-10% FCS were added. After incubating for 1 hour at 37° C., the wells were washed as before and 50 μl/well of a 1 μg/ml solution of biotinylated anti-IFN-γ antibody XMG1.2 in PBS-T containing 1% BSA were added. After incubation for 30 minutes at 37° C. the wells were washed as before and incubated with 75 μl of a 1:2000 dilution of horseradish peroxidase-conjugated streptavidin (DAKO) for one hour at room temperature. After thorough washing in PBS-T the wells were incubated for 30 minutes with 100 μl/well of a 1 mg/ml solution of 2,2'-azino-bis-(3-ethylbenzthiazoline-6-sulfonic acid) (ABTS, Sigma) in citrate/phosphate buffer containing 0.003% (v/v) $H_2O_2$. Reaction product was measured as Abs.405 nm–Abs.490 nm. IFN-γ levels in test samples were calculated by reference to a recombinant murine IFN-γ standard solution in MEM-10% FCS.

5. Indirect Immunofluorescence

SVEC, C1300 and C1300(Muγ) cells were prepared for FACS analyses as described by Burrows et al. (1991). All manipulations were carried out at room temperature. 50 μl of a cell suspension at 2–3×10$^6$ cells/ml in PBS containing 0.2% (w/v) BSA and 0.2% (w/v) NaN$_3$ (PBS-BSA-N$_3$) were added to the wells of round-bottomed 96-well microtiter plates (Falcon 3910). Optimal dilutions of rat or mouse antibodies were distributed in 50 μl volumes, and the plates sealed. After 15 minutes, the cells were washed four times by centrifuging the plates at 800×g for 30 seconds, removing the supernatants, and resuspending the cells in 150 μl/well PBS-BSA-N3. Fluorescein isothiocyanate-conjugated rabbit antibodies against rat or mouse IgG (ICN, High Wycombe, England), diluted 1:20 in PBS-BSA-N$_3$ were distributed in 50 μl volumes into the appropriate wells. The cells were incubated for a further 15 minutes and washed as before. Cell-associated fluorescence was measured on a FACScan (Becton Dickenson, Fullerton, Calif.). Data were analyzed using the CONSORT 30 program.

6. Preparation of Tissues and Immunohistochemistry

For the establishment of solid tumors, a total of 2×10$^7$ C1300 or C1300(Muγ) cells, or a mixture of the two, in 200 μl MEM-30% FCS were injected subcutaneously into the right anterior flank of BALB/c nu/nu or SCID mice. Tumor diameters were measured at regular intervals and the animals were euthanized after 16 days (rapidly-growing tumors) or 20 days (slowly-growing tumors). Tumors and normal tissues were excised immediately and snap-frozen over liquid nitrogen. Normal tissues were also harvested from non-tumor-bearing animals. Antibody localization studies were performed in animals bearing 1 cm subcutaneous tumors induced by injection of C1300 and C1300 (Muγ) in the ratio 7:3. One hundred micrograms of unconjugated M5/114 or CAMPATE-2 antibodies or 100 μg biotinylated 11-4.1 or WT-1 antibodies in 100 μl PBS were injected intravenously. At various times thereafter the animals were euthanized and their circulation was flushed with PBS for 5 minutes before removal and freezing of tumors and normal tissues as before. 8 μM frozen sections were cut on a Tissuetek 2 cryostat (Baxter) and air-dried for 2 hours at room temperature. Slides were stored at −20° C. for up to 3 months before assay.

Indirect immunoperoxidase staining for rat IgG was adapted from a method described by Billington et al. (1986). Sections were allowed to return to room temperature, air dried for 30 minutes and fixed in acetone for 15 minutes. After rehydration in PBS for 5 minutes, sections were incubated in a humidified chamber for 45–60 minutes with primary antibodies, diluted optimally in PBS-0.2% BSA, (PBS-BSA). After two washes in PBS, the sections were incubated for 30–45 minutes with horseradish peroxidase-conjugated rabbit anti-mouse IgG (Dakopatts, Carpinteria, Calif.) diluted 1:10 in PBS-BSA supplemented with 20% normal mouse serum (ICN, High Wycombe, UK) to block antibodies cross-reacting with mouse immunoglobulins. After a further two washes in PBS, the reaction product was developed using 0.5 mg/ml 3',3'- diaminobenzidine (Sigma) containing 0.01% (v/v) hydrogen peroxide for 8 minutes. The sections were counterstained with Mayer's hematoxylin (Sigma) for 15 seconds, dehydrated in absolute ethanol, cleared in xylene and mounted with Accumount 60 medium (Baxter). Indirect immunoperoxidase staining with biotinylated mouse antibodies was carried out in the same manner, except that peroxidase-conjugated streptavidin-biotin complex, diluted 1:50 in PBS with no blocking serum, was used as the second layer.

B. RESULTS

1. Murine IFN-γ levels in C1300(Mu7) conditioned-medium

C1300(Muγ)-conditioned medium contained 50.2–63.5 I.U./ml murine IFN-γ, in accordance with previous reports (Watanabe et al., 1989). By contrast, less than 5 I.U./ml IFN-γ was detected in C1300-conditioned medium or C1300 (Muγ)-conditioned medium to which an excess of neutralizing anti-IFN-γ antibody had been added 24 hours before assay.

Figure 1B:
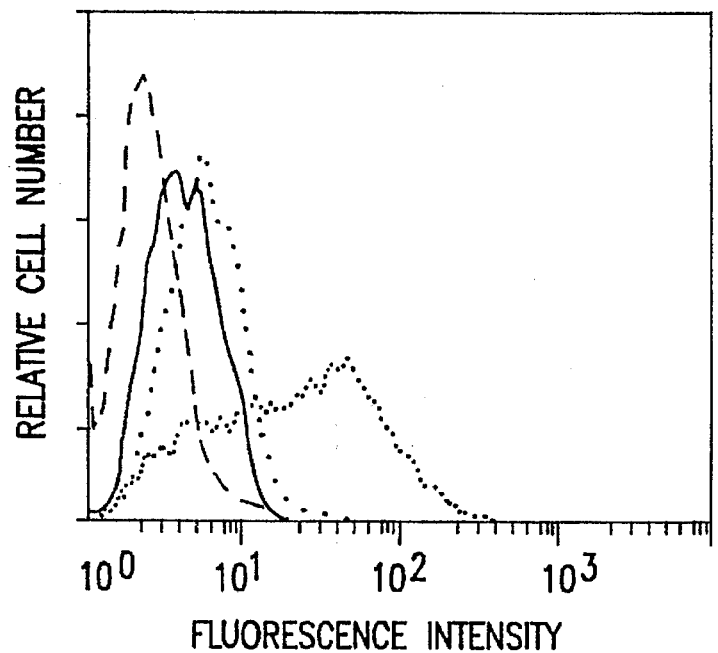
FIG. 1b. Induction of I-E$^k$ on SVEC cells by IFN-γ in C1300-conditioned media. SVEC cells were cultured for 72 hours in C1300-conditioned medium ( . . . ), C1300(Muγ)-conditioned medium ( . . . ) or C1300(Muγ)-conditioned medium plus excess neutralizing anti-IFN-γ antibody ( . . . ). Their expression of I-E$^k$ was then measured as in FIG. 1a. Other cultures were treated with C1300(Muγ)-conditioned medium and stained with an isotype-matched control antibody ( - - - ).

2. Induction of MHC Class IU (I-E$^k$) on SVEC cells by r.IFN-γ in C1300 (Muγ) -conditioned-medium As shown in FIG. 1a, unstimulated SVEC cells did not express I-E$^k$. By contrast, a large majority of cells preincubated with r.IFN-γ (FIG. 1a) or with C1300(Muγ)-conditioned medium (FIG. 1b) expressed significant levels of I-E$^k$, and this induction was almost completely blocked by anti-IFN-γ. Treatment of SVEC cells with r.IFN-γ or C1300 (Muγ)-conditioned medium did not cause non-specific antibody binding since the isotype-matched control antibody did not bind to the cells. These results were confirmed by indirect immunoperoxidase staining of cytospin preparations.

These findings suggested that vascular endothelial cells in tumors containing sufficient quantities of IFN-γ-secreting C1300(Muγ) cells should be induced to express high cell surface levels of MHC Class II molecules.

Figure 2A:
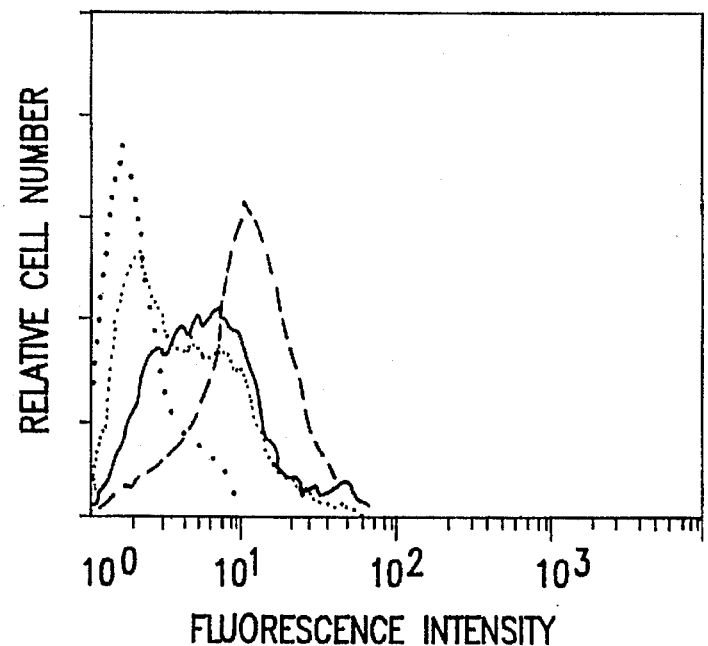
FIG. 2a. Expression of I-E$^k$ and H-2K$^k$ by pure and mixed populations of C1300 and C1300(Muγ) cells stained with anti-I-E$^k$ antibody. C1300 cells ( . . . ), C1300(Muγ) cells (- - -), a mixture of C1300 and C1300(Muγ) cells in the ratio 7:3 cocultured in vitro ( . . . ) or cells recovered from a mixed subcutaneous tumor in a BALB/c nu/nu mouse ( . . . ) were stained with anti-I-E$^k$ antibody by indirect immunofluorescence using the FACS. No staining of any tumor cell population was seen with the isotype-matched control antibodies.

3. Expression of MHC Class I (H-2K$^k$) and Class II (I-E$^k$) by C1300 and C1300(Muγ) cells Since IFN-γ can induce MHC Class II antigen expression in diverse cell types (Capobianchi et al. 1985; Collins et al., 1984; Hokland et al., 1988) and since the M5/114 antibody crossreacts with I-E$^k$, we determined whether the M5/114 antibody —intended for use to target tumor endothelial cells in vivo—would also bind to the tumor cells themselves. As shown in FIG. 2a, C1300(Muγ) cells expressed I-E$^k$, but at levels 10–20 fold lower than those on SVEC cells stimulated with IFN-γ.

Figure 2B:
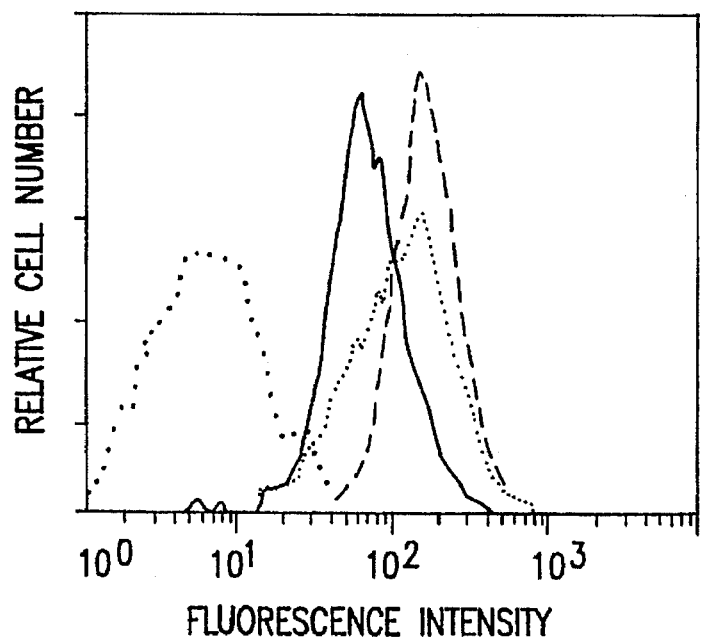
FIG. 2b. Expression of I-E$^k$ and H-2K$^k$ by pure and mixed populations of C1300 and C1300(Muγ) cells stained with anti-H-2K$^k$ antibody. C1300 cells ( . . . ), C1300(Muγ) cells (- - -), a mixture of C1300 and C1300(Muγ) cells in the ratio 7:3 cocultured in vitro ( . . . ) or cells recovered from a mixed subcutaneous tumor in a BALB/c nu/nu mouse ( - - - ) were stained with anti-H-2K$^k$ antibody by indirect immunofluorescence using the FACS. No staining of any tumor cell population was seen with the isotype-matched control antibodies.

Similarly, C1300 cells expressed detectable but low levels of H-2K$^k$ whereas C1300(Muγ) cells displayed uniformly high levels, approximately 20-fold greater than on the parental line (FIG. 2b). This result was expected from the known autocrine Class I-inducing activity of IFN-γ and is in keeping with a previous report (Watanabe et al., 1989). Coculture of C1300(Muγ) cells and C1300 cells induced homogeneous expression of I-Ek and H-2Kk on both populations (FIG. 2). Induction of these antigens on C1300 cells appears to be caused by IFN-γ released into the culture medium by the C1300(Muγ) cells since the effect was centralized by anti-IFN-γ antibodies.

4. Growth of C1300 and C1300 (MuT) tumors in immunodeficient mice and induction of Iad on tumor vascular endothelial cells The inventors first attempted to grow subcutaneous C1300(Muγ) tumors in BALB/c nu/nu and SCID mice because both strains carry the MHC haplotype (H-2$^d$) with which the anti-MHC Class II antibody M5/114 reacts, and because neither strain would be expected to reject the tumors, as do syngeneic immunocompetent A/J animals (Watanabe et al., 1989). For unknown reasons inocula composed entirely of C1300(Muγ) cells failed to produce progressively-growing tumors in BALB/c nu/nu or SCID mice. Conversely, pure C1300 inocula displayed 100% tumorigenicity but, as expected, did not contain Ia$^d$-positive endothelial cells.

Figure 3:
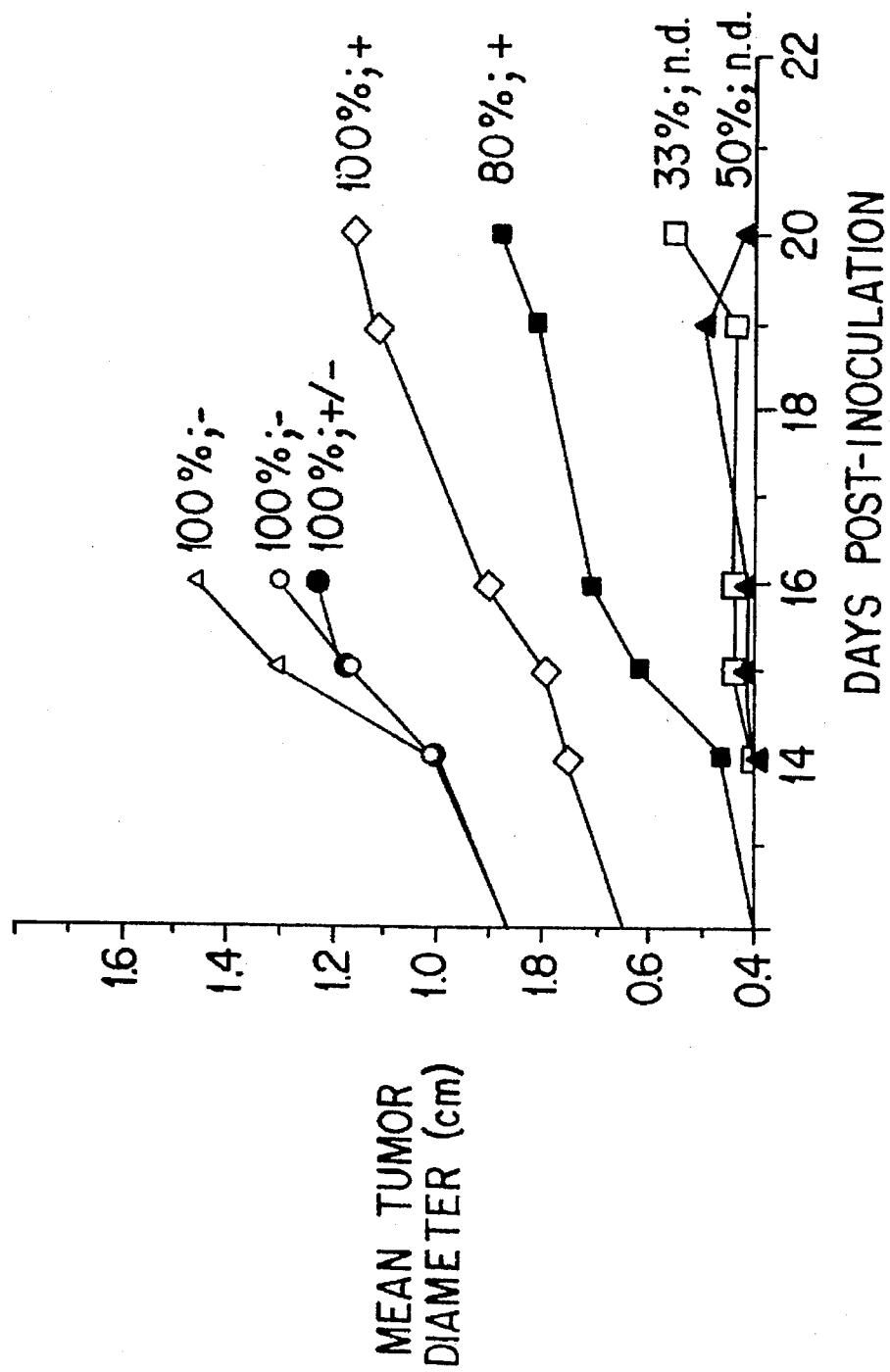
FIG. 3. Tumorigenicity, growth, and tumor endothelial cell Ia$^d$ expression in pure and mixed subcutaneous C1300 and C1300(Muγ) tumors. BALB/c nu/nu mice were injected with a total of 2×10$^7$ tumor cells in which the ratios of C1300: C1300(Muγ) cells were 10:0 (△), 9:1 (○), 8:2 (●), 7:3 (◇), 5:5 (■) 3:7 (□) or 0:10 (▲). The vertical axis shows the mean diameter of the tumors at various times after injection. Also shown are the percentage of animals in each group which developed tumors. The proportion of Ia$^d$-positive vascular endothelial cells was categorized as follows: +, 75–100%; ±, 25–75%; −, 0–5%; n.d., not determined because no intact blood vessels were visible. Standard deviations were <15% of mean diameters and are not shown.

In order to identify a combination which would yield a high percentage of tumor takes, reliable growth kinetics and cause Ia$^d$ induction of a large majority of intratumoral endothelial cells, several ratios of C1300 and C1300(Muγ) cells were inoculated into BALB/c nu/nu mice. As shown in FIG. 3, mixtures containing C1300 and C1300(Muγ) cells in the ratio 9:1 produced rapidly-growing tumors but, when sections of the tumors were stained with anti-Ia$^d$ antibody by the indirect immunoperoxidase technique, none of the endothelial cells in the tumor were found to be stained. Dropping the ratio of C1300: C1300(Muγ) to 8:2 gave rapidly-growing tumors in which approximately 50% of blood vessels were Ia$^d$-positive. Dropping the ratio further to 7:3 or 5:5 produced tumors which grew quite rapidly and contained a large majority of Ia$^d$-positive vessels. Dropping the ratio still further to 3:7 produced tumors in no more than half of the animals and those tumors that became palpable failed to grow beyond 6 mm in diameter. Histological analyses of the latter revealed no morphologically recognizable intact blood vessels and, hence, it was not possible to ascertain their level of Ia$^d$ expression.

Of the two usable C1300: C1300(Muγ) ratios identified, 7:3 and 5:5, the ratio of 7:3 was adopted for the remainder of this study because the take rate was higher (100% vs. 80%) and the variability in tumor growth rate between individual animals was lower.

5. Distribution of Iad in BALB/c nude and SCID mice

The distribution of M5/114 binding in tissues from tumor-bearing BALB/c nu/nu mice is shown in Table III. In subcutaneous tumors, most or all vascular endothelial cells and numerous interstitial macrophages were stained. In most organs, the binding of M5/114 reflected the classical distribution of MHC Class II antigens, being restricted to B cells in lymphoid organs, resident macrophages in all tissues studied except brain and to tissue-specific elements of the reticuloendothelial system, such as liver Kupffer cells and Langerhans cells of the skin. In addition, staining was occasionally seen in some kidney tubules. When sections of small and large intestine from BALB/c nu/nu mice were examined, heavy labeling of both epithelial and endothelial cells was seen in both regions. By contrast, very little staining with M5/114 was seen in sections of intestine from SCID mice maintained in germ-free conditions. The staining of nu/nu mouse intestine was found to be related to the microbiological status of the animals and is discussed below. Apart from in the gut, no staining of endothelial cells with M5/114 was seen in any tissues examined in either nu/nu or SCID mice. The distribution of Iad antigens in normal tissues was not affected by the presence of the tumor because the staining pattern of M5/114 was identical in non-tumor-bearing mice.

in vivo localization of anti-Ia$^d$ antibody in tumor and normal tissues is shown in Table III. Anti-Ia$^d$ antibody was found on the luminal membrane and in the cytoplasm of most or all tumor vascular endothelial cells one hour after injection. A similar pattern was seen at four hours after injection, but by

TABLE III

Localization of Intravenously Administered anti-Ia$^d$ Antibody in C1300 (MUγ) Tumor-Bearing Mice.[a]

| Tissue | Antigen Expression | Localization in vivo | | |
|---|---|---|---|---|
| | | 1 hour | 4 hours | 24 hours |
| Tumor[b] | Endothelial cells (EC), Mφ | EC[c] | EC | EC[d] |
| Brain | None | None | None | None |
| Colon[e] | Minority of epithelium & EC, Mφ | None | None | None |
| Duodenum | Some epithelial cells & EC, Mφ | None | None | None |
| Heart | Interstitial Mφ | None | None | None |
| Kidney | Occasional proximal tubule, Mφ | None | None | None |
| Liver | Kupffer cells (KC), numerous Mφ in parenchyma | KC[c] | KC | KC[d] some Mφ |
| Lung | Numerous Mφ in parenchyma | None | None | None |
| Pancreas | Numerous Mφ in parenchyma | None | None | None |
| Skin[e] | Langerhans cells | None | None | None |
| Spleen | Red pulp (RP) Mφ, marginal zone (MZ) B cells & Mφ, some T/B cells in PALS | MZ PALS | MZ PALS | MZ, RP PALS |

[a] Studies performed with SCID or antibiotic-treated BALB/c nu/nu mice.
[b] Mixed tumor of 7:3 C1300:C1300 (MUγ) cells grown subcutaneously.
[c] Strong staining, including discernable labelling of luminal membranes.
[d] Weaker staining, entirely intracellular.
[e] Either adjacent to, or distant from tumor.
PALS: Periarteriolar lymphatic sheath, Mφ: Macrophages

6. Attenuation of expression of Iad on colonic endothelium and epithelium of nude mice by administration of antibiotics In BALB/c nu/nu mice, most epithelial cells from all regions of the gut were intensely stained with anti-Ia$^d$ antibody. In addition, some endothelial cells in both upper and lower bowel bound M5/114 antibody, particularly those associated with colonic villi. When the animals were treated with oral tetracycline-Hcl, a broad-spectrum antibiotic, for 1–3 weeks there was a progressive diminution of Iad expression in the colon and elsewhere in the gut, so that binding of M5/114 was in most sections restricted to the luminal membranes of a minority of epithelial cells. Light cytoplasmic staining of occasional endothelial cells was observed in some antibiotic-treated animals. The pattern of epithelial and endothelial Ia$^d$ expression was not homogeneous and the intensity of M5/114 staining correlated with the frequency of CD3+T lymphocytes in the adjacent lamina propria. Antibiotic treatment was associated with a dramatic decrease in the numbers of intravillous CD3-positive cells: after three weeks practically all had disappeared from the underlying parenchyma and associated lymphoid deposits and there was a coincident decline in Iad expression on surrounding epithelial and endothelial cells.

In SCID mice, epithelial and endothelial cell Ia$^d$ expression and T-cell infiltration of the colon resembled that of antibiotic-treated BALB/c nu/nu animals.

7. Specific localization of intravenously administered anti-Ia$^d$ antibody to tumor vasculature, B cells and macrophages in SCID and antibiotic-treated nude mice Tumor-bearing BALB/c nu/nu and SCID mice were given intravenous injections of anti-Ia$^d$ or the isotype-matched control antibody and euthanized 1, 4 or 24 hours later. The 24 hours the labeling of tumor endothelial cells was weaker and entirely intracellular, consistent with the progressive internalization and metabolism of the antibody by endothelial cells (Table III). Also, at 24 hours small amounts of antibody were detectable in the immediate perivascular regions of the tumor.

Anti-Ia$^d$ antibody was bound to Kupffer cells in the intravascular compartment of the liver within one hour of injection. At later times after injection, internalization and degradation of the antibody was apparent (Table III). Adjacent sinusoidal endothelial cells were not stained. The high permeability of hepatic fenestrated endothelia was indicated by the penetrance of the antibody to reach some hepatic parenchymal macrophages (Table III). In the spleen, perivascular B cells and macrophages in white pulp marginal zones were stained within one hour, showing that the vasculature of this organ was particularly permeable to antibody. At later stages the antibody penetrated throughout the splenic lymphoid compartment and also labelled a minority of red pulp macrophages (Table III). In organs other than the liver and spleen, macrophages and related cells such as the Langerhans cells of the skin were unstained probably because their vascular endothelium contains tight junctions and is relatively impermeable to antibodies.

Anti-Ia$^d$ antibody was bound to some endothelial cells in the colon of BALB/c nu/nu mice, but not elsewhere in the intestine, one hour after injection. Antibiotic treatment for 1–3 weeks before injection of anti-Ia$^d$ antibody completely abolished localization to gut endothelial cells. No intravenously injected anti-Ia$^d$ antibody homed to gut endothelia in SCID mice. The isotype-matched control antibody was not detected in tumor or normal tissues at any time after injection.

Taken together, these results strongly indicate that, when injected into appropriate tumor-bearing animals anti-Ia$^d$ antibody or immunoconjugates will localize effectively to most or all tumor endothelial cells while sparing life-sustaining normal tissues.

8. Perivascular staining of tumor cells in mice injected with anti-tumor (H-2K$^k$) antibody When frozen sections of subcutaneous tumors deriving from inocula of mixed C1300 and C1300(Muγ) cells (7:3) were stained with biotinylated anti-H-2K$^k$ antibody, a homogeneous staining pattern was obtained. The levels of IFN-γ secreted by the C1300(Muγ) cells in the tumor were therefore sufficient to induce increased H-2K$^k$ expression by the C1300 component of the tumor, in accordance with the in vitro co-culture studies described above. The staining was specific because no staining was seen with the isotype-matched control antibody. No specific labeling of any normal tissue by anti-H-2K$^k$ antibody was found, as expected since this antibody was raised in an H-2$^d$ mouse strain.

In contrast with the rapid binding of intravenously-administered anti-Ia$^d$ antibody to tumor vasculature, no significant accumulation of anti-H-2K$^k$ antibody was apparent one hour after injection. After four hours, however, anti-H-2K$^k$ antibody was detected in small islands of tumor cells surrounding central capillaries. After 24 hours, the antibody was bound to larger discrete areas of tumor cells but staining intensity was diminished relative to the earlier time points. Each with localization times of up to 72 hours, homogenous labeling of all tumor cells was not achieved.

No localization of anti-H-2K$^k$ antibody was found in any normal tissues and binding of the isotype-matched control antibody was not detectable in tumor or normal tissues.

C. DISCUSSION

This example describes a murine model for studying the antibody-directed targeting of vascular endothelial cells in solid tumors. In this model, IFN-γ gene-transfected tumor cells growing in SCID or antibiotic-treated nude mice release IFN-γ which induces the de novo expression of MHC Class II antigens on the tumor vasculature. MHC Class II is absent from the vasculature in the normal tissues of these mice and hence the Class II induced on the tumor vascular endothelial cells serves as a specific marker. Class II is present on B-lymphocytes, Kupffer cells and other cells of monocyte/macrophage lineage but these cells are not life-sustaining so their temporary absence after targeting with cytotoxic immunoconjugates should be tolerable. IFN-γ also induces the tumor cells themselves to express high levels of the MHC Class I antigen, H-2K$^k$, which can serve as a tumor cell-specific marker in BALB/c nu/nu or SCID mice, which both carry the H-2K$^d$ haplotype. Thus, anti-Ia$^d$ and anti-H-2K$^k$ antibodies injected systemically localize selectively to tumor vascular endothelial cells and tumor cells respectively, which enables the approaches of targeting the tumor vasculature and the tumor cells to be compared in this model, or used in combination.

It was necessary to dilute the C1300 (Muγ) cells with C1300 parental cells in the ratio 3:7 to establish progressively-growing subcutaneous tumors in which the vascular endothelial cells were Class II (Ia$^d$)—positive. Undiluted C1300 (Muγ) cells were poorly tumorigenic in BALB/c nu/nu mice, in contrast with a prior report (Watanabe et al., 1989). Vascular dysfunction appeared to be the reason why pure C1300 (Muγ) tumors would not grow beyond a diameter of 5–6 mm. Staining of sections of tumors with the anti-endothelial cell antibody MECA 20 revealed that the vessels were morphologically atypical with no visible lumens. It is possible that excessively high intratumoral IFN-γ levels in pure C1300(Muγ) tumors caused direct vascular toxicity or activated macrophages in the tumor to become cytotoxic for endothelial cells (Peri et al., 1990).

Intravenously injected anti-Ia$^d$ antibody bound rapidly and homogeneously to vascular endothelial cells in the tumor, confirming the immediate accessibility of intravascular targets (Kennel et al., 1991). Remarkably, the inductive influence of IFN-γ from C1300(Muγ) cells was completely restricted to the tumor mass: endothelial cells in the overlying area of skin expressed no detectable Ia$^d$ and did not bind any intravenously-injected anti-Ia$^d$ antibody. It is likely that IFN-γ entering the systemic circulation is neutralized by a specific binding protein, perhaps a soluble form of the IFN-γ receptor (Novick et al., 1989), whose normal role may be to down-regulate cytokine activity (Fernandez-Botran et al., 1991) or to restrict it to the immediate locale of secretion.

Ia$^d$ antigens are not restricted solely to tumor endothelial cells. MHC Class II antigens are expressed constitutively by B cells, activated T cells and cells of the monocyte/macrophage lineage in humans and rodents (Daar et al., 1984; Hämmerling et al, 1976) and were found in this study also to be present on occasional proximal tubules in the kidney and on some epithelial cells in the intestine of SCID and antibiotic-treated BALB/c nu/nu mice. However, when injected intravenously, only the hepatic Kupffer cells, splenic B cells and macrophages in the liver and spleen bound detectable amounts of the anti-Ia$^d$ antibody: the potentially life-sustaining Class II—positive renal and gut epithelial cells were unstained. Localization of intravenously-injected anti-Ia$^d$ antibody to hepatic Kupffer cells and splenic marginal zone B cells occurred within one hour, in accordance with the report of Kennel et al. (1991). Presumably, the extreme permeability of the discontinuous splenic endothelium permits rapid extravasation of antibodies into the parenchyma of this organ and staining of the marginal zone B-cells (Kennel et al., 1991).

The reason for the lack of staining of renal and gut epithelial cells is probably that these cells are not readily accessible to intravenously-administered antibody because the antibody would have to diffuse across basement membranes and several tissue layers to reach these cells. In addition, it is likely that all the remaining anti-Ia$^d$ antibody in the circulation was absorbed by more accessible splenic white pulp lymphocytes before significant extravasation into the red pulp (Kennel et al., 1991; Fujimori et al., 1989) or other normal tissues could occur. This is important because it illustrates a potentially critical pharmacokinetic difference between vascular targeting and tumor cell targeting. Because the tumor endothelial cells are so accessible to intravenously-administered antibody, the presence of a large 'sink' of competing antigen in the blood or lymphoid organs should not prevent the antibody from reaching the target cells but should protect antigen-positive cells in most extravascular compartments. It is conceivable that an antibody recognizing a tumor vascular endothelial cell antigen that is shared by epithelial cells, for instance, might be targeted without the toxic side-effects which have complicated therapy with anti-tumor cell immunoconjugates (Spitler, 1988). Furthermore, even in the absence of such a sink, it is possible that operative specificity for tumor endothelial cells could be achieved in the face of cross-reactivity with extravascular normal tissues by decreasing the dose or by using rapidly-cleared antibody fragments in the construction of the immunoconjugate.

Although anti-Ia$^d$ antibody did not localize to life-sustaining Ia$^d$+ extravascular tissues such as kidney tubules and gut epithelium, it did bind to colonic endothelial cells in non-antibiotic-treated BALB/c nu/nu mice. These cells were as accessible as tumor endothelial cells and were required for survival since regular BALB/c nu/nu mice treated with high doses of M5/114 immunotoxins died from intestinal damage. Murine endothelial cells do not express MMC Class II antigens in vitro (O'Connell et al., 1990; Duijvestijn et al., 1986) or in vivo (de Waal et al., 1983) unless stimulated with IFN-γ so it is likely that induction of Ia$^d$ on intestinal endothelial and epithelial cells was a result of local secretion of IFN-γ by helper T cells (Cherwinski, 1987) or activated NK cells (Anegon, 1988; Kasahara, 1983) in response to gut flora. In accordance with this view, numerous CD3+, CD8+ T cells were observed in the villous stroma and their frequency correlated with the intensity of staining of endothelial and epithelial cells with anti-Ia$^d$ antibody. Furthermore, oral administration of tetracycline-Hcl (a broad spectrum antibiotic) reversed T cell infiltration, diminished Ia$^d$ expression and abolished localization of intravenously-injected anti-Ia$^d$ antibody to colonic endothelial cells.

Antibiotic treatment had no effect on Ia$^d$ expression by tumor endothelial cells. In subsequent studies it was found that SCID mice had little Ia$^d$ on colonic epithelial or endothelial cells and that intravenously-administered anti-Ia$^d$ antibody did not localize to their colonic endothelium. Furthermore, high doses of M5/114 immunotoxins were non-toxic in these animals. Given the possibility of antibiotic resistance arising in the gut flora of tetracycline-treated BALB/c nu/nu mice, we believe that SCID mice may be more suitable for these types of studies.

Consistent with the findings of others (Baxter et al., 1991; Kennel et al., 1991; Jones et al., 1988; Pervez et al., 1988), an anti-tumor antibody directed against the H-2K$^k$ antigen on C1300 and C1300Muγ cells showed perivascular staining of tumor cells after intravenous administration. In view of the homogeneous expression of H-2K$^k$ by tumor cells in vitro and in sections of subcutaneous tumors, it is likely that the uneven intratumoral distribution of intravenously-injected anti-H-2K$^k$ antibody was related to the vascular and interstitial physiology of the tumor (Jain, 1990; Fujimori et al., 1989). This nicely demonstrates, in a single system, the limitations of using antitumor antibodies for targeting and the virtues of tumor vascular targeting. It may be possible to combine both approaches to advantage because the tumor cells that survive destruction of intratumoral blood vessels are likely to be those at the periphery of the tumor mass, close to the tumor-host interface. These areas are likely to be well vascularized by capillaries in adjacent normal tissues and have low interstitial pressure (jain, 1990), so the surviving cells should be amenable to attack by antitumor immunoconjugates.

In summary, the inventors describe a murine model with which to test the feasibility of targeting the vasculature of solid tumors. The model permits the antitumor effects of immunoconjugates directed against tumor vasculature to be compared with those of immunoconjugates directed against the tumor cells themselves.

EXAMPLE II

Solid Tumor Therapy Using A Vascular Targeted Immunotoxin

This example describes the successful therapy of the solid tumor model described in Example I, using the anti-tumor endothelial cell immunotoxin, MS/114dgA, and the anti-tumor cell immunotoxin, 11-4.1dgA, alone as well as in combination therapy.

A. MATERIALS AND METHODS

1. Animals

BALB/c nu/nu mice were purchased from Simonsen (Gilroy, Calif.). SCID mice were from the National Cancer Institute (Bethesda, Md.). Germ-free SCID mice were from the University of Wisconsin (Madison, Wis.). All animals were maintained in microisolation units on sterilized food and water.

2. Cells and Culture Conditions

All cell lines used in this study were cultured in modified Eagle's medium (MEM) supplemented with 10% (v/v) fetal calf serum, 2.4 mM L-glutamine, 200 units/ml penicillin and 100 µg/ml streptomycin. Cultures were maintained at 37° C. in a humidified atmosphere of 90% air/10% $CO_2$. The C1300 neuroblastoma line was established from a spontaneous tumor which arose in an A/jax mouse in 1940 (Dunham et al., 1953). The C1300(Muγ)12 line, hereafter abbreviated to C1300 (Muγ), was derived by transfection of C1300 cells with murine IFN-γ gene using the IFN-γ expression retrovirus PSVX (MuγδA$_s$) (Watanabe et al., 1988), and was cultured in MEM as above containing 1 mg/ml G418 (Geneticin, Sigma). Both lines carry the MHC haplotype H-2K$^k$, I-A$^k$, I-E$^k$, D$^d$. C1300 and C1300(Muγ) cells were grown in regular tissue culture flasks or, when large quantities were required for in vivo studies in cell factories (Baxter, Grand Prairie, Tex.). Cells from subcutaneous tumors were recovered for in vitro analysis by gentle mincing in MEM. After tumor cells had adhered overnight the monolayers were washed twice with MEM to remove non-adherent contaminant host cells.

Tumor conditioned media were prepared by seeding C1300 and C1300(MuAγ) cells at 25% of confluent density and culturing them for four days. Conditioned media were dialyzed for 16 hours against MEM without FCS to remove G418, filtered through a 0.22 µM membrane and stored at 4° C. for no more than one week before assay. Aliquots of anti-IFN-γ antibodies (see 'Monoclonal Antibodies') sufficient to neutralize 200 international units (I.U.) of murine IFN-γ/ml of conditioned medium were added to some samples 24 hours before assay. The SVEC-10 murine endothelial cell line, hereafter abbreviated to SVEC, was kindly provided to Dr. M. Edidin, Department of Biology, Johns Hopkins University, Baltimore, Md. and was derived by immortalization of lymph node endothelial cells from a C3H (H-2$^k$) mouse with SV40 (O'Connell et al., 1990). For some studies, SVEC cells were cultured for 72 hours with 100 I.U./ml recombinant murine IFN-γ, (r.IFN-γ, obtained from Dr. F. Balkwill, Imperial Cancer Research Fund, London, England) or tumor-conditioned medium. In addition, 200 I.U./ml anti-IFN-γ antibody was added to some flasks at the beginning of the 72 hour culture period.

3. Monoclonal Antibodies

The M5/114.15.2 (hereafter abbreviated to M5/114) and 11-4.1 hybridomas were purchased from the American Type Collection (Rockville, Md.) and were grown in MEM-10% FCS. The antibodies were purified from culture supernatant by precipitation in 50% ammonium sulphate and affinity chromatography on Protein A. The rat IgG2b antibody, M5/114, detects an Ia specificity on I-A$^b$, I-A$^q$, I-A$^d$, I-E$^d$ and I-E$^k$ molecules (Bhattacharya et al., 1981). Thus, the antibody recognizes I-E$^k$ molecules on SVEC (H-2$^k$) cells and I-A$^d$ and I-E$^d$, hereafter referred to collectively as Ia$^d$, on cells from BALB/C nu/nu or SCID mice (both H-2d). The mouse IgG2a antibody 11-4.1 recognizes H-2K$^k$ but not H-2K$^d$ molecules (Oi et al., 1978) and so binds to H-2K$^k$ on C1300 and C1300 (Muγ) cells but is unreactive with MHC antigens from BALB/c nu/nu or SCID mice. Isotype-matched control antibodies of irrelevant specificity were CAMPATH-2 (rat IgG2b, anti-human CD7 (Bindon, 1988) and WT-1 (mouse IgG2a, anti-human CD7 (Tax et al., 1984). Purified preparations of CAMPATH-2 and WT-1 were obtained from Dr. G. Hale (Department of Pathology, Cambridge, England) and Dr. W. Tax (Sint Radboudzeikenhuis, Nijmegen, the Netherlands) respectively.

4. Preparation of dgA

The ricin A chain was purified by the method of Fulton et al. (Fulton et al., 1986). Deglycosylated ricin A was prepared as described by Thorpe et al. (1985). For conjugation with antibodies, the A chain was reduced with 5 Mm DTT and subsequently separated from DTT by gel filtration on a column of Sephadex G-25 in PBS, pH 7.5.

5. Preparation of Immunotoxins

IgG immunotoxins were prepared using the 4-succinimidyloxycarbonyl-αmethyl(1-pyridyldithio) toluene linking agent described by Thorpe et al. (1987). 4-succinimidyloxycarbonyl-α-methyl(2-pyridyldithio) toluene dissolved in dimethylformamide was added to the antibody solution (7.5 mg/ml in borate buffer, pH 9.0) to give a final concentration of 0.11 Mm. After 1 hour the derivatized protein was separated from unreacted material by gel chromatography on a Sephadex G-25 column and mixed with freshly reduced ricin A chain. The solution was concentration to about 3 mg/ml and allowed to react for 3 days. Residual thiol groups were inactivated by treating the immunotoxin with 0.2 Mm cysteine for 6 hours. The solution was then filtered through a Sephacryl S-200 HR column in 0.1M phosphate buffer, pH 7.5, to remove unreacted ricin A, cysteine, and aggregates. Finally, the immunotoxin was separated from free antibody by chromatography on a Blue Sepharose CL-6B column equilibrated in 0.1M sodium phosphate buffer, pH 7.5, according to the method of Knowles and Thorpe (1987).

6. Cytotoxicity Assays

C1300, C1300(Muγ) and SVEC cells suspended at $10^5$ cells/ml in MEM-10% FCS were distributed in 100 μl volumes into the wells of flat-bottomed microtiter plates. For some assays, SVEC cells were suspended in C1300- or C1300(Muτ)-conditioned medium or MEM supplemented with 100 I.U./ml r. IFN-τ as indicated. Immunotoxins in the same medium were added (100 μl/well) and the plates were incubated for 24 hours at 37° C. in an atmosphere of 10% $CO_2$ in humidified air. After 24 hours, the cells were pulsed with 2.5 μCi/well [$^3$H] leucine for another 24 hours. The cells were then harvested onto glass fiber filters using a Titertek harvester and the radioactivity on the filters was measured using a liquid scintillation spectrometer (LKB; Rackbeta). The percentage of reduction in [$^3$H] leucine incorporation, as compared with untreated control cultures, was used as the assessment of killing.

7. Antitumor Studies

For the establishment of solid tumors, a mixture of $1.4 \times 10^7$ C1300 cells and $6 \times 10^6$ C1300(Muγ) cells in 200 μl MEM-30% FCS were injected subcutaneously into the right anterior flank of BALB/c nu/nu or SCID mice. Fourteen days later, when the tumors had grown to 0.8–1.2 cm in diameter, the mice were separated into groups of 5–10 animals and injected intravenously with 200 μl of immunotoxins, antibodies or diluent. Perpendicular tumor diameters were measured at regular intervals and tumor volumes were estimated according to the following equation (Steel, 1977).

$$\text{volume} = \text{Smaller diameter}^2 \times \text{larger diameter} \times \pi$$

For histopathological analyses, animals were euthanized at various times after treatment and the tumors were excised immediately into 4% (v/v) formalin. Paraffin sections were cut and stained with hematoxylin and eosin or Massons trichrome.

B. RESULTS

Figure 4A:
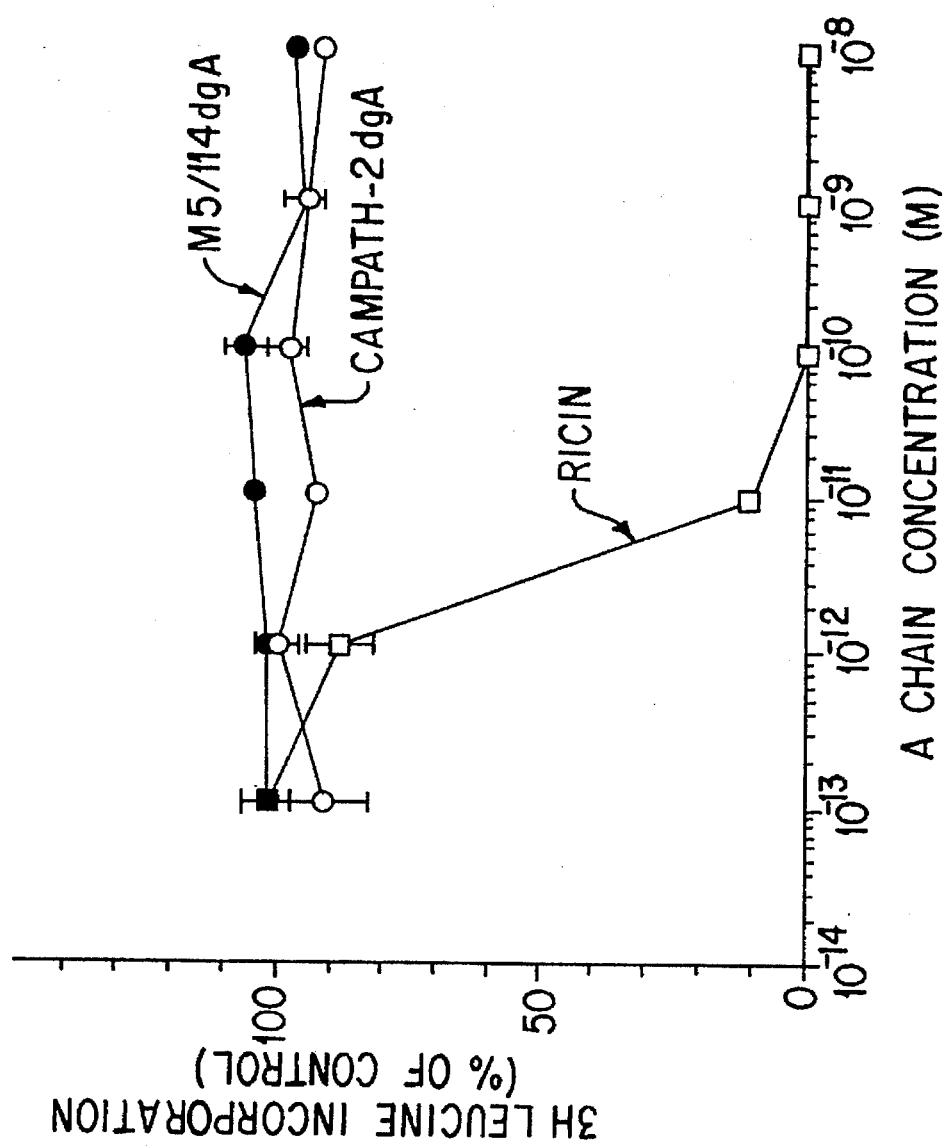
FIG. 4a. Killing activity of anti-Class II immunotoxin (M5/114 dgA) against unstimulated SVEC mouse endothelial cells. The data shown are for treatment of cells with varying concentrations of ricin (□); M5/114dgA (●); and the control immunotoxin CAMPATH-2dgA (○).
Figure 4B:
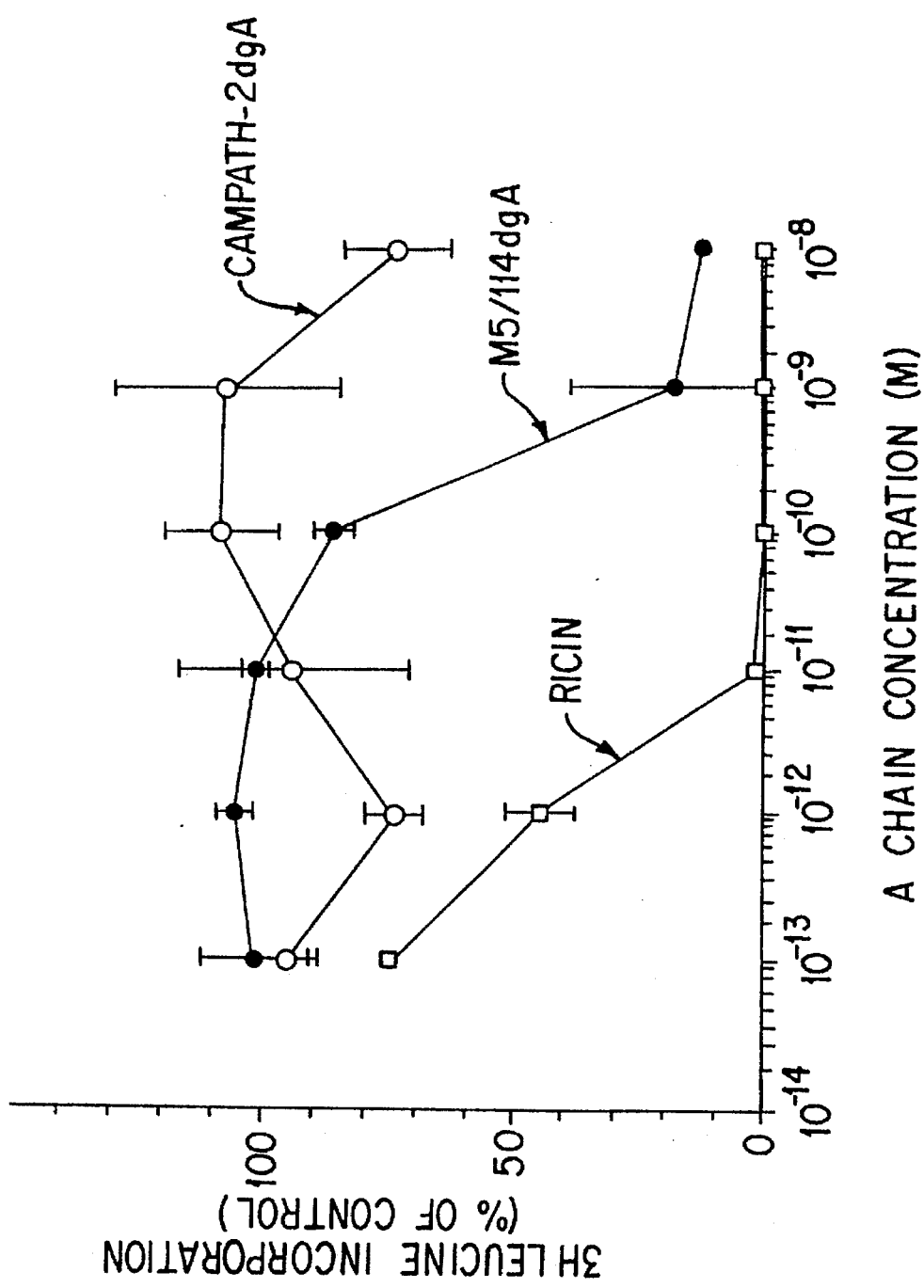
FIG. 4b. Killing activity of anti-Class II immunotoxin (M5/114 dgA) against SVEC mouse endothelial cells stimulated with conditioned medium from the IFN-γ-secreting tumor C1300(Mu-γ). The data shown are for treatment of cells with varying concentrations of ricin (□); M5/114dgA (●); and the control immunotoxin CAMPATH-2dgA (○).

The first studies carried out involved a comparison of killing activity of anti-Class II immunotoxin (M5/114 dgA) against unstimulated SVEC mouse endothelial cells with those stimulated with conditioned medium from IFN-γ-secreting tumor cells (C1300 Muγ). These studies were carried out in order to demonstrate that the anti-Class II immunotoxin, M5/114 dgA exerts a selective toxicity against IFN-γ stimulated endothelial cells, and not against unstimulated cells. The results are shown in FIGS. 4a and b. In FIG. 4a, SVEC mouse endothelial cells were cultured in regular medium and the cultured cells subjected to varying immunotoxin concentrations as indicated. As will be appreciated, while ricin effected a 50% inhibition of leucine incorporation at about $3 \times 10^{-11}$, neither the anti-Class II immunotoxin (M5/114 dgA) nor the control immunotoxin (CAMPATH-2 dgA) exerted a significant toxic effect within the concentration ranges tested. In contrast, when the SVEC mouse endothelial cells were stimulated by culturing in the presence of C1300(Muγ)-conditioned medium, the mouse endothelial cells became quite sensitive to the anti-Class II immunotoxin, with 50% of stimulated cells being killed by the anti-Class II immunotoxin at a concentration of about $3 \times 10^{-10}$M. Thus, these studies demonstrate that γ interferon, which is produced by the C1300(Muγ) and present in the conditioned media effectively promote the appearance of Class II targets on the surface of the SVEC cells.

Figure 5:
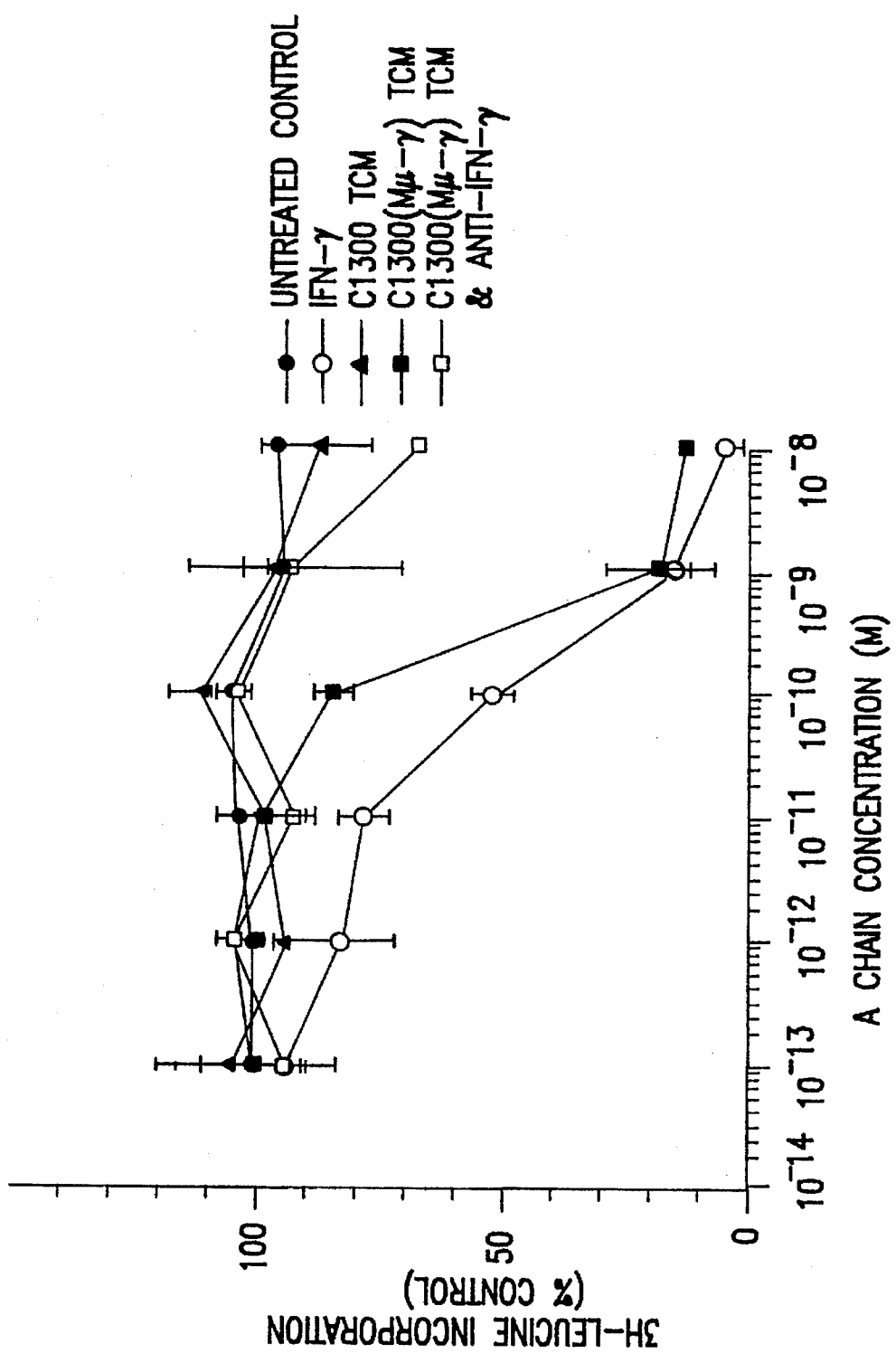
FIG. 5. This figure also shows the killing of SVEC cells under various conditions by the anti-Class II immunotoxin, M5/114dgA. The data shown are for treatment of cells with varying concentrations of the immunotoxin following treatment with IFN-γTCM (○); C1300TCM (▲); C1300(Mu-γ) TCM (■); and C1300(Mu-γ) treated with anti-IFN-γ (□).

FIG. 5 illustrates similar studies, which confirm the finding that the C1300(Muγ) conditioned media effectively promotes the expression of Class II molecules on endothelial cells. In particular, the data shown in FIG. 5 demonstrate that both recombinant IFN-γ as well as conditioned media from C1300(Muγ) sensitize endothelial cells to the anti-tumor endothelial cell immunotoxin, M5/114 dgA. FIG. 5 also demonstrates that conditioned media from C1300 cells that do not secrete interferon (C1300 TCM), as well as interferon-producing C1300 cells (Muγ) pretreated with anti-IFN-γ, both do not promote an anti-Class II immunotoxin sensitizing effect.

Figure 6A:
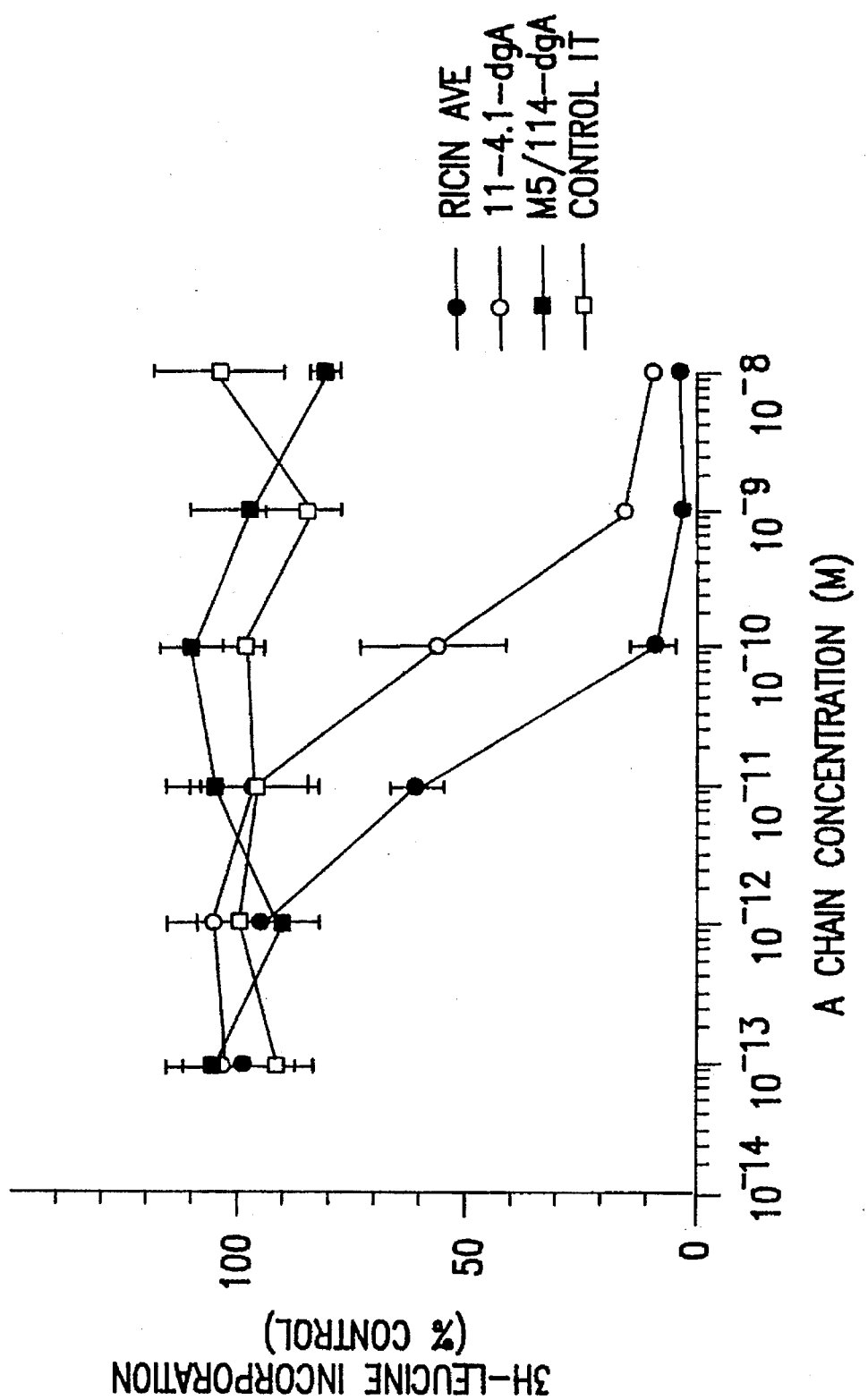
FIG. 6a. Shows a comparison of killing activity of an anti-Class I (antitumor) immunotoxin (11-4.1-dgA, which recognized H-2K$^k$) and an anti-Class II (anti-tumor endothelial cell) immunotoxin (M5/114-dgA) against a 70:30 mixed population of C1300 and C1300(Mu-γ) cells. Data was obtained through treatment of the cells with ricin (●); the 11-4.1-dgA immunotoxin (○); the M5/114-dgA immunotoxin (■) and a control immunotoxin (□).
Figure 6B:
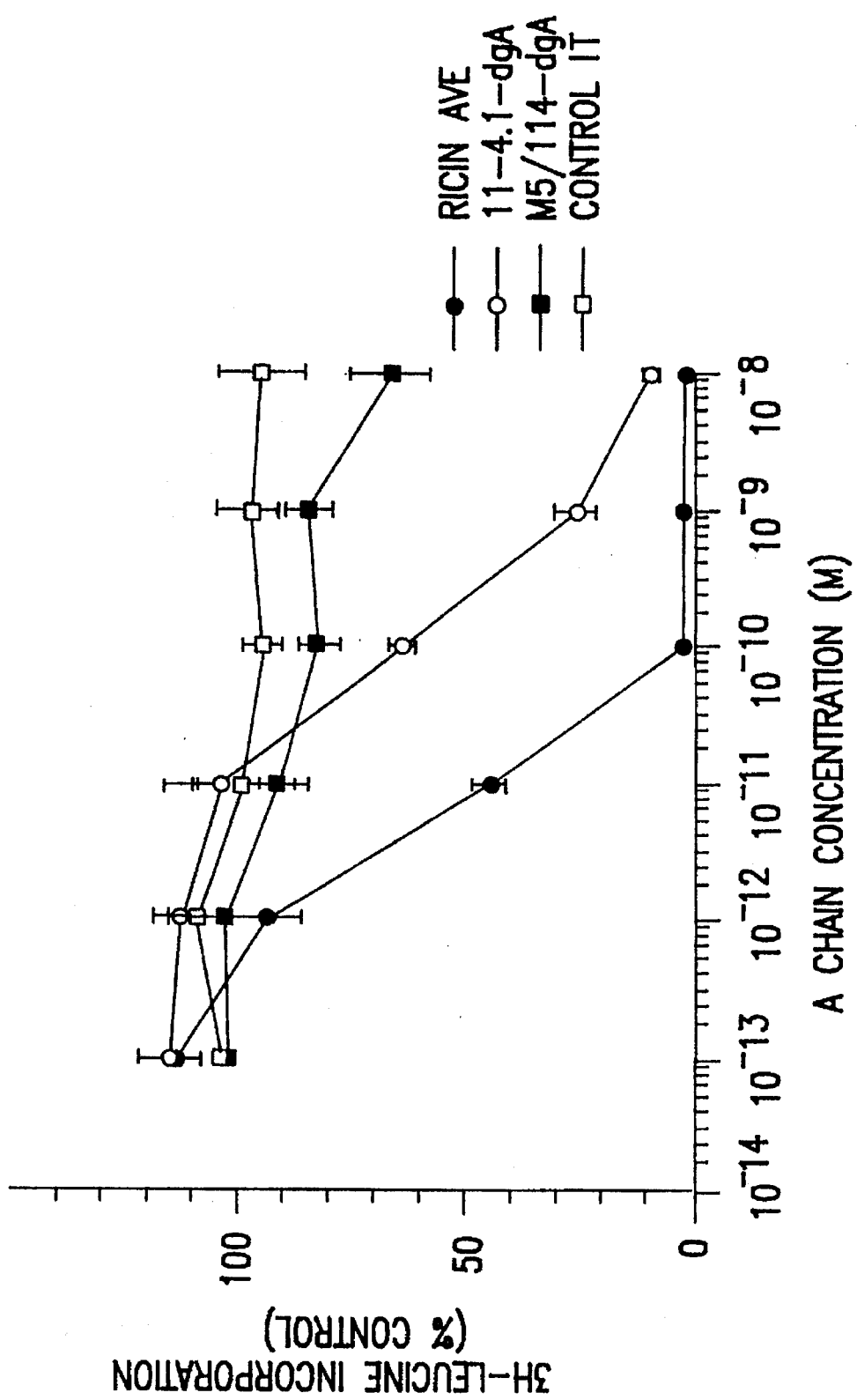
FIG. 6b. Shows killing of cells freshly recovered from subcutaneous tumors in mice. Data was obtained through treatment of the cells with ricin (●); the 11-4.1-dgA immunotoxin (○); the M5/114-dgA immunotoxin (■) and a control immunotoxin (□).

Next, a series of studies were carried out wherein the killing activity of an anti-Class I (anti-tumor) immunotoxin (11-4.1-dgA) and that of the anti-Class II immunotoxin (M5/114-dgA) are compared against a 70:30 mixed population of C1300 and C1300(Muγ) cells. FIG. 6a simply demonstrates that in a 70:30 culture of C1300 and C1300 (Muγ), that only the anti-Class I immunotoxin, 11-4.1-dgA, and ricin, exert a cytotoxic effect. FIG. 6b shows killing of cells freshly recovered from subcutaneous tumors in mice.

Taken together, these Figures demonstrate that the anti-tumor immunotoxin kills tumor cells well, but that the anti-tumor endothelial cell immunotoxin does not. Thus, any anti-tumor effect of M5/114-dgA would not likely be due to direct tumor cell killing. Therefore, these studies serve as a control for later studies wherein it is demonstrated that M5/114-dgA can have a profound anti-tumor effect in the solid tumor model system described in Example I, through an anti vascular effect.

Figure 7A:
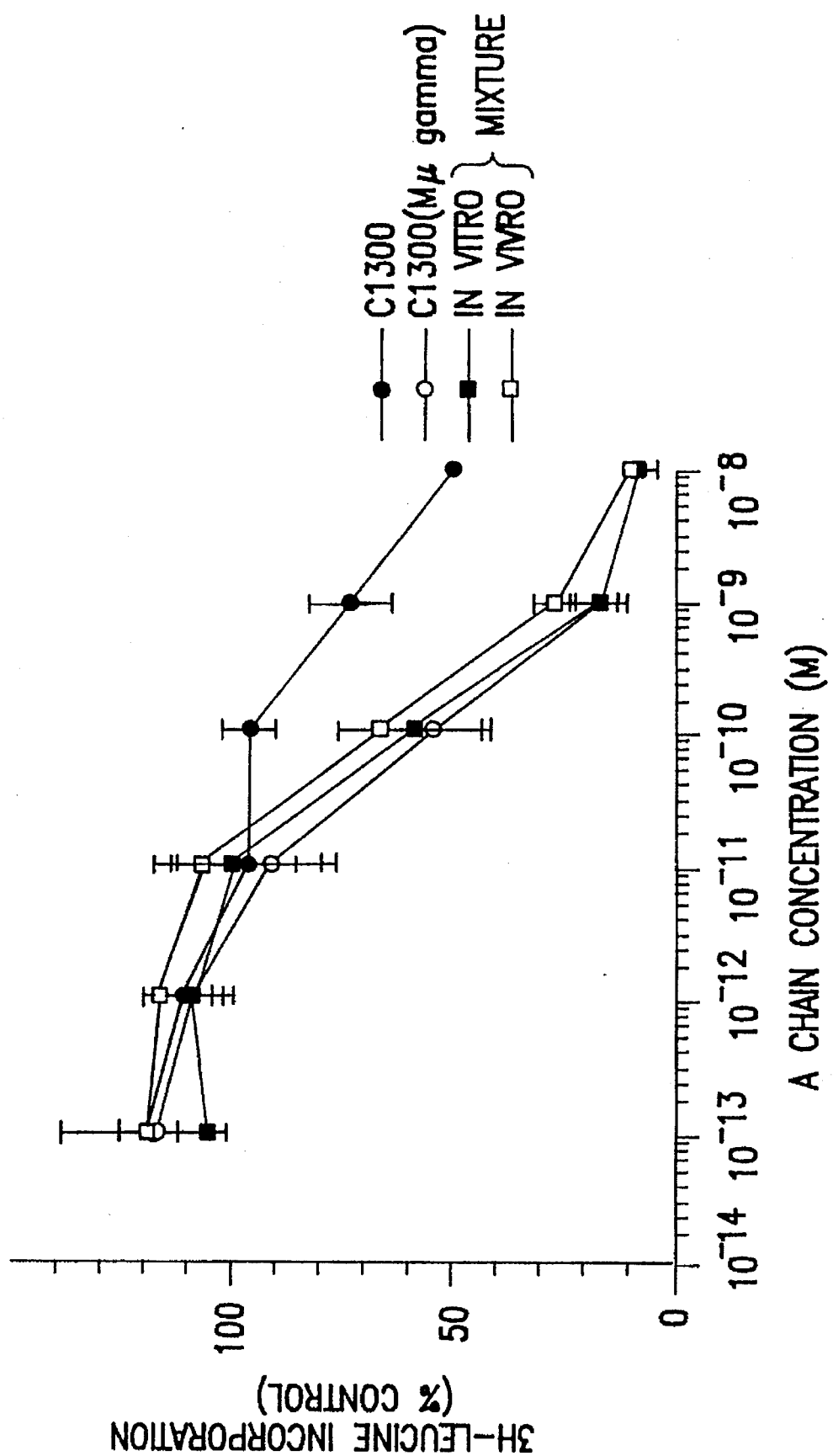
FIG. 7a. Killing of pure populations of C1300 (●) and C1300(Mu-γ) (○) by the antitumor cell immunotoxin, 11-4.1-dgA. Also shown are 70:30 mixed populations mixed in vitro or in vivo (i.e., recovered from S/C tumors). Also shown are controls, including ricin (▲) and a control immunotoxin (△).
Figure 7B:
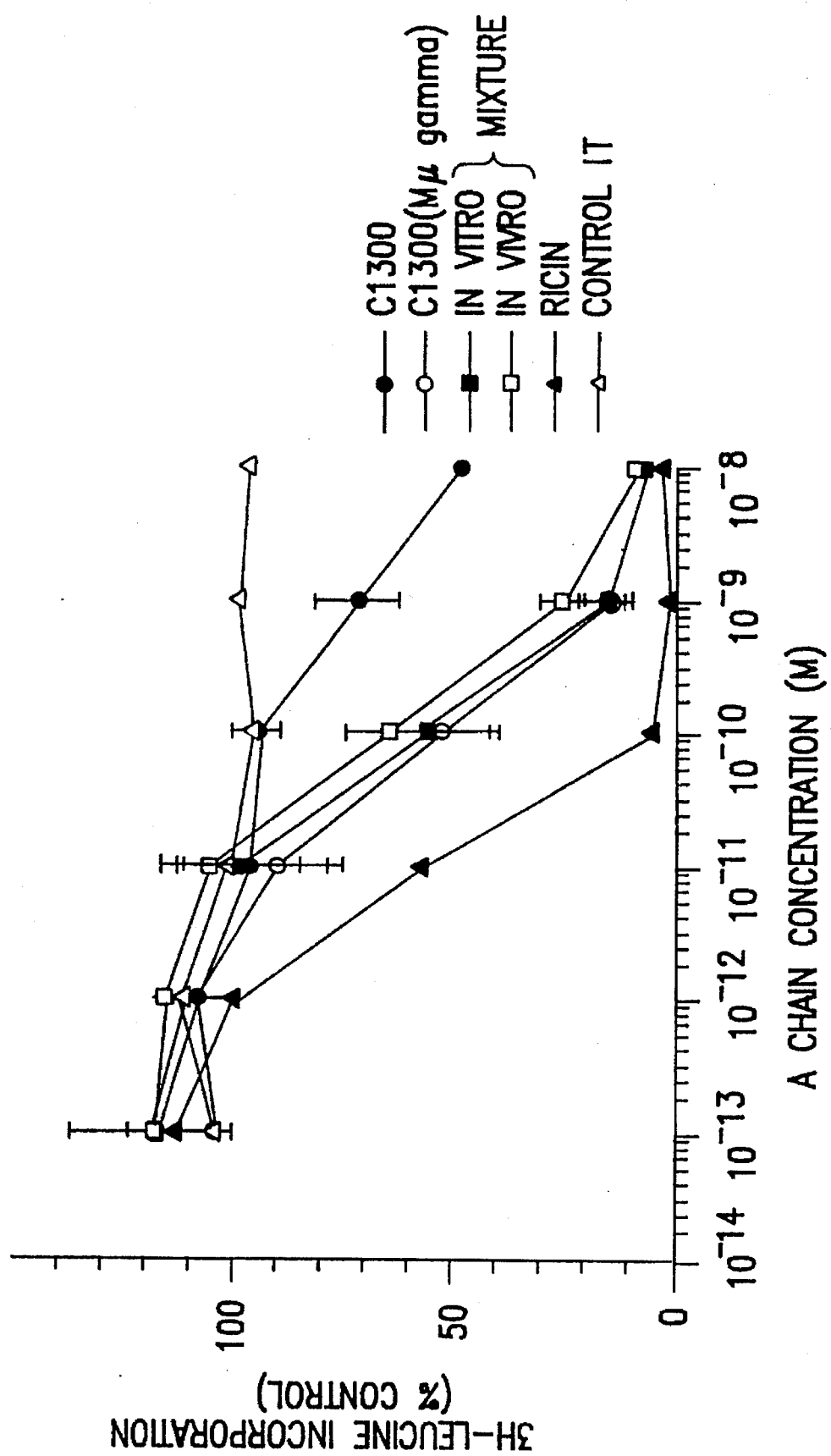
FIG. 7b. Killing of pure populations of C1300 (●) and C1300(Mu-γ) (○) by the antitumor cell immunotoxin, 11-4.1-dgA, as shown in FIG. 7a, with the controls, ricin (▲) and a control immunotoxin (△), for comparison.

FIG. 7 also shows a comparison of killing of pure and mixed populations of C1300 and C1300(Muγ) by the anti-tumor cell immunotoxin 11-4.1 dgA (anti-H-2K$^k$). Both Figures show the effects of the anti-tumor cell immunotoxin against four different tumor populations. Again, in each case the anti-tumor cell immunotoxin demonstrate significant anti-tumor activity, at a concentration of on the order of about $10^{-10}$M. Thus, these data show that mixed tumors should be highly sensitive to the anti-tumor immunotoxin, a control that is needed in order to demonstrate the anti-vascular attributes of the anti-Class II immunotoxin.

Figure 8:
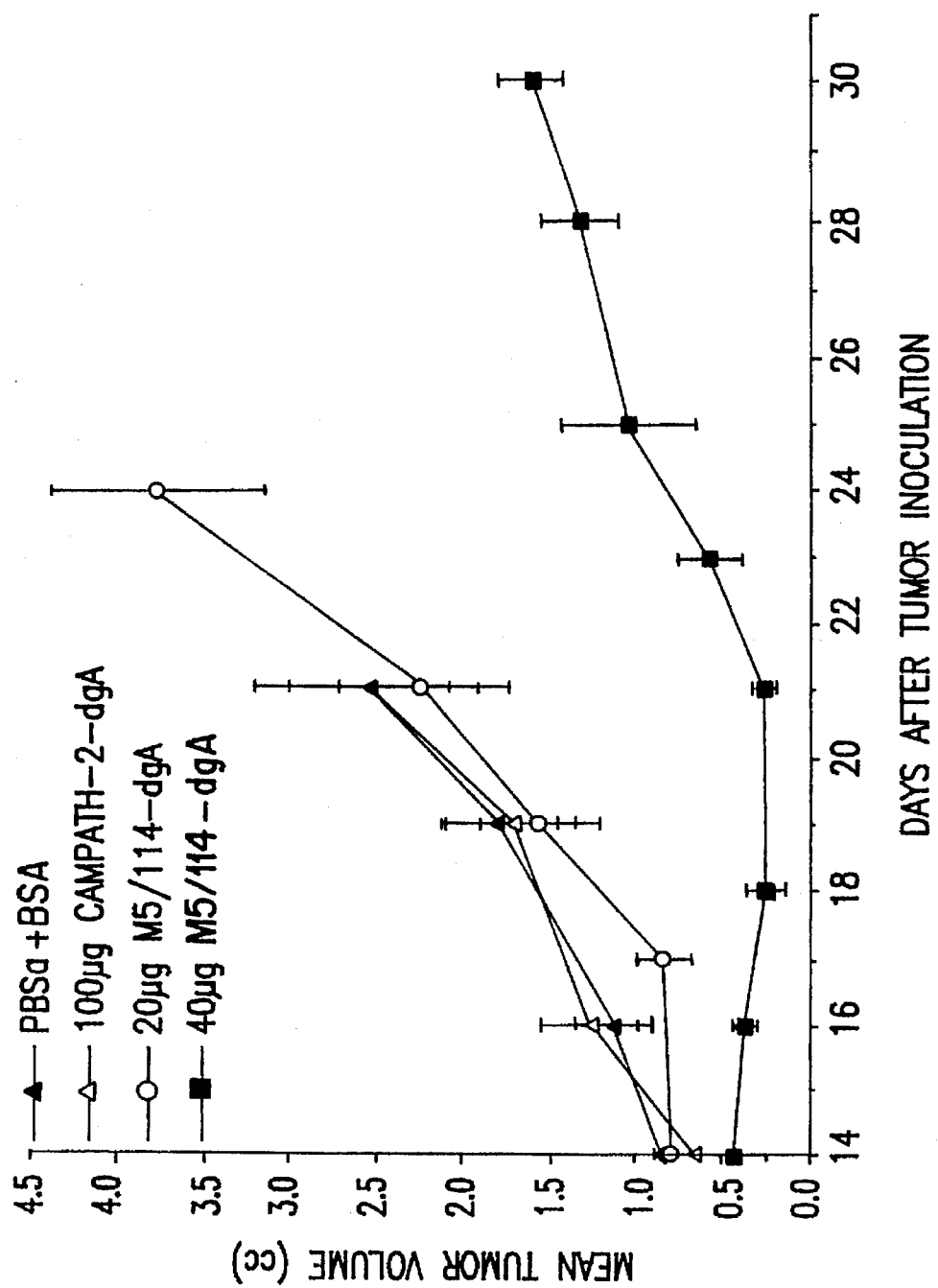
FIG. 8. This figure shows the in vivo antitumor effects of the anti-endothelial cell immunotoxin, M5/114-dgA, at various doses, including 20 μg (○) and 40 μg (■). These studies involved the administration of the immunotoxin intravenously 14 days after injection of tumor cells. Controls included the use of a control immunotoxin, CAMPATH-2-dgA (△) and PBS +BSA (▲).
Figure 9:
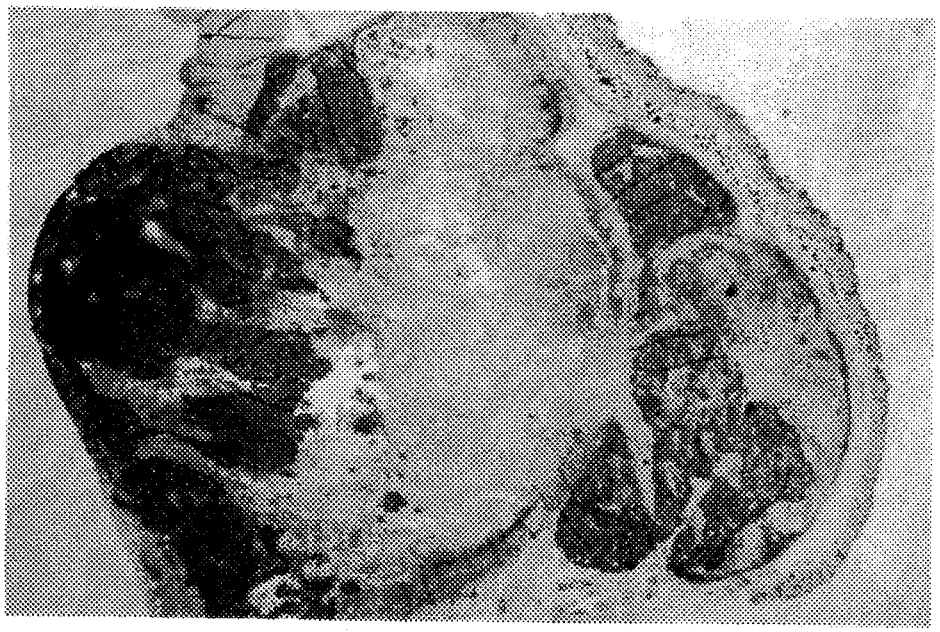
FIG. 9. This figure is a histological analysis of 1.2 cm H&E-stained tumor sections 72 hours after treatment with 20 μl of the anti-Class II immunotoxin, M5/114-d9A.

The next series of studies involved the application of one or both of the foregoing anti-Class I and anti-Class II immunotoxins, in the model tumor system disclosed in Example I. FIG. 8 illustrates the anti-tumor effects of the anti-tumor endothelial cell immunotoxin, M5-114 dgA. As can be seen, dosages as low as 20 μg exhibited a noticeable antitumor effect. While the change in mean tumor volume in the 20 μg-treated population does not, in FIG. 8, appear to be particularly dramatic, sections of the tumor, when H & E-stained, illustrated surviving "islands" of tumor cells in a "sea" of necrotic cells. This can be seen in FIG. 9, wherein the surviving islands of tumor cells are the darker staining areas, and the necrotic tissue the more lightly-staining areas.

Importantly, treatment with 40 μg of MS/115-dgA resulted in dramatic anti-tumor effects, as can be seen in FIG. 8. Here, 30 days after tumor inoculation the mean tumor volume equated with the 16 day figure in the controls. The dotted line in FIG. 8 represents the results that were expected with the use of 100 μg of M5/114 dgA, with a possible reoccurrence of tumor cell indicated at the 26 day position being the partial result of a surviving rim of viable cells observed in the treated solid tumor.

Figure 10:
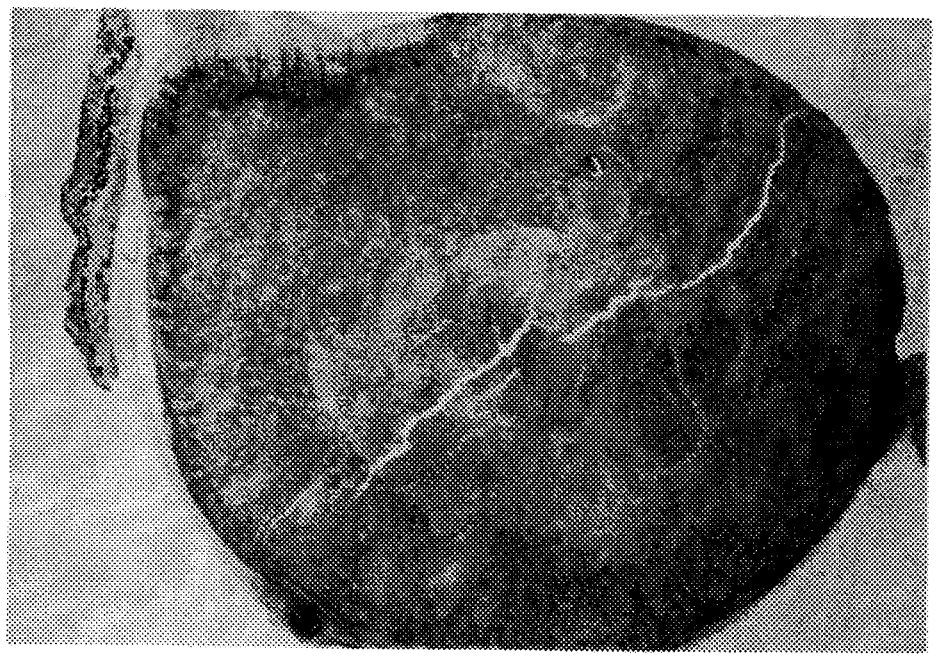
FIG. 10. This figure is a histological analysis of 1.2 cm H&E-stained tumor sections 72 hours after treatment with 100 μg of the anti-Class II immunotoxin, M5/114-dgA.

FIG. 10 is a section through a 1.2 cm tumor 72 hours after treatment with 100 μg of the anti-Class II immunotoxin M5/114 dgA, followed by H & E staining. As can be seen, this pattern is similar to the 20 μg data shown in FIG. 9, but certainly much more dramatic in that virtually no "islands" of tumor cells remain. It is estimated that this pattern represents a complete necrosis of greater than 95% of the tumor diameter, leaving only a thin cuff of surviving tumor cells, presumably nourished by vessels in overlying skin.

Figure 11:
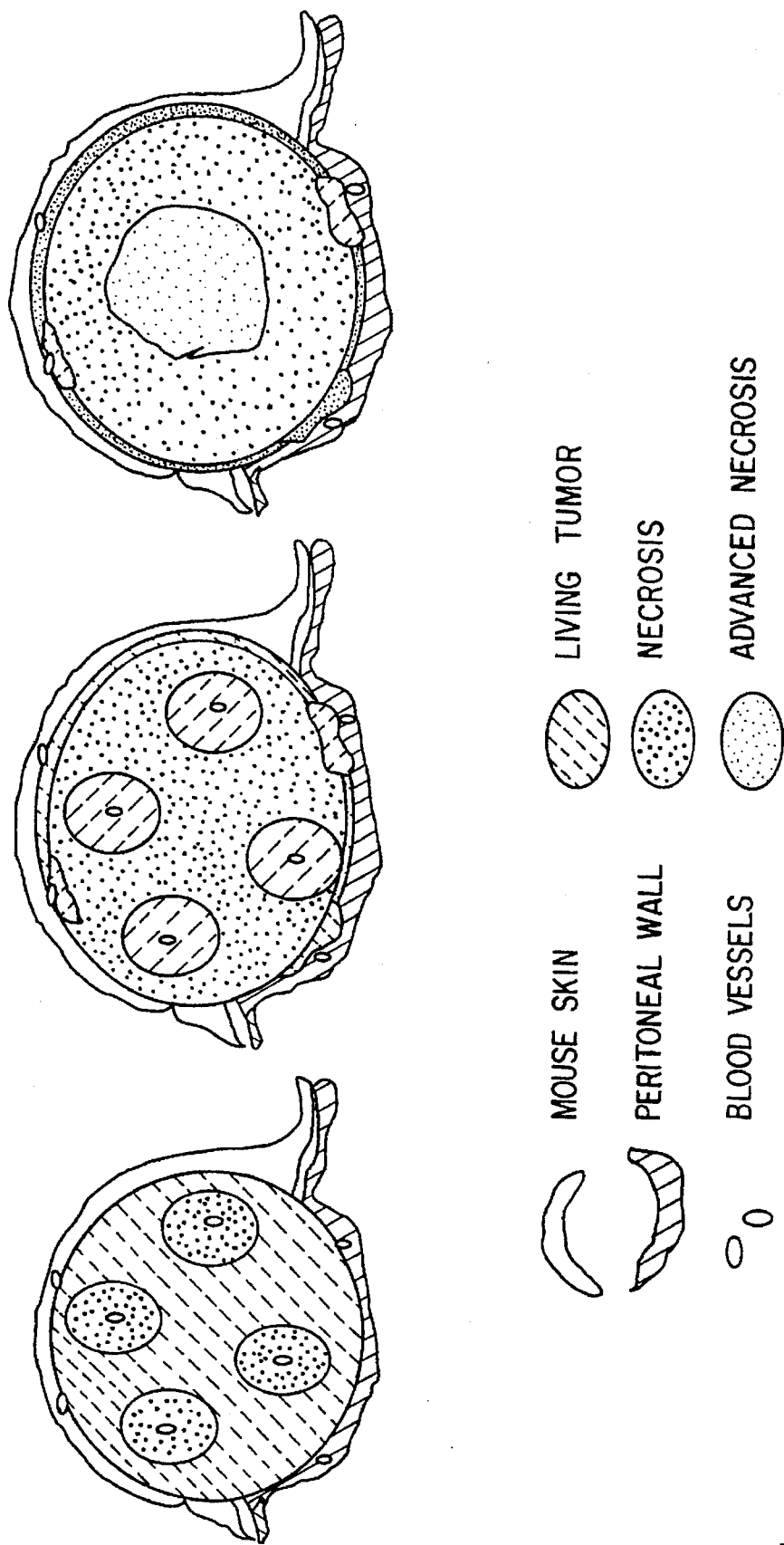
FIG. 11. This figure is a representation of the appearance of a solid tumor 48–72 hours after intravenous immunotoxin treatment, and compares the effect achieved with anti-tumor immunotoxin, to that achieved with anti-endothelial cell immunotoxin therapy.

To address this potential source of recurrence, i.e., the potential for a cuff of surviving tumor cells, combined therapy with both an antitumor (anti-Class I) and an anti-endothelial (anti-Class II) immunotoxin was undertaken. The theory for this combined therapeutic approach can be seen in FIG. 11, which illustrates the appearance of the solid tumor following 48–72 hours of intravenous immunotoxin treatment. At the left hand side of the Figure is represented a tumor following anti-tumor immunotoxin therapy alone. As illustrated, only those areas immediately surrounding the blood vessels become necrotic following treatment with the anti-tumor immunotoxin, due to the inability of the immunotoxin to sufficiently infiltrate the tumor and reach the tumor cells that are distal of the blood vessels. In stark contrast, shown in the middle panel of FIG. 11 is a representation of the low dose treatment with anti-endothelial cell immunotoxin. Here is illustrated the effects of a low dose of the anti-endothelial cell immunotoxin, which results in necrosis of the tumor in those parts distal of the blood vessels, except for the outer rim of the tumor which is presumably fed by associated normal tissues. At low dosages, only those areas of the tumor closest to the blood vessels will receive sufficient oxygen and nutrients. Next, the high dose anti-endothelial immunotoxin results are illustrated on the right hand side of FIG. 11. Here, the only living tumor remaining is that associated with the outer rim of the tumor. It was a goal of combined therapy studies to demonstrate an additive or even synergistic effect when both an anti-tumor immunotoxin and anti-endothelial cell immunotoxin were employed in combination. This effect is illustrated in the panel at the right hand side of FIG. 11.

Figure 12:
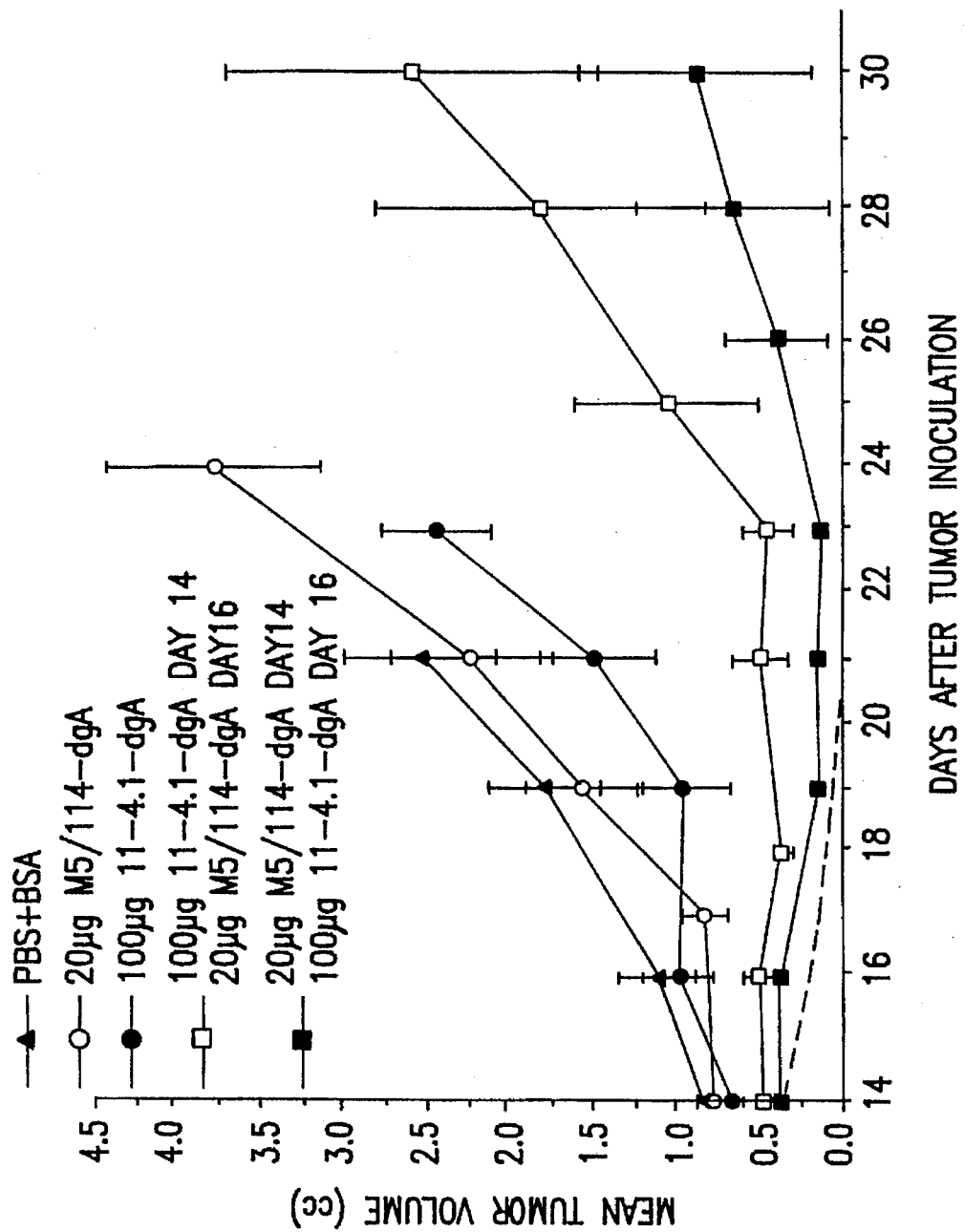
FIG. 12. This figure shows the antitumor effects of single and combined treatments with anti-Class I and anti-Class II immunotoxins in SCID mice bearing large solid C1300(Mu-γ) tumors. SCID mice bearing 1.0–1.3 cm diameter tumors were injected intravenously 14 days after tumor inoculation with 20 μg of Class II immunotoxin (○), 100 μg Class I immunotoxin (●), or diluent alone (▲). Other animals received the anti-Class II immunotoxin followed by two days later by the anti-Class I immunotoxin (■), or vice versa (□). Tumor size was measured at regular intervals and is expressed as mean tumor diameter ±SEM. Each treatment group consisted of 4–8 mice.

The results of this combination therapy are shown in FIG. 12. FIG. 12 shows the anti-tumor effects of the anti-tumor immunotoxin (11-4.1-dgA) alone at a high dose, the anti-tumor endothelial cell immunotoxin (M5/114-dgA) alone at a low dose, as well as combinations of both. The results demonstrate that both immunotoxins had a transient but noticeable effect in and of themselves, with the anti-tumor immunotoxin showing a slightly greater anti-tumor effect than the anti-tumor endothelial cell immunotoxin, although this might be a dosing effect.

Truly dramatic synergistic results were seen when both were used in combination. When 100 μg of the anti-tumor immunotoxin was given on day 14, followed by 20 μg of the anti-tumor endothelial cell immunotoxin on day 16, one out of four cures were observed. When the order of administration was reversed, i.e., the anti-tumor endothelial cell immunotoxin given first, even more dramatic results were observed, with two out of four cures realized. The latter approach is the more logical in that the initial anti-endothelial cell therapy serves to remove tumor mass by partial necrosis, allowing better penetration into the tumor of the anti-tumor immunotoxin.

Therapeutic doses ($\geq 40$ μg) of M5/114-dgA did not cause detectable damage to Class II-positive epithelial cells or to hepatic Kupffer cells, as assessed by histopathological analysis at various times after treatment. Any lymphoid cells destroyed by M5/114-dgA were apparently replaced from bone marrow precursors because, 20 days after treatment, all mature bone marrow cell populations and splenic B cell compartments were normal.

C. DISCUSSION

The findings from this model validate the concept of tumor vascular targeting and, in addition, demonstrate that this strategy is complimentary to that of direct tumor targeting. The theoretical superiority of vascular targeting over the conventional approach was established by comparing the in vivo antitumor effects of two immunotoxins, one directed against tumor endothelium, the other against the tumor cells themselves, in the same model. The immunotoxins were equally potent against their respective target cells in vitro but, while 100 μg of the tumor-specific immunotoxin had practically no effect against large solid C1300(Muγ) tumors, as little as 40 μg of the anti-tumor endothelial cell immunotoxin caused complete occlusion of the tumor vasculature and dramatic tumor regressions.

Despite causing thrombosis of all blood vessels within the tumor mass, the anti-tumor endothelial cell immunotoxin was not curative because a small population of malignant cells at the tumor-host interface survived and proliferated to cause the observed relapses 7–10 days after treatment. The proximity of these cells to intact capillaries in adjacent skin and muscle suggests that they derived nutrition from the extratumoral blood supply, but the florid vascularization and low interstitial pressure in those regions of the tumor rendered the surviving cells vulnerable to killing by the anti-tumor immunotoxin (Jain, 1990; Weinstein & van Osdol, 1992), so that combination therapy produced some complete remissions.

The time course study demonstrated that the anti-Class II immunotoxin exerted its antitumor activity via the tumor vasculature since endothelial cell detachment and diffuse intravascular thrombosis clearly preceded any changes in tumor cell morphology. In contrast with the anti-tumor immunotoxin, the onset of tumor regression in animals treated with the anti-tumor endothelial cell immunotoxin was rapid. Massive necrosis and tumor shrinkage were apparent in 48–72 hours after injection. Focal denudation of the endothelial lining was evident within 2–3 hours, in keeping with the fast and efficient in vivo localization of M5/114 antibody and the endothelial cell intoxication kinetics of the immunotoxin (t ½₀=2 hours, t ½=12.6 hours.

As only limited endothelial damage is required to upset the hemostatic balance and initiate irreversible coagulation, many intratumoral vessels were quickly thrombosed with the result that tumor necrosis began within 6–8 hours of administration of the immunotoxin. This illustrates several of the strengths of vascular targeting in that an avalanche of tumor cell death swiftly follows destruction of a minority of tumor vascular endothelial cells. Thus, in contrast to conventional tumor cell targeting, anti-endothelial immunotoxins could be effective even if they have short serum half lives and only bind to a subset of tumor endothelial cells.

MHC Class II antigens are also expressed by B-lymphocytes, some bone marrow cells, myeloid cells and some renal and gut epithelia in BALB/c nu/nu mice, however, therapeutic doses of anti-Class II immunotoxin did not cause any permanent damage to these cell populations. Splenic B cells and bone marrow myelocytes bound intravenously injected anti-Class II antibody but early bone marrow progenitors do not express Class II antigens and mature bone marrow subsets and splenic B cell compartments were normal 3 weeks after therapy, so it is likely that any Ia$^+$ myelocytes and B cells killed by the immunotoxin were replaced from the stem cell pool. It is contemplated that the existence of large numbers of readily accessible B cells in the spleen prevented the anti-Class II immunotoxin from reaching the relatively inaccessible Ia$^+$ epithelial cells but hepatic Kupffer cells were not apparently damaged by M5/114-dgA despite binding the immunotoxin. Myeloid cells are resistant to ricin A-chain immunotoxins, probably due to unique endocytic pathways related to their degradative physiologic function (Engert et al., 1991).

No severe vascular-mediated toxicity was seen in the studies reported here because mice were maintained on oral antibiotics which minimized immune activity in the small intestine.

The findings described in this example demonstrate the therapeutic potential of the vascular targeting strategy against large solid tumors. As animal models for cancer treatment are widely accepted in the scientific community for their predictive value in regard to clinical treatment, the invention is also intended for use in man. Numerous differences between tumor blood vessels and normal ones have been documented (Denekamp, 1990; Jain, 1988) and are envisioned to be of use in practicing this invention. Tumor endothelial markers may be induced directly by tumor-derived angiogenic factors or cytokines (Ruco et al., 1990; Burrows et al., 1991) or could relate to the rapid proliferation (Denekamp & Hobson, 1982) and migration (Folkman, 1985a) of endothelial cells during neovascularization. Candidate anti-tumor endothelial cell antibodies include FB-5, against endosialin (Rettig et al., 1992), and E9 (Kumar et al., 1993) which are reportedly highly selective for tumor vascular endothelial cells. Two related antibodies developed by the present inventors, TEC-4 and TEC-11, against carcinoma-stimulated human endothelial cells, show strong reactivity against vascular endothelial cells in a wide range of malignant tumors but little or no staining of vessels in benign tumors or normal tissues. Vascular targeting is therefore envisioned to be a valuable new approach to the therapy of disseminated solid cancers for which there are currently no effective treatments.

EXAMPLE III

Targeting the Vasculature of Breast Tumors

This example describes an approach for targeting the vasculature of breast cancer and other solid tumors in humans. This approach is exemplified through the use of bispecific antibodies to selectively induce the activation antigens, Class II and ELAM-1, on the vascular endothelial cells of syngeneic breast tumors in mice and then targeting these antigens with immunotoxins.

Murine models may first be employed. The results from such studies will be understood to parallel the situation in humans, as mouse models are well accepted and routinely employed for such purposes. Following successful vascular targeting in the mouse, success in man is likely as highly specific anti-breast cancer antibodies are available (Denekamp, 1984; Girling et al., 1989; Griffin et al., 1989; Lan et al., 1987; Boyer et al., 1989).

In the case of clinical (as opposed to diagnostic applications), the central issue is to confine the expression of the induced target antigen to tumor vasculature. In the case of Class II, which is present on the vasculature of normal tissues in mice and humans (Natali et al., 1981, Daar et al., 1984; Hammerling, 1976), the objective is to suppress its expression throughout the vasculature and then selectively induce it on tumor vasculature. In the case of ELAM-1, which is absent from the vasculature of normal tissues (Cotran et al., 1976), the objective is to induce its expression selectively on tumor vasculature.

A. OVERVIEW

1. Selective Induction of Class II Expression on Tumor Vasculature

C3H/He mice will be injected subcutaneously with syngeneic MM102 mammary tumor cells. The tumor cells express Ly6.2 which is a unique marker in C3H mice (Ly6.1 positive). Mice bearing solid MM102 mammary tumors will be treated with CsA to reduce or abolish Class II expression throughout the vasculature. As originally shown in the dog (Groenewegen et al., 1985), and, as recently confirmed by the inventors in the mouse, CsA inhibits T cell and NK cell activation and lowers the basal levels of IFN-γ to the extent that Class II disappears from the vasculature. The mice will then be injected with a bispecific (Fab'—Fab') anti-CD28/anti-Ly6A.2 antibody, which should localize to the tumor by virtue of its Ly6.2-binding activity. The bispecific antibody should then bind to T cells which are present in (or which subsequently infiltrate (Blanchard et al., 1988) the tumor. Crosslinking of CD28 antigens on the T cells by multiple molecules of bispecific antibody attached to the tumor cells should activate the T cells via the CsA-resistant CD28 pathway (Hess et al., 1991; June et al., 1987; Bjorndahl et al., 1989). Activation of T cells should not occur elsewhere because the crosslinking of CD28 antigens which is necessary for activation (Thompson et al., 1989; Koulova et al., 1991) should not occur with soluble, non-tumor cell bound, bispecific antibody. T cells which become activated in the tumor should release IFN-γ which should induce Class II antigens on the tumor vascular endothelium (Collins et al., 1984; Pober et al., 1983) and probably on the tumor cells themselves (Boyer et al., 1989). Animals will then be treated with anti-Class II immunotoxins to destroy the tumor blood supply.

2. Induction of ELAM-1 Expression on Tumor Vasculature

Mice bearing solid MM102 mammary tumors will be injected with bispecific (Fab'—Fab') anti-CD14/anti-Ly6A.2 antibody. The antibody should localize in the tumor by virtue of its Ly6.2-binding activity. It should then activate monocytes and macrophages in the tumor by crosslinking their CD14 antigens (Schutt et al., 1988; Chen et al., 1990). The activated monocytes/macrophages should have tumoricidal activity (Palleroni et al., 1991) and release IL-1 and TNF which should rapidly induce ELAM-1 antigens on the tumor vascular endothelial cells (Bevilacqua et al., 1987; Pober et al., 1991). A monoclonal antibody to mouse ELAM-1 will be generated and used as an immunotoxin to destroy the tumor blood supply.

B. STUDY DESIGN AND METHODS

1. Suppression of Class II Expression a) Mouse mammary tumors, MM102 and MM48

The tumors preferred for use are the mouse mammary (MM) tumors which have been extensively characterized by Dr. Reiko Irie and colleagues (Irie, 1971; Irie et al., 1970). The inventors have obtained from Dr. Irie (UCLA School of Medicine, California) two transplantable tumors, MM102 and MM48. The MM102 line derives from a spontaneous mammary tumor which originated in a C3H/He mouse. The MM102 tumor carries an antigan which is closely related to, or identical to, Ly6A.2 (Seto, et al., 1982). Since the C3H/He mouse expresses Ly6.1 and not Ly6.2, this marker is tumor-specific in syngeneic mice. The MM48 tumor, a variant of the original tumor, lacks Ly6A.2 and provides a specificity control in the proposed studies. Both tumors form continuously-growing solid tumors when injected into the subcutaneous site.

b) Monoclonal antibodies

For targeting the Ly6A.2 antigan, the inventors have obtained the anti-Ly6A.2 hybridoma, S8.106, from Dr. Ulrich Hammerling (Memorial Sloan-Kettering Cancer Center, N.Y.). This hybridoma secretes a mouse $IgG_{2a}$ antibody (Kimura, et al., 1980) which has been shown to react specifically with MM102 and other Ly6A.2 expressing MM tumors (Seto, et al., 1982).

An appropriate anti-mouse CD28 antibody (Gross, et al., 1990) is that obtainable from Dr. James Allison (University of California, California). Ascitic fluid from hybridoma-bearing animals is also available for synthesizing the bispecific antibody. The antibody is a hamster IgG.

Isotype-matched negative control antibodies will be the WT1 antibody (anti-human CD7) which is a mouse $IgG_{2a}$ and a hamster IgG of irrelevant specificity from the ATCC.

Antibodies will be purified on staphylococcal Protein A coupled to Sepharose, or by ion exchange and size exclusion chromatography on Sepharose 4B as described by Ghetie, et al. (1988). The ability of the purified anti-Ly6A.2 antibody to bind to MM102 cells and of the anti-CD28 antibody to bind mouse T cells will be confirmed by FACS analyses as described by Burrows et al., (1991).

Purified antibodies will be filtered through 0.22 μm membranes, aliquotted, and stored at −70° C.

c) Preparation of Fab' fragments

F(ab')$_2$ fragments of purified anti-Ly6A.2 and anti-CD28 antibodies will be prepared by pepsin digestion, as described by Glennie et al. (1987). Purified antibodies (5–10 mg) will be dialyzed against 0.1M sodium acetate, pH 4.1, and digested with 4% (w/w) pepsin at 37° C. The digestion will be followed by SDS-PAGE and terminated by raising the pH when optimal digestion is achieved. Undigested IgG will be removed by chromatography on a Sephacryl S-200 column equilibrated with PBS. The F(ab')$_2$ fragments will be analyzed by SDS-PAGE and, if detectable levels of undigested antibody should remain, the F(ab')$_2$ fragments will be further purified by removal of undigested antibody on a Protein A-Sepharose column. Fab' fragments will be prepared from F(ab')$_2$ fragments by reduction with 5 mM DTT for 1 hr at 25° C., followed by removal of free DTT on a Sephadex G-25 column equilibrated against phosphate-EDTA buffer (Glennie et al., 1987)

d) Preparation of anti-Ly6A.2/anti-CD28 bispecific antibodies

For the production of anti-Ly6A.2-anti-CD28 bispecific antibodies, Fab' fragments of each antibody will be initially prepared as above and will be left unalkylated. Heterodimer molecules will be prepared as described by Glennie et al. (1987). Fab' fragments will be reduced with DTT in 0.2M Tris-HCl buffer, pH 8.0, containing 10 Mm EDTA for 60 min. at room temperature. One of the Fab' fragments will be then reacted with Ellman's reagent (2 mM) for 1 hour at room temperature in acetate buffer, pH 5.0. The free Ellman's reagent will be separated using a Sephadex G-25 column. The derivatized Fab' fragment will be then mixed with the other reduced Fab' and allowed to react at room temperature for 24 hours. Bispecific antibodies will be separated from remaining Fab' fragments by gel filtration over Sephacryl S-200 columns.

e) Confirmation of cell binding-capacity of anti-Ly6A.2/anti-CD28 bispecific-antibody FACS analyses will be performed to verify the dual cell-binding capacity of the bispecific antibody. MM102 tumor cells (grown as an ascites) will be treated for 30 minutes at 4° C. with the bispecific antibody (10 μg/10$^6$ cells) and washed. The tumor cells will then be incubated with fluoresceinated goat anti-hamster immunoglobulin for 30 minutes at 4° C. and washed again. The fluorescence associated with the cells will then be measured using the FACS. Positive staining of tumor cells coated with bispecific antibody and lack of staining of cells coated with anti-Ly6A.2 antibody alone will confirm that the bispecific antibody is intact and is capable of binding tumor cells. The study will be repeated using a CD28 positive mouse T cell lymphoma line (e.g., EL4) and with fluoresceinated goat anti-mouse immunoglobulin as the detecting antibody to confirm that the bispecific antibody has CD28-binding capacity.

f) Activation of T cells by anti-Ly6A.2/anti-CD28 bispecific antibody plus MM102 tumor cells It will be important to confirm that tumor cells coated with the bispecific antibody, but not free bispecific antibody, are able to activate T cells in a CsA-resistant fashion. T cells will be enriched from the spleens of C3H/He mice by depleting B-cells and macrophages according to the procedure of Lee and colleagues 1990 (Lee, et al., 1990). Spleen cells are treated with mouse anti-Class II antibody and the Class II-expressing cells are removed by treating them with goat anti-mouse IgG-coupled magnetic beads and withdrawing them with a strong magnet. The non-adherent cells are decanted and are treated further to remove residual B cells and macrophages by successive rounds of treatment with anti-J11D plus BRC and anti-MAC-1 antibody plus goat anti-rat serum. After these procedures, the remaining cells are $\geq 95\%$ T cells and $<3\%$ Ig positive.

T cells will be cultured (0.5 to $1 \times 10^5$ cells/0.2 ml) in medium in the wells of 96-well plates. Various concentrations of anti-CD28 IgG, anti-CD28 Fab' or anti-Ly6A.2/anti-CD28 bispecific antibody will be added together with various concentrations of one of the following costimulants: PMA, IL1 or anti-CD3 IgG. CsA (0.5 µg/ml) will be added to an identical set of cultures. The cultures will be incubated at 37° C. for 3 days, $^3$H-thymidine (1 µCi/culture) will be added and the plates harvested 24 hours later. These studies should confirm that bivalent anti-CD28, but not monovalent Fab' anti-CD28 or the bispecific antibody, stimulate T cells and that the stimulation is not CsA inhibitable.

Next, MM102 and MM48 cells, obtained from ascitic tumors of C3H/He mice, will be treated with mitomycin C (25 µg/ml) for 20 minutes at 37° C. The cells will then be washed and the above study repeated with the inclusion of 0.5 to $1 \times 10^5$ mitomycin-treated MM102 or MM48 cells along with the T cells in the cultures. The MM102 cells, but not the MM48 cells, should present the bispecific antibody to the T cells and, together with the costimulant, induce their stimulation.

g) Confirmation that injection of anti-Ly6A.2/anti-CD28 bispecific antibody into CsA-treated MM102 tumor-bearing mice results in induction of Class II selectively on tumor vasculature C3E/He mice will be injected subcutaneously with $10^6$ MM102 or MM48 tumor cells. One day later they will start daily treatments with CsA (60 mg/kg/day) given either orally dissolved in olive oil or injected intraperitoneally. After 10–14 days, when the tumors will have reached 1.0–1.3 cm in diameter, and when Class II will have disappeared from the vasculature, mice will be injected with 50–100 µg of anti-Ly6A.2/anti-CD28 bispecific antibody. Other mice will receive various control treatments, including unconjugated anti-Ly6A.2 or anti-CD28 (Fab' and IgG) or diluent alone. Two or three days later, the mice will be sacrificed and the tumors and various normal tissues will be removed for immunohistochemical examination. Frozen sections will be cut and stained for the presence of Class II antigens and for the presence of hamster immunoglobulin using indirect immunoperoxidase techniques, as presented in the foregoing examples.

Upon demonstration that Class II antigens are strongly and selectively expressed on the vasculature of MM102 tumors but not on MM48 tumors, the tumor therapy studies below will be carried out. If Class II antigens are absent from tumor vasculature but hamster immunoglobulin is present, this would indicate that the bispecific antibody had localized to the tumor, as anticipated from prior studies with analogous bispecific antibodies (Perez, et al., 1985; Garrido, et al., 1990), but that T cell activation had not occurred sufficiently for IFN-γ secretion to ensue. If so, the presence of T cells will be verified by staining frozen tumor sections with anti-CD28 and anti-CD3 antibodies. If T cells are present, again as would be anticipated from prior studies (Koulova, et al., 1991; Perez, et al., 1985), the failure to get Class II induction might be attributable to the need for two signals for T cell activation, i.e. a 2nd signal might be missing. This will be checked by coadministering an anti-Ly6A.2/anti-CD3 bispecific antibody, which together with the anti-Ly6A.2/anti-CD28 bispecific, should provide the signalling needed for T cell activation.

h) Synthesis of anti-class II-SMPT-dgA immunotoxin

Immunotoxins directed against murine class II MHC molecules will be prepared by linking the rat monoclonal anti-murine I-A$^k$ antibody to deglycosylated ricin A (dgA) using the disulfide clearable crosslinker, SMPT (Thorpe, et al., 1988). Affinity purified antibody molecules will be derivatized by reaction with a five-fold molar excess of SMPT in borate buffer, pH 9.0, for 60 min. at room temperature. Free SMPT will be removed by passage through a Sephadex G-25 column equilibrated against phosphate buffered saline containing EDTA (1 mM, PBSE). Under these conditions, an average of 1.7 molecules of SMPT are introduced per immunoglobulin molecule. Next, the derivatized antibody will be allowed to react with reduced dgA for 72 hrs. at room temperature. Under these conditions, immunoconjugates form through formation of disulfide linkage between sulfhydryl groups on dgA molecules and SMPT. Immunoconjugates will be separated from free dgA by gel filtration in Sephacryl S-200 columns and from unreacted antibody by passage through Blue-Sepharose and elution with phosphate buffer containing 0.5M NaCl. Purity of immunoconjugates will be assessed by SDS-PAGE.

i) Tumor therapy studies

C3H/He mice will be injected subcutaneously with $10^6$ MM102 or MM48 tumor cells and, one day later, will start daily treatments with CsA (60 mg/kg/d). When the tumors have grown to 1.0–1.3 cm diameter, the mice will receive an intravenous injection of 50–100 µg anti-Ly6A.2/anti-CD28 bispecific antibody (perhaps together with anti-Ly6A.2/anti-CD3 bispecific antibody if indicated by the studies in Section (h) above). Two or three days later, 100 µg of the anti-Class II immunotoxin will be administered intravenously. Anti-tumor effects will be monitored by measuring the size of the tumors at regular intervals and by histological examination as in Section C. The specificity of any anti-tumor effects will be established by comparing the anti-tumor effects with those in mice which receive various control treatments, including unconjugated anti-Ly6A.2 Fab' and IgG, unconjugated anti-CD28 Fab' and IgG, and anti-Class II immunotoxin alone.

2. Induction of ELAM-1 on tumor vasculature by anti-Ly6A.2/anti-CD14 bispecific antibody a) Raising of anti-ELAM-1 monoclonal antibodies i) Induction of ELAM-1 on SVEC cells for immunization Expression of cytokine-induced adhesion molecules on SVEC murine endothelial cells will be induced by stimulation of SVEC cell monolayers with a cocktail of rMuIL-1β (50 I.U./ml), rMuTNFα (100 IU/ml) and bacterial endotoxin (100 ng/ml) for 4 hrs at 37° C., as described for the induction of human ELAM-1 (Bevilacqua, et al., 1987). Preliminary evidence suggests that SVEC cells activated in this manner express murine ELAM-1, since radiolabeled U937 cells, which bear the ELAM-1 agent, display increased adhesion to activated SVEC cells within 2 hrs of the addition of the cytokines. The increased endothelial cell adhesiveness peaked at 4–6 hrs., as previously reported for human ELAM-1. Although cytokine-activated SVEC cells also displayed long-term (up to 48 hrs.) adhesiveness to U937 cells, this was probably not due to ICAM-1/LFA-1 or VCAM-1/VLA-4 interactions, since the assays were carried out at 4° C., under shear stress conditions, which inhibits any adhesive interactions other than those between selections and their carbohydrate agents (Spertini, et al., 1991). Increased adhesiveness at the later time points was probably mediated by the selection LAM-1 (Mel-14) on U937 cells and its agent (the MECA 79 antigen) on SVEC cells (81). In subsequent studies, this pathway will be blocked by the inclusion of Mel-14 and/or MECA 79-specific antibodies in the adhesion assays (Imai, et al., 1991).

ii) Immunization

Rat monoclonal antibodies will be raised against inducible proteins on mouse endothelial cells. SVEC cells will be stimulated for 6 hrs., as previously described, before immunization of Wistar rats. The rats will be boosted three weeks following the initial injection with identically-prepared SVEC cells. Serum from the injected rats will be tested for the presence of antibodies specific for induced proteins on yendothelial cells 7–10 days after the second boost, using FACS analysis of induced and non-induced SVEC cells. Additional boosting and screening will be repeated as necessary.

Once antibody levels have been detected in acceptable titers, rats will be given a final boost with induced SVEC cells and their spleens removed after 3 days. Splenocytes will be fused with Y3 Agl.2.3 rat myeloma cells according to standard protocols using poly-ethylene glycol 4000 (82). Hybridomas will be selected using HAT medium and the supernatants screened using FACS analysis.

iii) Screening

Those hybridomas secreting antibodies reacting with cytokine-induced but not with resting SVEC cells will be selected for further characterization. Reactivity will be assessed by indirect immunofluorescence with hybridoma supernatants and FITC-labeled mouse anti-rat immunoglobulin antibodies. The selected hybridomas will be expanded, and the immunoglobulin purified from their culture supernatants. Confirmation of ELAM-1 reactivity will be carried out as described below.

iv) Characterization of antigens

The physicochemical properties of the precipitated antigens will be investigated after activating SVEC cells with cytokines in the presence of cycloheximide or tunicamycin and by immunoprecipitation of antibody-reactive molecules from lysates of $^{35}$S-methionine-labeled SVEC cells, using the selected MAbs. Immunoprecipitates will be subsequently analyzed by SDS-PAGE. Confirmation of murine ELAM-1 reactivity will be carried out by comparison of the precipitated material and human ELAM-1 using SDS-PAGE, one-dimensional proteolytic maps with staphylococcal V8 protease and $NH_2$-terminal sequences.

b) Preparation of anti-Ly6A.2-anti-CD14 bispecific antibodies

Bispecific antibodies will be constructed using Fab' fragments derived from anti-Ly6A.2 and anti-CD14 monoclonal antibodies, essentially as described in the previous section. Several anti-mouse CD14 monoclonal antibodies have been raised (23). We feel it is premature to approach these workers with a view to establishing a collaboration until we have raised anti-mouse ELAM-1 monoclonals and verified their performance as immunotoxins.

c) Synthesis and cytotoxicity testing of anti-ELAM-1 immunotoxins

Immunotoxins directed against murine ELAM-1 will be constructed by cross-linking monoclonal anti-mouse ELAM-1 antibodies (as characterized above) to dgA using SMPT. The procedure involved will be identical to that described in the previous sections. Activity will be assessed by toxicity studies with cytokine-activated SVEC cells.

d) Confirmation of ELAM-1 induction on tumor vasculature and not on normal vasculature C3H/He mice bearing 1.0–1.3 cm MM102 or MM48 tumors will be injected i.v with anti-Ly6A.2/anti-CD14 bispecific antibody or with various control materials including unconjugated anti-Ly6A.2 and anti-CD14 antibodies (Fab' and IgG) and diluent alone. Tumors will be removed at various times and cryostat sections will be cut and stained with rat monoclonal antibodies to murine ELAM-1, using standard indirect immunoperoxidase techniques. The presence of the bispecific antibody on tumor cells will be verified by staining for rat immunoglobulin. Resident macrophages and infiltrating monocytes will be detected by indirect immunoperoxidase staining with anti-Mac-1 (CD 11b/CD 18) antibodies. Cytokine-producing cells will be identified in serial cryostat sections of tumors by in situ hybridization with $^{35}$S-labeled antisense asymmetric RNA probes for murine IL-1β and TNFα mRNA.

e) Tumor therapy studies

C3H/He mice bearing 1.0–1.3 cm MM102 or MM48 tumors will be injected with 50–100 µg anti-Ly6A.2/anti-CD14 bispecific antibody or with various control materials including unconjugated anti-Ly6A.2 and anti-CD14 antibodies (Fab' and IgG) and diluent alone. One to three days later, the mice will receive intravenous injections of anti-ELAM-1 immunotoxin, an isotype-matched immunotoxin of irrelevant specificity or unconjugated anti-ELAM-1 antibody. Anti-tumor effects will be monitored by measuring the size of the tumors at regular intervals and by histological examination, as in the preceding examples.

Mice will be injected subcutaneously with $10^6$ MM102 or MM48 tumor cells (in 0.1 ml saline) either on the abdominal wall or on the flank. In some studies, cyclosporin A (60 mg/kg/day) will be injected intraperitoneally or given in the drinking water. The mice will be observed daily thereafter and the dimensions of the tumor will be measured. When the tumor reaches a diameter of 1.0–1.3 cm, the mice will receive an injection of bispecific antibody (0.1 ml in saline) into a tail vein and then 2–3 days later will receive an intravenous injection of immunotoxin, again into the tail vein. The study is terminated by euthanizing the mice when their tumors reach 1.5–2 cm in diameter in any dimension.

Each group will comprise 8–10 animals, and there will generally be 5 or 6 treatment groups making a total of 40–60 mice per study. One such study will be performed per month.

f) Raising monoclonal antibodies

Adult Wistar rats will be used. Rats will be immunized by injecting them i.m with mouse endothelial cells (SVECs) homogenized in 0.1 ml of a 50:50 mixture of Freund's incomplete adjuvant and saline. Rats will be boosted 1 month and 2 months later in the same manner. 7–10 days after the second boost, 0.1 ml blood will be removed from tail vein and the serum will be analyzed for the presence of antibody. If sufficiently positive, the rats will be given a final i.m boost with SVEC cells and 3 days later, the rats will be euthanized their spleens dissected out for monoclonal antibody production.

g) Raising ascites

BALB/c nude mice will be injected intraperitoneally with 0.5 ml Pristane (2, 6, 10, 14-tetramethylpentadecane) 2 to 4 weeks before being injected intraperitoneally with rat hybridoma cells. The mice will be weighed daily and euthanized when their body weight increases by 20% or more due to hybridoma growth in the peritoneal cavity. The contents of the peritoneal cavity will then be drained and monoclonal antibodies purified from the ascitic fluid.

h) Choice of species and number of animals

Mice: The antitumor effects of immunotoxins in animals cannot be predicted from tissue culture studies. Such factors as hepatic entrapment, blood clearance rates and binding to serum components makes it essential that intact animal systems are used for evaluation. The choice of mice as the test animal is determined by the fact that inbred strains exist in which mammary tumors will grow reproducibly. The number of animals (8–10) per treatment group is the minimum for statistically significant differences between different treatment groups to become apparent. The number of treatment groups (5–6) per study is the minimum for an effect of a specific immunotoxin to be distinguished from an effect of its components (antibody alone, ricin A chain alone, or mixtures of the two) and for superiority over control immunotoxin of irrelevant specificity to be demonstrated.

Rats: Since antibodies are to be raised to mouse endothelial cell antigens, it is best to use another species for immunization. Rats are preferred for these studies because they are inbred and respond consistently to the immunogen.

EXAMPLE IV

Identification and Characterization of the Tumor Endothelial Cell Marker, Endoglin, and Antibodies thereto This example describes the generation of two new monoclonal antibodies, TEC-4 and TEC-11, directed against a tumor vasculature antigen. TEC-4 and TEC-11 are shown to recognize endoglin, which is shown to be associated with growth and proliferation of human tumor endothelial cells in vitro and in vivo. Endoglin is selectively upregulated on vascular endothelial cells in a broad range of malignant tumors and is envisioned to provide a suitable marker for use in the diagnosis and therapy of miscellaneous solid tumors.

A. MATERIALS AND METHODS

1. Cells and culture conditions cell lines were obtained from the Imperial Cancer Research Fund, London (U.K.) Tissue Bank unless otherwise indicated. SP2/0 murine myeloma cells, SAOS osteosarcoma cells and the ECV-304 human endothelial cell line were obtained from the American Type Culture Collection, Rockville, Md. A375M and T8 human melanoma lines were obtained from Dr. I. R. Hart (Imperial Cancer Research Fund, London, U.K.). NCI-H146 and SCC-5 human lung cancer cell lines were obtained from Dr. J.D. Minna (U.T. Southwestern Medical Center, Dallas, Tex.). L428 and L540 human Hodgkins/Sternberg-Reed cells were obtained from Dr. A. Engert (Department of Medicine, Cologne, Germany).

The murine endothelial cell lines used were SV40-transformed mouse lymph node endothelial cells (SVEC, O'Connell et al., 1990), obtained from Dr. M. Edidin (Johns-Hopkins, Baltimore, Md.); LEII, obtained from Dr. W. Risau (Max-Planck Institute, Martinsried, Germany); and mouse pulmonary capillary endothelial cells (MPCE) obtained from Prof. A. Curtis (Department of Cell Biology, Glasgow, U.K.).

Primary endothelial cell cultures from chinese hamster epididymal fat pad and bovine heart were established using the methods described by Bjorntorp et al. (Bjorntorp et al., 1983) and Revtyak et al. (Revtyak et al., 1988).

Human umbilical vein endothelial cells (HUVEC) were isolated from fresh tissue by the method of Jaffe et a2. (Jaffe et al., 1973) or were purchased from Clonetics Corp., San Diego, Calif. Cultures were maintained in gelatin-coated flasks in Medium 199 (Gibco-Biocult, Ltd., Paisley, U.K.) supplemented with Earle's salts, 20% (v/v) fetal calf serum, endothelial cell growth supplement (ECGS, 0.12 mg/ml), 0.09 mg/ml heparin, glutamine and antibiotics at 37° C. in 5% $CO_2$ in air or in Endothelial Growth Medium (Clonetics) at 37° C. in 10% $CO_2$ in air. All other cell lines were maintained in Dulbecco's modified Eagle's medium (DMEM) supplemented with 10% (v/v) fetal calf serum, 2.4 mM L-glutamine, 200 units/ml penicillin, 10 µg/ml streptomycin, 100 µM non-essential amino acids, 1 µM Na Pyruvate and 18 µM HEPES at 37° C. in 10% $CO_2$ in air.

Murine L-cell transfectants expressing human endoglin were produced as described by Bellon et al. (1993).

2. Antibodies

The F8/86 mouse IgG1 anti-human von-Willebrands Factor antibody (Naieum et al., 1982) was purchased from DAKO Ltd (High Wycombe, U.K.) and used at 1:50 dilution. A mouse IgG1 anti-human vitronectin receptor antibody, LM142 (Cheresh, 1987) was obtained from by Dr. D. Cheresh (Scripps Clinic, La Jolla, Calif.). The mouse IgG1 anti-rat Thy 1.2 antibody (Mason and Williams, 1980) was used as an isotype matched control for F8/86 and LM142. The mouse myeloma proteins TEPC-183 ($IgM_k$) and antibody MTSA ($IgM_k$), which do not react with human tissues, were used as negative controls for TEC-4 and TEC-11. The mouse IgG1 anti-endoglin antibody 44G4 (Gougos and Letarte, 1988) has been described previously.

3. Immunoprecipitation

HUVEC were metabolically labelled by overnight incubation in 0.1 mCi/$10^6$ cells $^{35}$S-methionine in methionine-free RPMI supplemented with 20% (v/v) fetal calf serum, ECGS, glutamine heparin and antibiotics as described above. Monolayers were washed twice in PBS and adherent cells were lysed in NET buffer (50 mM Tris-HCl, pH 8.0, 200 mM NaCl, 1 mM EDTA, 0.5% NP-40) supplemented with 0.1M iodoacetamide to inhibit disulfide exchange.

For immunoprecipitation, preformed immunocomplexes were used as described by Liet al. (1989). 0.2 mg of purified MAb in 200 µl of NET buffer was mixed with 250 µl of GAMIg (goat anti-mouse immunoglobulin) serum and incubated for 30 min. at room temperature. Immunocomplexes were pelleted by centrifugation and the pellet was washed two times in 300 µl of NET buffer. One ml of lysate from $5 \times 10^7$ $^{125}$I-labeled cells was mixed with immunocomplexes (prepared as above) on a rotator at 4° C. for 1 hr. The lysate containing the immunocomplexes was layered on top of a discontinuous sucrose gradient consisting of 750 µl each of 40 (bottom), 30, 20, and 10% (top) sucrose in 12×75-mm tubes. Tubes were centrifuged at 600 g for 20 min. at room temperature. The sucrose was decanted and the pellets were resuspended in a small amount of PBS. Samples were transferred to new tubes and then centrifuged. The pellet was boiled for 1 min. in sample buffer with or without 2-mercaptoethanol (2-ME) and electrophoresed on 12.5% slab gels for 16 hr at 15 mA. The gels were dried and exposed to film for 24 hr at −70° C.

4. Complement fixation

The ability of TEC-4 and TEC-11 to fix complement was assessed as follows. Primary antibody incubations and washing were performed as for indirect immunofluorescence. After the third wash, HUVEC were resuspended in 50 µl of a 1/10 dilution of guinea pig complement (ICN, High Wyecombe, U.K.) for 20 min. at 37° C., at which point 50 µl of 0.25% (w/v) trypan blue was added and cell number and plasma membrane integrity were estimated visually.

5. Indirect Immunofluorescence

Tumor cells and endothelial cells were prepared for FACS analyses as described by Burrows et al. (1991). All manipulations were carried out at room temperature. 50 µl of cell suspension at $2-3 \times 10^6$ cells/ml in PBS-BSA-$N_3$ were added to the wells of round-bottomed 96 well microtiter plates (Falcon 3910). Primary antibodies (10 µg/ml) were added in 50 µl volumes, and the plates sealed. After 15 min., the cells were washed 3 times by centrifuging the plates at 800×g for 30 s, removing the supernatants by flicking and patting dry on absorbent tissue, and resuspending the cells in 150 µl/well PBS-BSA-$N_3$. Fluorescein isothiocyanate (FITC)-conjugated rabbit antibodies against mouse immunoglobulins (DAKO Corp., Carpinteria, Calif.), diluted 1:20 in PBS-BSA-$N_3$, were distributed in 50 µl volumes into the wells. The cells were incubated for a further 15 min. and washed as before. Cell-associated fluorescence was measured on a FACScan (Becton-Dickenson, Fullerton, Calif.). Data were analyzed using the LYSYSII program. The mean fluorescence intensity (MFI) of cells treated with the control antibody, MTSA, was subtracted from that of cells treated with TEC-4 or TEC-11 to obtain the specific MFI attributable to antigen binding.

For competitive binding inhibition assays, biotinylated TEC-4 or TEC-11 antibodies were mixed with unlabelled TEC-4, TEC-11 or control antibodies at ratios of 1:1, 1:10 and 1:100. Indirect immunofluorescent staining of HUVEC was carried as before except that biotinylated antibodies bound to the cells were detected with a 1:50 dilution of streptavidin-phycoerythrin (Tago, Inc., Burlingame, Calif.). Percent blocking of biotinylated antibodies was calculated as follows:

blocking=MFI in presence of blocking Ab (background MFI)/ MFI in presence of non-specific Ab (background MFI)

Indirect immunofluorescence of L-endoglin transfectants was carried out as described by Bellon et al. (1993). Parental L cells and L cell transfectants expressing human endoglin ($1 \times 10^6$ cells) were incubated for 45 min. at 4° C. with MAb 44G4 IgG (10 ug/ml), TEC-4 (10 µg/ml) or TEC-11 (10 µg/ml). Cells were then washed and incubated with FITC-conjugated F(ab')$_2$ goat anti-mouse IgG (H+L)(Tago).

6. Cellular protein and nucleic acid analyses

HUVEC were stained with TEC-11 at 20 µg/ml as described in 'Indirect Immunofluorescence', and sorted into TEC-11$^{lo}$ and TEC-11$^{hi}$ populations using a FACStar Plus cell sorter.

Total cellular protein content was estimated from the uptake of free FITC as described by Stout and Suttles (1992). Sorted cells were centrifuged at 150×g, 5 min., and fixed in cold 70% ethanol for 15 min. The cells were pelleted as before, resuspended in PBS containing 20 µg/ml FITC and incubated on ice for 60 min. before being washed and analyzed on the FACStar Plus. The ethanol fixation effectively removed any prior fluorescent label as evidenced by the lack of detectable fluorescence of controls which were not incubated with FITC.

Acridine orange staining of DNA and RNA was performed according to a method adapted from that of Darzynkiewicz et al. (Darzynkiewicz et al., 1976). Sorted cells were centrifuged at 150×g for 5 min. and resuspended at $1.5 \times 10^6$ cells/ml in 200 µl of DMEM/10% FCS. 0.5 ml 0.15M citrate/phosphate buffer, pH 3.0, containing 0.1% (v/v) Triton-X-100 (Sigma), 0.2M sucrose and 0.1 mM EDTA was added and the cells were maintained at 4° C. immediately before analysis, 0.5 ml 0.15M citrate/phosphate buffer, pH 3.8, containing 1M NaCl and 0.002% (w/v) acridine orange (Polysciences Inc., Warrington, Pa.) was added. After 5 min. at room temperature, the fluorescence intensities of individual cells were measured in the FACStar Plus. Free nuclei and cell doublets were excluded from the data collection. Green and red fluorescence were plotted against each other in a 2-dimensional dot plot that enables cells to be assigned to different stages of the cell cycle ($G_0$, $G_1$, S, $G_2$+M) according to relative DNA and RNA content (Darzynikiewicz et al., 1976).

7. Immunohistochemistry

Human and animal tissue samples were snap-frozen over liquid nitrogen, mounted in OCT Compound (Miles, Inc., Elkhart, Ind.) and 8 µM sections were cut in a Tissuetek 2 cryostat (Baxter) onto slides precoated with 3-aminopropyltriethoxysilane (Sigma). Sections were stored at −80° C. until required. Indirect streptavidin-biotin immunoperoxidase staining was carried out as follows. Sections were air-dried at room temperature for 30 min., fixed in acetone for 15 min., rehydrated in PBS for 5 min. and incubated in a humidified chamber for 45–60 min. with purified primary antibodies at 10 µg/ml in PBS-0.2% BSA or with undiluted culture supernatant. After 2 washes in PBS, the sections were incubated for 30–45 min. with biotinylated F(ab')$_2$sheep anti-mouse IgG (H+L) (Sigma #B-6774) diluted 1:200 in PBS-0.2% BSA. After a further 2 washes in PBS, the sections were incubated for 30–45 min. with streptavidin-biotin-horseradish peroxidase complex (Strept ABC Complex, DAKO #K377) diluted 1:100 in PBS-0.2% BSA. After a final 2 washes, the reaction product was developed using 0.5 mg/ml 3',3'-diaminobenzidine (DAB, Sigma) or 1 mM 3-amino-9-ethylcarbazole (AEC, Sigma) containing 0.01% (v/v) hydrogen peroxide. The sections were counterstained with Mayer's hematoxylin (Sigma) for 10–30 s, washed in tap water and mounted in CrystalMount (Biomeda Corp., Foster City, Calif.).

B. RESULTS

1. Production of TEC-4 and TEC-11 antibodies

The TEC4 and TEC11 monoclonal antibodies were raised and selectively screened in the following manner. HT-29 human colonic adenocarcinoma cells were obtained from the Imperial Cancer Research Fund Central Tissue Bank and seeded at 25% of confluent density in tissue culture flasks in Dulbeccos Modified Eagles Medium (DMEM) supplemented with 10% v/v fetal calf serum (FCS), 2.4 mM L-glutamine, 200 units/ml penicillin and 100 μg/ml streptomycin. The cells were allowed to grow to full confluence over 4–5 days incubation at 37° C. in a humidified atmosphere of 90% air/10% $CO_2$ before the supernatant tissue culture medium (hereafter referred to as HT-29 tumor-conditioned medium, HT-29 TCM) was removed, filtered through a 0.22 μM filter to ensure sterility and to remove any particulate matter, and stored at 4° C. for no more than one week before use. HT-29 human adenocarcinoma cells were used to prepare TCM because they had previously been shown to secrete angiogenic into their culture medium (Rybak et al., 1987) and angiogenic has been found to induce neovascularization (i.e., profound alteration of endothelial cell behavior) in an in vivo assay (Fettet al., 1987).

Human umbilical vein endothelial cells (HUVEC) were incubated in Medium 199 supplemented with 20% w/v FCS, glutamine and antibiotics and mixed 1:1 with HT-29 TCM. After 48–72 hours at 37° C. the endothelial cells were harvested non-enzymatically, using a rubber policeman, and $1-2 \times 10^6$ cells were injected intraperitoneally into a BALB/c mouse. This entire procedure was repeated three times at two to three week intervals, the final injection being by the intravenous route.

Three days later, splenocytes from the immunized animal were fused with SP2/0 murine myeloma cells at a ratio of 1:2 using PEG2000 (Kohler and Milsrein, 1975; Tazzari et al., 1987). The cell mixture was introduced into the wells of 96-well flat bottomed microtiter plates along with $3 \times 10^4$ syngeneic peritoneal feeder cells per well. Twenty-four hours later 100 μl of medium containing hypoxanthine, ammopterin and thymidine (HAT Medium) was added to select for fused cells (hybridomas). The cultures were fed with additional HAT Medium at 3 day intervals.

When hybridomas had grown to high density, 50 μl samples of supernatant were taken and screened by galactosidase anti-galactosidase (GAG) ELISA (Burrows et al., 1991) for antibodies reactive with HT-29-activated HUVEC. All positive wells were seeded into 24-well plates, expanded by further culture in. HAT medium, and retested 7–10 days later by the same technique. Antibodies that bound to HUVEC in the ELISA were further tested for reactivity with HUVEC cell surface determinants by FACS (see 'Indirect Immunofluorescence'). All positive wells were harvested and samples stored in liquid nitrogen. The remaining cells from each positive well were cloned in 96 well plates by the limiting dilution method (Kohler and Milstein, 1975).

When the clones had grown to high density, 50 μl samples of supernatant were taken and assayed by GAG ELISA against HT-29 TCM-activated HUVEC and 'resting' HUVEC grown in the absence of tumor-derived factors. Any wells which showed significantly greater reactivity with HT-29 TCM-activated HUVEC than with control HUVEC were recloned and expanded to culture flasks to provide adequate supernatant for subsequently screening for lack of reactivity with quiescent HUVEC in frozen sections of human umbilical vein (see 'Immunohistochemistry').

Supernatants from these expanded clones were screened by standard indirect immunoperoxidase techniques (Billington and Burrows, 1987) by sequential incubation with $F(ab)_2$ sheep anti-mouse IgG (1:200, Sigma) and streptavidin-biotin-horseradish peroxidase complex (1:100, Dakopatts) against a small panel of normal and malignant human tissues on cryostat sections. After this round of screening two clones, 1G4 (TEC4) and 2G11 (TEC11), were selected for further study on the basis of significantly greater reactivity with endothelial cells in sections of solid tumors than with those in sections of normal tissues.

Both TEC4 and TEC11 antibodies were isotyped as IgM using the Immunotype™ mouse monoclonal antibody isotyping kit (Sigma Chemical Co., St. Louis, Mo.). TEC-4 and TEC-11 were purified from tissue culture supernatant by ammonium sulfate precipitation followed by Sephacryl S-300 size-exclusion chromatography and affinity chromatography on a Mannose-Binding Protein column (Pierce Chemical Co., Rockford, Ill.). TEC-4 and TEC-11 antibodies were biotinylated by incubation with a 40-fold molar excess of N-hydroxy-succinimidobiotin amidocaproate (Sigma) for 1 h at room temperature followed by dialysis against 2 changes of PBS.

2. Evidence that TEC-4 and TEC-11 recognize Endoglin

Figure 13A:
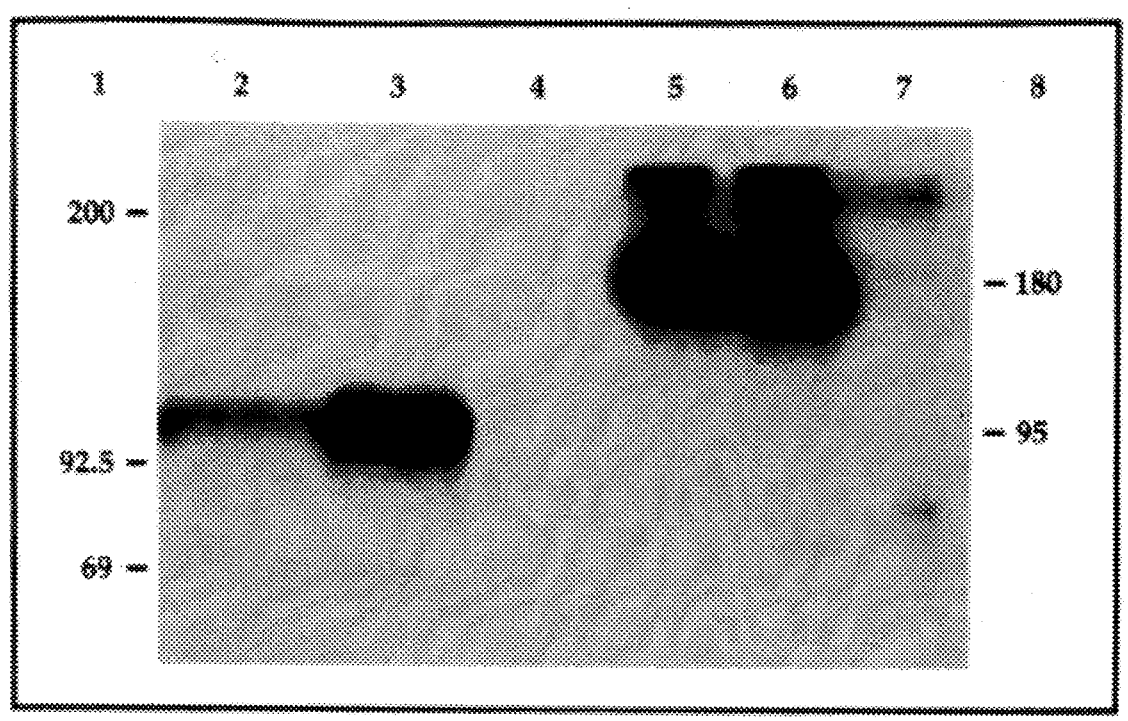
FIG. 13a. Gel electrophoretic analysis of proteins immunoprecipitated from 35S-labelled human umbilical vein endothelial cells (HUVEC), showing that TEC-4 and TEC-11 recognize endoglin. 12.5% SDS-PAGE gel of proteins immunoprecipitated under reducing (lanes 2–4) or non-reducing (lanes 5–7) conditions with TEC-4 (lanes 2,5), TEC-11 (lanes 3,6) or TEPC-183 (lanes 4,7). Lane 1: Position of the $^{14}$C-labelled standards of the molecular weights indicated. Lane 8: Positions of 95 kDa and 180 kDa species.
Figure 13B:
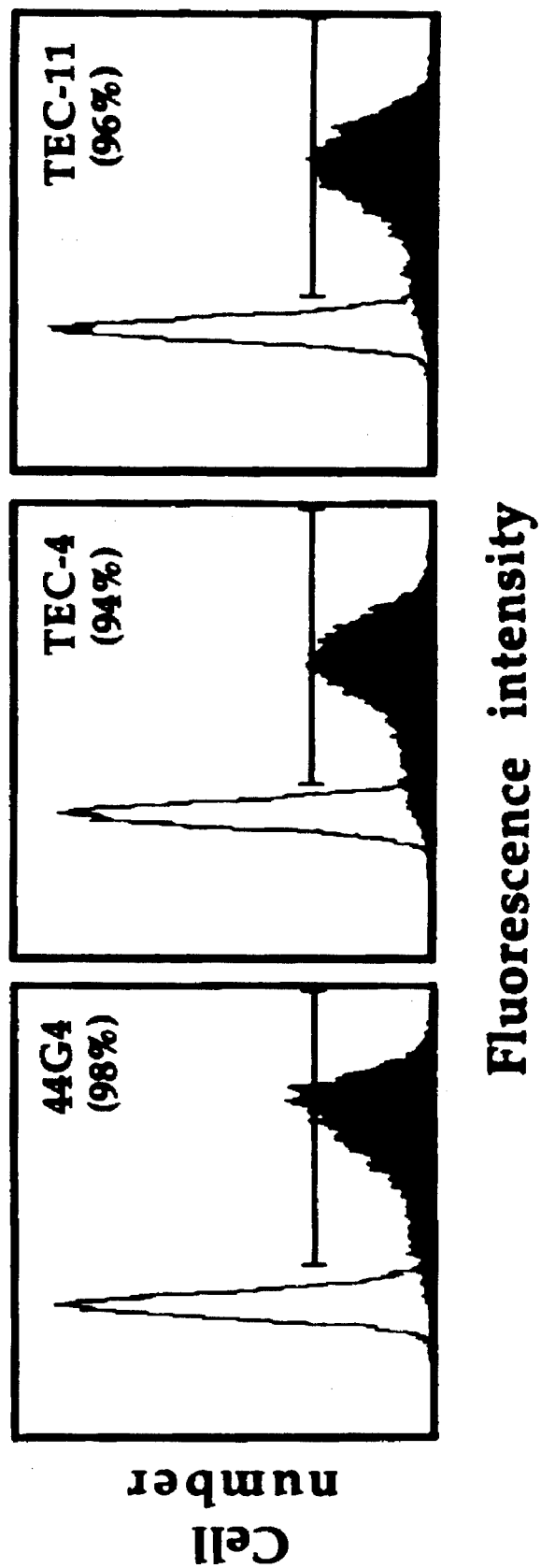
FIG. 13b. Reactivity of TEC-4 and TEC-11 with human endoglin transfectants, showing that TEC-4 and TEC-11 recognize endoglin. Parental murine L cells and L cell transfectants expressing human endoglin were incubated with purified MAb TEC-11, TEC-4 and 44G4 followed by FITC-conjugated F(ab')$_2$ goat anti-mouse IgG (H+L). The staining observed on the parental L cells with the MAb (white histograms) was indistinguishable from that observed with IgM and IgG1 controls. The L cell endoglin transfectants (black histograms) were specifically reactive with all 3 antibodies as revealed by the percentage of cells included within the gate and shown in parentheses.

TEC-4 and TEC-11 immunoprecipitated a molecule that migrated as a 95 kDa species when analyzed on SDS-polyacrylamide gels under reducing conditions (FIG. 13(a), lanes 2–4). When isolated and analyzed under non-reducing conditions, the molecule moved predominantly as a 180 kDa homodimer (FIG. 13(a), lanes 5–7). These biochemical characteristics were consistent with those described previously for endoglin; indirect immunofluorescence analysis of the binding of TEC-4 and TEC-11 to murine L-cells transfected with human endoglin was therefore performed to determine whether the antibodies indeed recognize endoglin. As shown in FIG. 13(b), TEC-4, TEC-11 and the reference anti-endoglin antibody, 44G4, all reacted strongly with endoglin-transfectant L-cells but were unreactive with parental L-cells.

3. Cross-blocking of TEC-4 and TEC-11 antibodies

Binding to L-endoglin transfectants (FIG. 13) and reciprocal preclearing before immunoprecipitation confirmed that TEC-4 and TEC-11 react with the same protein. Competitive inhibition of binding to HUVEC was carried out to determine whether TEC-4 and TEC-11 recognize the same or different epitopes on the endoglin molecule (FIG. 14).

Figure 14:
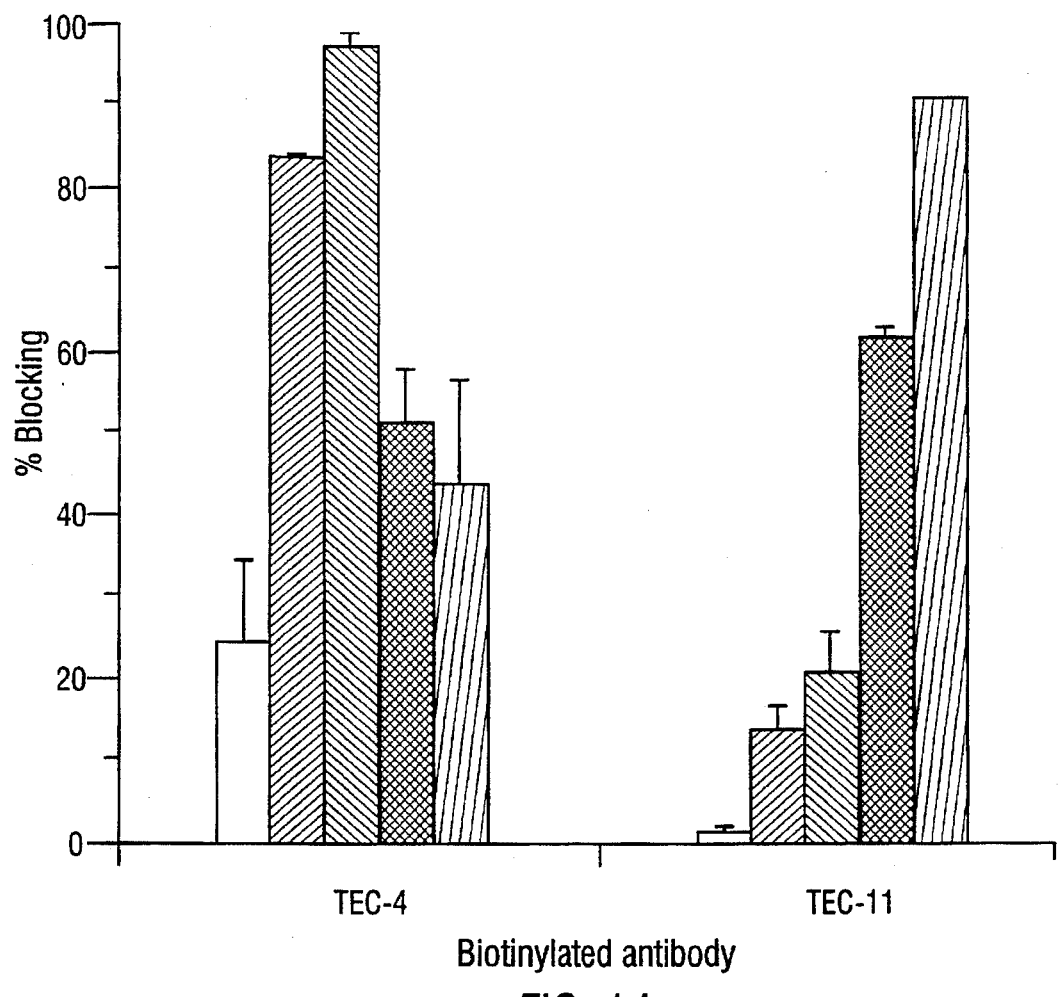
FIG. 14. Crossblocking of TEC-4 and TEC-11 antibodies. Biotinylated antibodies (10 μg/ml) were mixed with an equal volume of unlabelled TEC-4 antibody at 10 μg/ml (□) 100 μg/ml (▨) or 1000 μg/ml (■) or with unlabelled TEC-11 antibody at 10 μg/ml (■), 100 μg/ml (▨) and were added to HUVEC in PBS-BSA-N$_3$. Indirect immunofluorescence staining was carried out as described in Example V with the exception that labelled antibody binding was detected with a streptavidin-phycoerythrin conjugate. Each group of histograms shows the percent blocking of the biotinylated antibody by the different concentrations of unlabelled antibodies. Bar: SD of triplicate determinations.

TEC-4 and TEC-11 blocked themselves in a dose dependent manner, with TEC-11 being slightly more efficient that TEC-4 (FIG. 14). TEC-11 partially inhibited binding of TEC-4 by 51% at a ratio of 1:1, but increasing the ratio of TEC-4:TEC-11 to 1:10 did not increase the blocking. By contrast, TEC-4 inhibited TEC-11 binding by only 1% at 1:1, but this blocking increased in a dose-dependent fashion to reach 20% at a TEC-11:TEC-4 ratio of 1:100 (FIG. 14). The blocking effects were specific since neither TEC-4 nor TEC-11 blocked the binding of the anti-vitronectin receptor antibody LM142 to HUVEC, nor did LM142 interfere with TEC-4 or TEC-11 binding.

The epitopes recognized by TEC-4 and TEC-11 were distinct from that of 44G4, because 44G4 did not block TEC-4 or TEC-11, even at a ratio of 100:1.

Taken together, the above results indicate that (i) TEC-4 and TEC-11 recognize distinct but spatially close epitopes on the endoglin molecule, because neither antibody inhibited the binding of the other as efficiently or as completely as it blocked itself, and (ii) TEC-11 antibody has a greater affinity for endoglin than does TEC-4, because blocking of TEC-4 binding by TEC-11 was more efficient than the reciprocal event.

4. Complement fixation by TEC-4 and TEC-11 antibodies

Figure 15:
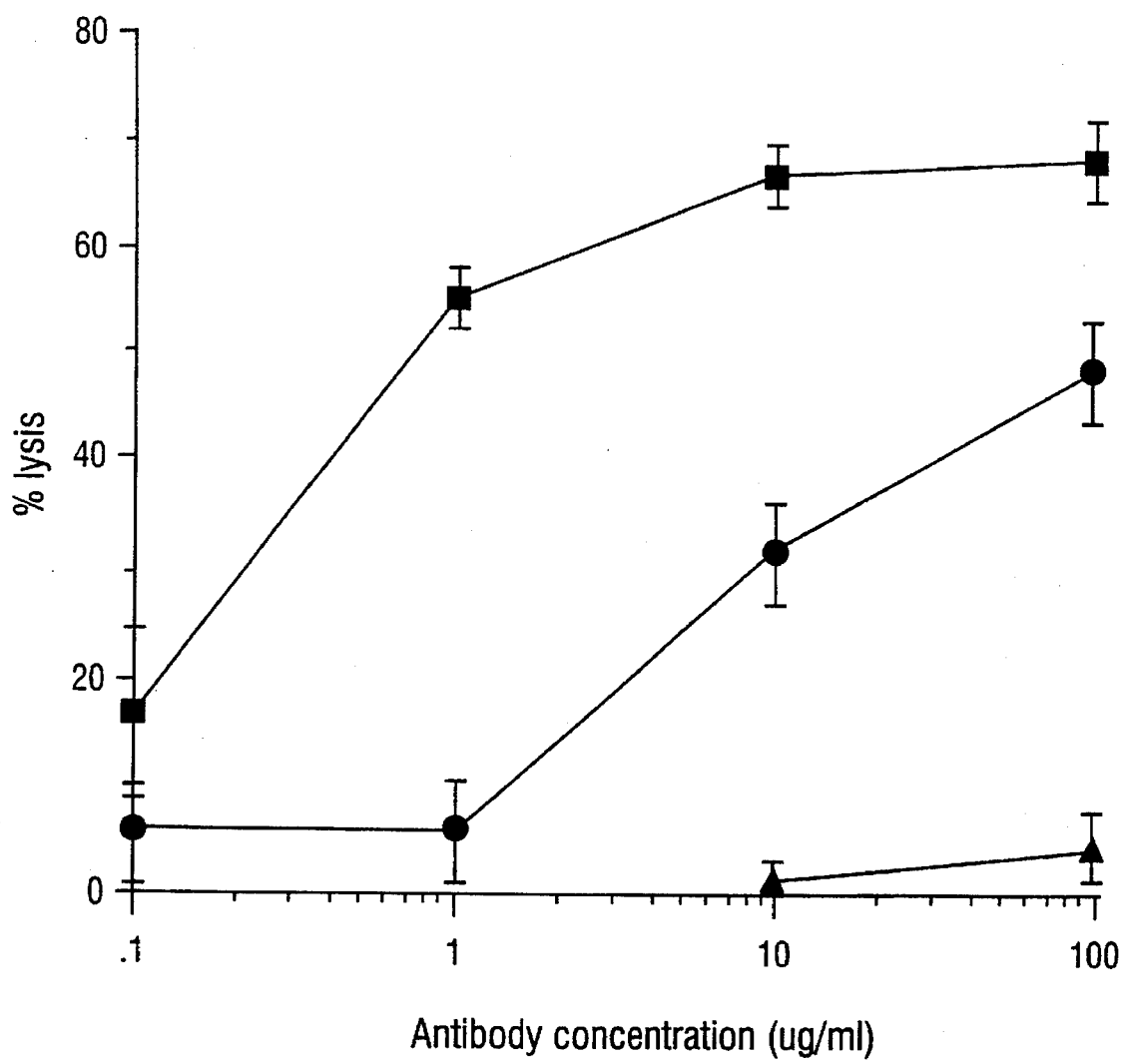
FIG. 15. Complement fixation by TEC-4 and TEC-11 antibodies. HUVEC were incubated with TEC-4 (●), TEC-11 (■) or MTSA (▼) antibodies, washed and subsequently incubated with guinea-pig complement. Cell number and viability were determined by trypan blue dye exclusion.

TEC-11 fixed complement approximately 100-fold more efficiently than did TEC-4, inducing lysis of >50% of HUVEC at a concentration of 1 μg/ml (FIG. 15). TEC-4 displayed no complement fixation activity at 1 μg/ml and lysed only 48% of HUVEC at a concentration of 100 μg/ml under these conditions. The superior complement-fixing activity of TEC-11 was due, at least in part, to its greater affinity, which resulted in greater binding of TEC-11 than TEC-4 to HUVEC at low antibody concentrations. The concentration of TEC-11 which produced half-maximal fluorescence in FACS analyses was 0.4 μg/ml as compared with 4 μg/ml for TEC-4.

5. Reactivity of TEC-4 and TEC-11 with normal and malignant human cell lines Binding of TEC-4 and TEC-11 to endothelial cells from several species and a panel of non-endothelial human cell lines was determined by indirect immunofluorescence and cytofluorimetry. The results are shown in Table IV. Essentially identical results were obtained with TEC-4 and TEC-11. Substantially higher levels of staining were detected on HUVEC than on any other cell tested in this study. The specific mean fluorescence intensity (MFI) of TEC-4 and TEC-11 on HUVEC was around 200.

A human endothelial cell line, ECV-304, which was derived from HUVEC (Kobayashi et al., 1991), gave lower MFI values of 35–45. ECV-304 cells also displayed diminished expression of several other endothelial cell markers, including EN4 antigen, angiotensin-converting enzyme and CD34. Endothelial cells of bovine, murine and chinese hamster origin displayed no detectable reactivity with either TEC-4 or TEC-11 antibodies. U937 cells were weakly labelled. Among the tumor cells, all lymphoma/leukemia lines were negative, as were the majority (5/7) of carcinoma lines. Interestingly, all 4 melanoma and sarcoma lines tested were weakly stained by TEC-4/TEC-11, with MFI values of 12–26. In addition, 2/4 breast cancer lines bound the antibodies weakly.

TABLE IV

Endoglin expression in tissue culture

| Cell type | Cell line(s) | Endoglin expression [1] |
|---|---|---|
| Endothelial | HUVEC | +++ |
| Endothelial | ECV-304 | ++ |
| Endothelial | BCA, CHEC, LE II, MPCE, SVEC | – |
| Myeloid | U937 | + |
| Myeloid | U266 | – |
| Leukemia/lymphoma | ARH-77, CEM, Daudi, Gaynor L428, L540, Nalm-6, K562 | – |
| Sarcoma | HT-1080, SAOS-2 | + |
| Melanoma | A375M, T8 | + |
| Carcinoma | LOVO, NCI-H146, SCC-5 | – |
| Breast tumor | MDA-MB-231, SKBR3 | + |
| Breast tumor | MCF-7, T 47D | – |
| Fibroblast transfectant | L-endoglin | +++ |

[1] Expressed as the corrected fluorescence intensity (CFI), calculated as described in the Materials and Methods where a CFI of <5 is represented by (–), 5-25 (+), 25-50 (++) 50-100 (+++) and >100 (++++).

6. Correlation between endoglin expression and endothelial cell proliferation in vitro TEC-4 and TEC-11 bound only weakly to quiescent HUVEC in situ in frozen sections of human umbilical vein (see following section). Endoglin expression reached high levels within 16 hours after the HUVEC were removed from the umbilical cord and placed into tissue culture and was not abolished in HUVEC cultures grown to confluence or deprived of serum or growth factors. However, confluent cultures displayed a bimodal distribution of TEC-4/TEC-11 binding by FACS (FIG. 16).

To characterize HUVEC populations expressing low and high levels of endoglin, confluent HUVEC cultures were stained with TEC-11 and sorted on a FACStar Plus cell sorter. The sorted populations were analyzed for total cellular protein content and relative DNA and RNA levels. The results of these studies are shown in FIG. 16 and Table V.

Figure 16A:
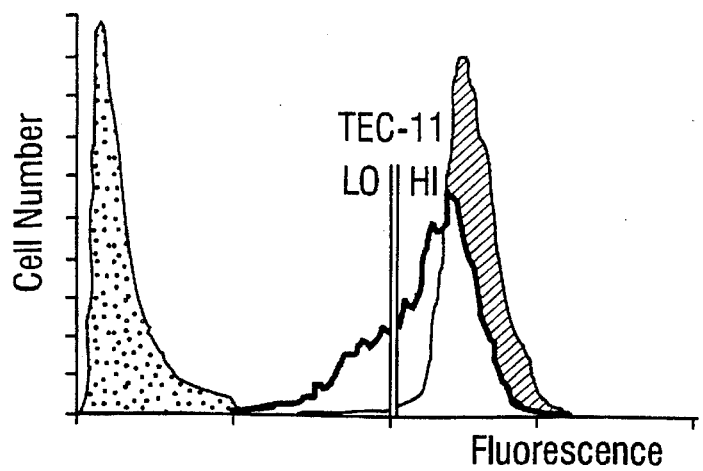
FIG. 16a. Correlation between TEC-11 binding and cellular proliferation in HUVEC. HUVEC from sparse cultures (hatched histogram) or post-confluent cultures (open histogram) were stained with TEC-11 by indirect immunofluorescence. Also shown, confluent HUVEC stained with negative control antibody MTSA (stippled histogram). Endoglin$^{lo}$ and endoglin$^{hi}$ populations of post-confluent HUVEC were separated on a FACStar Plus cell sorter as indicated and subsequently analyzed for PaNA and DNA content.
Figure 16B:
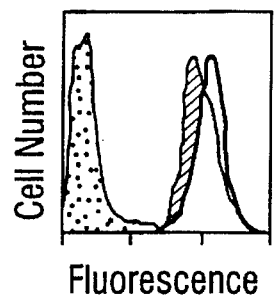
FIG. 16b. Lack of correlation between LM142 binding and cellular proliferation in HUVEC. HUVEC from sparse (hatched histogram) or post-confluent (open histogram) were stained with the anti-vitronectin receptor antibody LM142. Also shown, sparse HUVEC stained with negative control antibody MTSA (stippled histogram).
Figure 16C:
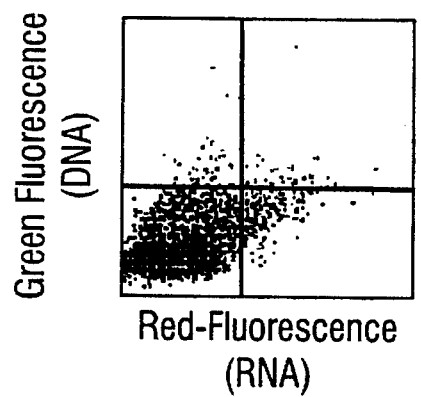
FIG. 16c. Correlation between TEC-11 binding and cellular proliferation in HUVEC. Endoglin$^{1o}$ HUVEC assayed for acridine orange interrelation into cellular DNA (x-axes) and DNA (y-axes). Essentially all cells contained low levels of RNA and DNA and were located within the lower left (G$_O$) quadrant.
Figure 16D:
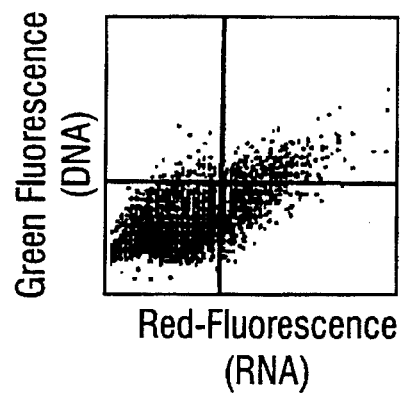
FIG. 16d. Correlation between TEC-11 binding and cellular proliferation in HUVEC. Endoglin$^{hi}$ MUVEC assayed for RNA and DNA as described in the above legend. Significant numbers of cells contain increased RNA levels (G$_1$ phase, lower right quadrant) and increased RNA and DNA levels (S+G$_2$M phases, upper right quadrant).

HUVEC from sparse cultures expressed uniformly high endoglin levels, as shown in FIG. 16a, hatched histogram, but when the same cells were grown to confluence and allowed to become partially quiescent over an additional 3–6 days, a bimodal distribution of TEC-11 binding was seen (FIG. 16a, open histogram). This pattern of TEC-11 binding was not simply a reflection of variations in cell size among the postconfluent HUVEC, because the expression of a control marker (the vitronectin receptor) was not significantly altered between HUVEC from sparse and postconfluent cultures (FIG. 16b). Postconfluent cells stained with TEC-11 were sorted into two fractions as indicated in FIG. 16a. Endoglin$^{hi}$ cells had a specific MFI 4.4 times greater than that of endoglin$^{lo}$ cells (Table V). Similarly, there was a 1.6-fold increase in binding of free FITC to cellular proteins in permeabilized endoglin$^{hi}$ cells by comparison to low endoglin expressors (Table V). Upregulated protein synthesis in the endoglin$^{hi}$ population reflected similar increases in cellular transcription, as indicated by acridine orange staining. While endoglin$^{lo}$ cells formed a single population with low relative RNA and DNA content (FIG. 16c), significant numbers of endoglin$^{hi}$ cells showed evidence of RNA and DNA synthesis consistent with cellular activation and proliferation (FIG. 16d). Indeed, when the sorted populations were separated into zones in the dot plots (FIG. 16c,d) according to standard criteria (Darzynkiewicz et al., 1976), virtually all endoglin$^{lo}$ cells were assigned to the non-cycling ($G_0$) population but, by contrast, 15% and 5% of endoglin$^{hi}$ cells were located in the $G_1$ (activated) and S+$G_2$/M (proliferating) fractions respectively (Table V).

TABLE V

Correlation between endoglin expression and endothelial cell proliferation in vitro.

| Fraction | MFI[1] | Relative protein[2] | Stage of cell cycle (%)[3] | | |
|---|---|---|---|---|---|
| | | | $G_0$ | $G_1$ | $S + G_2/M$ |
| Endoglin[lo] | 61.6 (2.4) | 100 | 95.8(2.4) | 3.1(1.4) | 1.1(1.4) |
| Endoglin[hi] | 270.2(3.8) | 156 | 79.1(5.8) | 15.5(2.9) | 5.4(1.2) |

[1]Mean fluorescence intensity of cells stained with 20 μg/ml TEC-11. Mean and standard deviation (in parentheses) of 2 studies.
[2]Estimated from non-specific binding of FITC to cellular proteins in permeabilized cells
[3]Estimated from 2-dimensional dot-plot after acridine orange staining as described in Materials and Methods and shown in FIG. 13. Mean and standard deviation (in parentheses) of 2 studies.

7. TEC-4 and TEC-11 binding to malignant and normal human tissues

Endothelial cells in miscellaneous tumors

TEC-4 and TEC-11 binding to vascular endothelial cells was assessed by immunoperoxidase staining of a panel of 51 miscellaneous human tumors. The results are shown in Table VI and FIGS. 17 and 18.

Both antibodies clearly stained the cytoplasm and luminal plasma membranes of vascular endothelial cells in a large majority of the tumors examined, including extensive series of breast and colorectal carcinomas. TEC-4 and TEC-11 reacted with capillaries and venules but not with arterioles in 20/22 evaluable cases. The reactivity patterns of the two antibodies were very similar, although TEC-11 tended to produce more intense staining than TEC-4 in some tissues (Table VI). In most tumor samples, a large majority (80–100%) of vessels which stained with the positive control anti-endothelial cell antibody (anti-yon Willebrands Factor) also stained moderately to strongly with TEC-4 and TEC-11. Often, TEC-4 and TEC-11 gave more uniform staining of capillaries than did the anti-yon Willebrands antibody. TEC-4 and 11 binding was variable both between and within histological tumor types.

Vascular endothelial cells were most strongly stained by TEC-4 and TEC-11 in sections of angiosarcoma, Hodgkins disease and colon, cecum and rectosigmoid carcinoma (Table VI). Parotid tumors (FIG. 17) and some breast carcinomas (FIGS. 17 and 18) also contained heavily-labelled vessels. Moderate staining of vascular endothelium was characteristic of pharyngeal, lung and ovarian carcinomas (Table VI). Vessels in soft tissue tumors (melanoma and osteosarcoma) were stained moderately by TEC-11 but only weakly by TEC-4. Lymphoma samples examined showed little or no staining with either antibody. TEC-4 and TEC-11 reactivity was restricted to human tissues—neither antibody stained endothelial cells in a variety of mouse, rat, guinea pig and hamster tumors, nor were vessels labelled in human tumor xenografts in nude mice.

TABLE VI

Endoglin expression on endothelial cells in miscellaneous tumors

| Tumor type | n | anti-vWF | TEC-4 | TEC-11 |
|---|---|---|---|---|
| Angiosarcoma | 1 | +++[1] | +++ | +++ |
| Benign breast tumor | 6 | +++ | +/− | − |
| Breast carcinoma | 12 | +++ | ++ | ++/+++ |
| Cecum carcinoma | 1 | +++ | +++ | +++ |
| Colon carcinoma | 3 | +++ | ++ | +++ |
| Hodgkins disease | 11 | +++ | ++ | +++ |
| Lymphoma | 2 | +++ | +/− | + |
| Lung carcinoma | 1 | +++ | ++ | ++ |
| Melanoma | 1 | +++ | + | ++ |
| Osteosarcoma | 1 | +++ | + | ++ |
| Ovarian carcinoma | 1 | +++ | ++ | ++ |
| Parotid tumor | 3 | +++ | +++ | +++ |
| Pharyngeal carcinoma | 2 | +++ | ++ | ++ |
| Rectosigmoid carcinoma | 6 | +++ | ++/+++ | +++ |

[1]Staining intensity was strong (+++), moderate (++), weak (+) or negative (−).

b) Endothelial cells in normal tissues

Figure 17A:
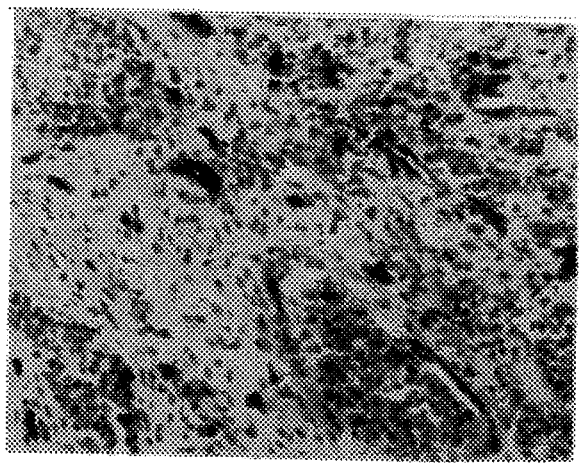
FIG. 17a. Immunohistochemical detection of TEC-4 binding to malignant human parotid tumor tissue. Numerous blood vessels are stained strongly by TEC-4 in a parotid tumor whereas only a single stained vessel is present in the adjacent normal glandular tissue (b,arrow). Antibody binding was detected with biotinylated F(ab')$_2$ rabbit anti-mouse Ig and SABC-HRP with AEC substrate and hematoxylin counterstaining; x 40.
Figure 17B:
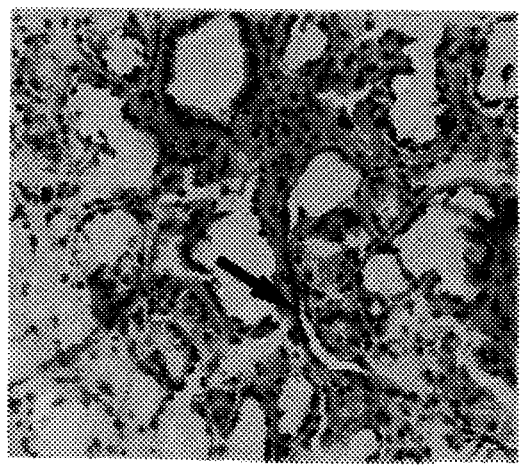
FIG. 17b. Immunohistochemical detection of TEC-4 binding to normal human glandular tissue. Only a single vessel is stained by TEC-4 in this normal glandular tissue (b,arrow). Antibody binding was detected with biotinylated F(ab')$_2$ rabbit anti-mouse Ig and SABG-HRP with AEC substrate and hematoxylin counterstaining; x 40.

A panel of 27 normal human tissues was used to assess the reactivity of TEC-4 and TEC-11 with vascular endothelial cells in non-malignant settings. The staining conditions used were ones that gave distinct staining of tumor vasculature. As shown in Table VII, the staining of normal endothelium obtained with both antibodies was usually weak or negative, but there was moderate staining of capillary endothelium in adrenal gland and placenta (both antibodies), parathyroid (TEC-4) and lung, cervix, testis, kidney and lymphoid organs (TEC-11). In addition, TEC-4 displayed strong binding to skin vessels (Table VII). Endothelial cells in numerous tissues showed no detectable staining with one or both antibodies, including bladder, brain, cranial nerve, mammary gland (FIG. 18b), ovary, pancreas, stomach, thymus and umbilical vein (FIG. 17d).

Several 'normal' tissue samples were in fact adjacent non-malignant tissue from cancer biopsies, enabling staining of endothelial cells in normal and malignant areas of the same organ to be compared in the same section. FIG. 17 (a and b) shows a sample of parotid tumor and associated histologically normal parotid gland where a marked difference in the staining of vascular endothelial cells by TEC-4 antibody is visible. In the stroma between the nests of malignant cells, all endothelial cells were heavily labelled (FIG. 17a). By contrast, only light staining of a single vessel in the normal glandular tissue was discernible (FIG. 17b).

TABLE VII

Endoglin expression on endothelial cells in non-neoplastic tissues

| Normal tissues | anti-vWF | TEC4 | TEC11 |
|---|---|---|---|
| Adrenal | +++[1] | ++ | ++ |
| Bladder | ++ | − | − |
| Brain cortex | ++ | − | − |
| Brain stem | ++ | − | − |
| Cerebellum | +++ | − | − |
| Colon | +++ | ++ | + |

TABLE VII-continued

Endoglin expression on endothelial cells in non-neoplastic tissues

| | Antibody | | |
|---|---|---|---|
| | anti-vWF | TEC4 | TEC11 |
| Cranial nerve | +++ | − | − |
| Gall bladder | +++ | ± | + |
| Kidney | +++ | ± | ± |
| Liver | +++ | + | + |
| Lung | +++ | ± | ++ |
| Mammary gland | +++ | − | − |
| Ovary | +++ | ± | − |
| Pancreas | + | − | − |
| Parathyroid | ++++ | ++ | − |
| Parotid gland | +++ | ± | ± |
| Placenta | +++ | ++ | ++ |
| Prostate | +++ | ± | ± |
| Salivary gland | +++ | ± | ± |
| Skin | +++ | +++ | + |
| Stomach | +++ | +/− | + |
| Stomach muscle | +++ | − | + |
| Testis | +++ | − | ± |
| Thymus | +++ | − | − |
| Thyroid | +++ | + | ± |
| Tonsil | +++ | + | + |
| Umbilical vein | +++ | +/− | +/− |
| Inflammatory tissues | | | |
| Tonsilitis | +++ | ++ | +++ |
| Reactive hyperplasia | +++ | +/− | + |
| Cat-scratch fever | +++ | + | ++ |
| Ulcerative colitis | +++ | ++ | +++ |

[1]Staining intensity was strong (+++), moderate (++), weak (+) or negative (−).

c) Endothelial cells during tumor progression in the breast

Figure 17C:
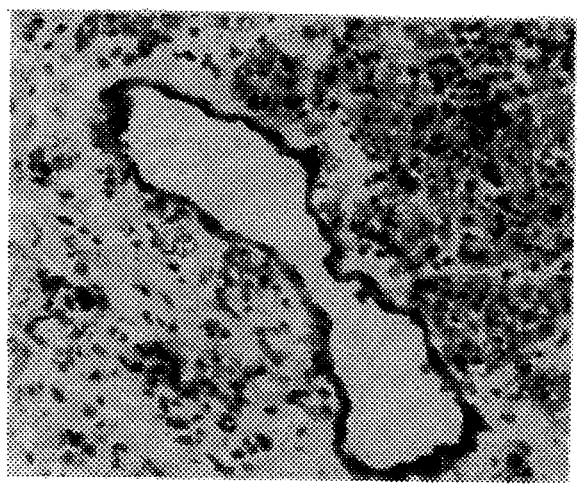
FIG. 17c. Immunohistochemical detection of TEC-4 binding to human breast carcinoma tissues. Under high power, endothelial cells in a breast carcinoma are strongly stained with TEC-4 whereas normal umbilical vein endothelial cells are weak-negative. Antibody binding was detected with biotinylated F(ab')$_2$ rabbit anti-mouse Ig and SABC-HRP with AEC substrate and hematoxylin counterstaining; x 64.
Figure 17D:
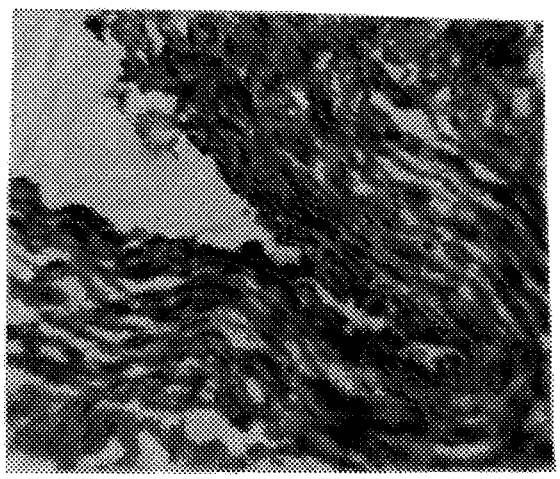
FIG. 17d. Immunohistochemical detection of TEC-4 binding to normal umbilical vein endothelial cells. Antibody binding was detected with biotinylated F(ab')$_2$ rabbit anti-mouse Ig and SABC-HRP with AEC substrate and hematoxylin counterstaining; x 20.
Figure 18A:
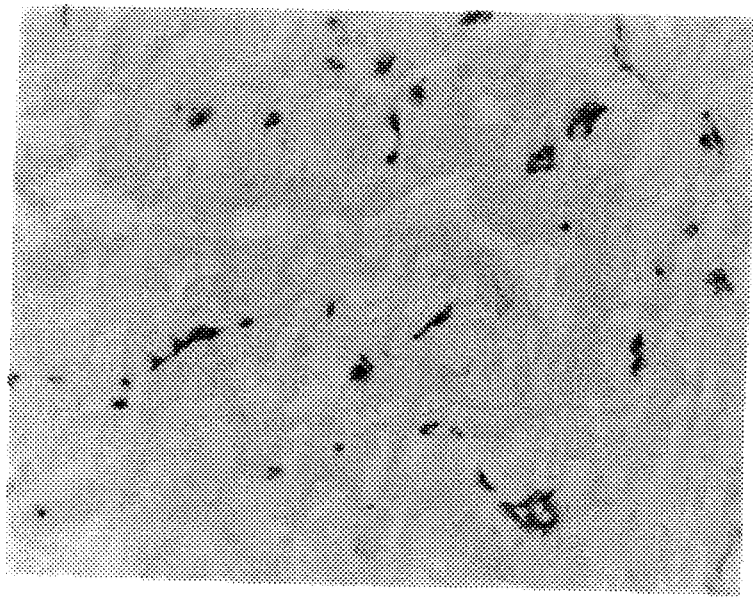
FIG. 18a. Differential TEC-4 binding to endothelial cells in normal breast tissue, control. Sections of normal mammary gland were stained with a control anti-endothelial cell antibody, F8/86 (anti-yon Willebrands Factor). Antibody binding was detected as in the legend to FIG. 16 except that DAB substrate was used and a light hematoxylin counterstaining was applied; x 20.
Figure 18B:
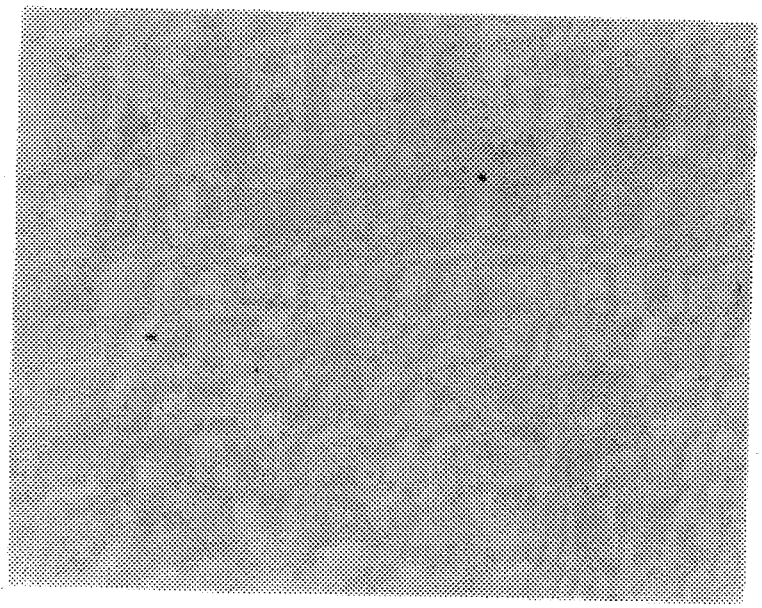
FIG. 18b. Differential TEC-4 binding to endothelial cells in normal breast tissue, TEC-4 control. Sections of normal mammary gland were stained with TEC-4. Binding of TEC-4 to normal endothelial cells is not seen. Antibody binding was detected as in the legend to FIG. 16 except that DAB substrate was used and a light hematoxylin counterstaining was applied; x 20.
Figure 18C:
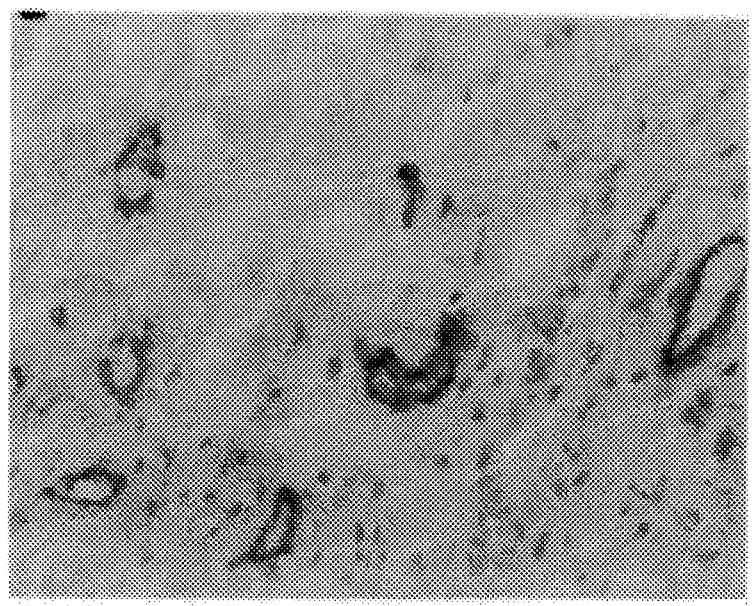
FIG. 18c. Differential TEC-4 binding to endothelial cells in malignant breast tissue, control. Sections of breast carcinoma were stained with a control anti-endothelial cell antibody, F§/86 (anti-yon Willebrands Factor). Antibody binding was detected as in the legend to FIG. 16 except that DAB substrate was used and a light hematoxylin counterstaining was applied; x 20.
Figure 18D:
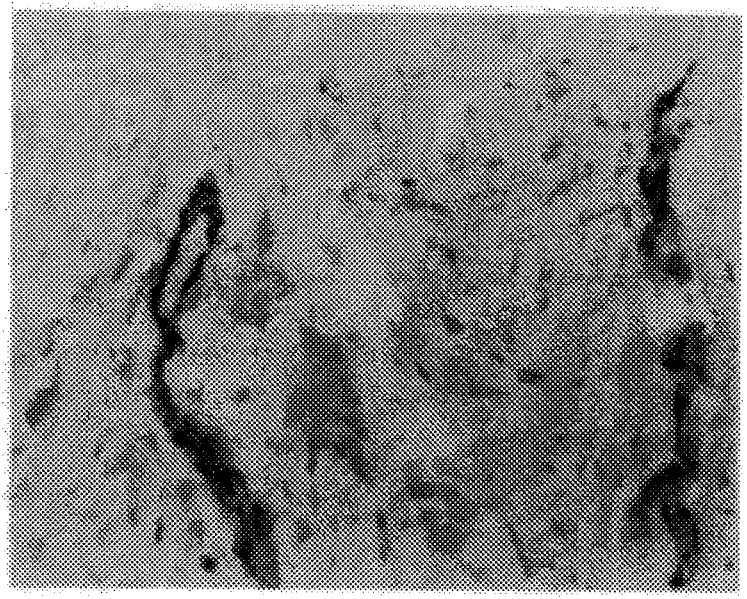
FIG. 18d. Differential TEC-4 binding to endothelial cells in malignant breast tissue, TEC-4. Sections of breast carcinoma were stained with TEC-4. Binding of TEC-4 to endothelial cells is only seen in the malignant breast sample. Antibody binding was detected as in the legend to FIG. 16 except that DAB substrate was used and a light hematoxylin counterstaining was applied; x 20.

Endothelial cells in normal mammary glands were not stained by either TEC-4 or TEC-11 (FIG. 18b) whereas endothelial cells in malignant breast tumors were stained moderately to strongly by both antibodies (FIG. 17c and Table VI). A series of abnormal breast tissues was therefore examined to determine at which stage of neoplastic progression endoglin expression was initiated. Vessels in 6/6 benign fibroadenomas displayed little or no reactivity with TEC-4 and TEC-11 (Table VI), as did those in low-grade hyperplastic lesions and early carcinoma-in-situ. Moderate staining was apparent in late-stage intraductal carcinomas whereas all vessels in frank malignant carcinomas were heavily labelled with both TEC-4 and TEC-11 (FIG. 17c, FIG. 18d, Table VI).

d) Endothelial cells in inflammatory sites

TEC-4 and TEC-11 staining of endothelial cells was strong in 3/4 types of inflammatory tissues examined (Table VII). TEC-11 staining was somewhat stronger than TEC-4 staining in all cases. In 6/8 cases of tonsillitis, cat-scratch fever and ulcerative coliris, which are all associated with neovascularization, endothelial cells were stained moderately to strongly with TEC-11. By contrast, vessels were weakly stained in 2 cases of reactive hyperplasia, a non-angiogenic condition.

e) Non-endothelial cells

Both TEC-4 and TEC-11 showed highly restricted binding to cryostat sections of normal and malignant human tissues, reacting primarily with vascular endothelial cells. However, both antibodies displayed cross-reactivities, typically quite weak, with certain non-endothelial cell types (Table VIII). Both antibodies bound weakly to stromal components in the prostate, the basal layer of seminiferous tubules, and to follicular dendritic cells in lymphoid organs and in small lymphold deposits associated with colorectal tumors (Table VIII). Strong staining of syncytiotrophoblast in placenta was also seen. TEC-11 gave a more restricted staining pattern than did TEC-4 (Table VIII), which also bound to myoepithelial cells in the breast, smooth muscle cells, especially in the gut, and to miscellaneous epithelial tissues including some rectal glandular epithelium, epidermis and breast carcinoma cells in a minority of samples.

8. Selective cytotoxic effects of TEC-11 immunotoxin

An immunotoxin was prepared by chemical linkage of TEC-11 antibody with deglycosylated ricin A-chain, as described in detail in Example II. The immunotoxin was tested for cytotoxicity against quiescent, confluent and subconfluent populations of human endothelial cells in a standard protein synthesis inhibition assay, as described in Example II. For comparison, the same endothelial cell cultures were also treated with an isotype-matched non-binding immunotoxin (MTSA-dgA), an immunotoxin against an endothelial cell antigen (ICAM-1) whose expression does not vary according to the growth status of the cells (UV-3-dgA) and native ricin.

Figure 19D:
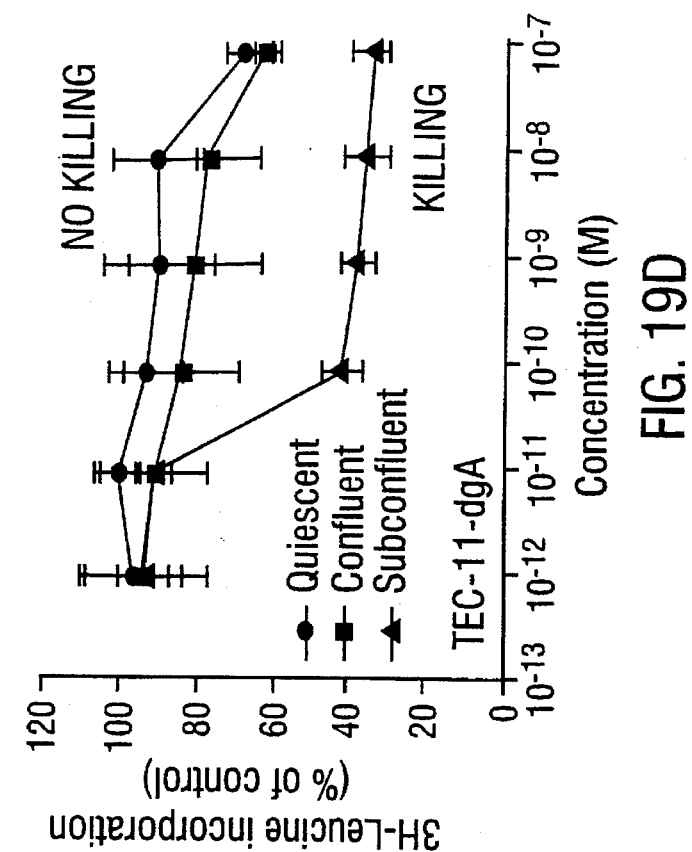
FIG. 19d. Significant killing of proliferating HUVEC by TEC-11dgA. Quiescent (●), confluent (■) or subconfluent (▲) HUVEC cultures were incubated for 48 hours with TEC-11dgA. Protein synthesis was estimated from the uptake of $^3$H-leucine during the last 24 hours of culture. Points and bars: mean and standard error of 6 individual studies.
Figure 19C:
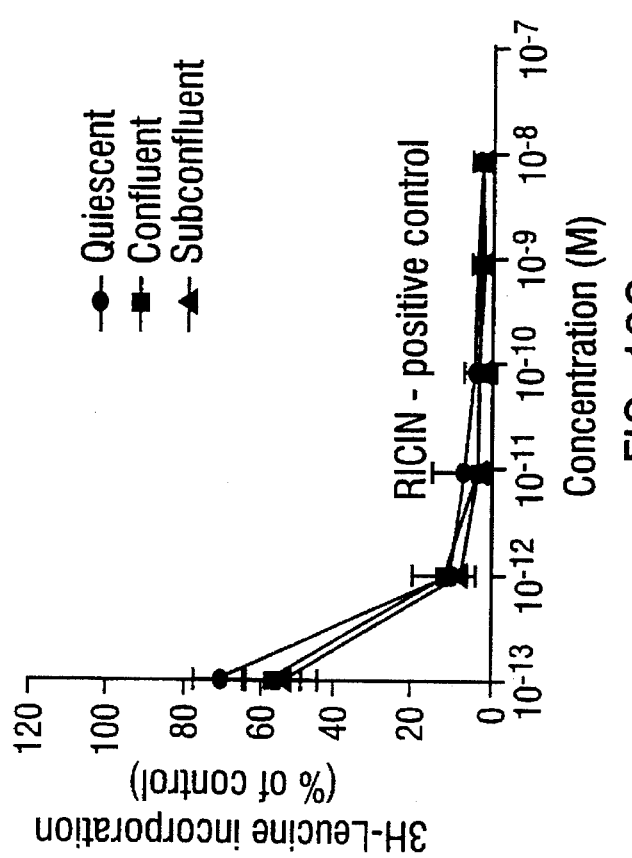
FIG. 19c. Significant killing of proliferating HUVEC by ricin. Quiescent (●), confluent (■) or subconfluent (▲) HUVEC cultures were incubated for 48 hours with ricin. Protein synthesis was estimated from the uptake of $^3$H-leucine during the last 24 hours of culture. Points and bars: mean and standard error of 6 individual studies.

The results of several such assays are combined and shown in FIG. 19 and Table IX. The negative and positive controls, MTSA-dgA (FIG. 19a) and ricin (FIG. 19c), respectively, gave essentially identical cytoxicity profiles against all three endothelial cell populations. Ricin inhibited protein synthesis by 50% ($IC_{50}$) in quiescent, confluent and subconfluent cultures at concentrations of 0.15–0.27 pM (FIG. 19c; Table IX) and MTSA-dgA displayed no cytotoxicity to any endothelial cell population at concentrations below 0.1 μm (FIG. 19a and Table IX).

The anti-ICAM-1 immunotoxin, UV-3-dgA, was weakly but clearly cytotoxic to endothelial cells at all stages of growth, with IC50 values ranging from 9 to 80 nM (FIG. 19b and Table IX). As expected from their higher metabolic rate and consequent requirements for protein synthesis, the proliferating subconfluent cultures were almost 9-fold more sensitive to UV-3dgA than were the quiescent cells (Table IX). The confluent cultures were fully metabolically active but were 4-fold less sensitive to UV-3-dgA than were the subconfluent cells (Table IX), probably reflecting decreased accessibility of the target antigen due to the dense packing of the cells in confluent cultures.

By contrast, TEC-11-dgA showed striking differences in cytotoxicity towards quiescent, confluent and subconfluent endothelial cells (FIG. 19d and Table IX). TEC-11-dgA at a concentration of 10–8M inhibited protein synthesis in quiescent cultures by only 10% and in confluent cultures by only 20%, (FIG. 19d) and yet inhibited protein synthesis in subconfluent cultures by over 60% at concentrations as low as $10^{-10}$M (FIG. 19d). When the $IC_{50}$ values for TEC-11-dgA towards the different endothelial cell cultures were compared, it was found that the immunotoxin was 2400-fold more toxic to subconfluent cells than to confluent cultures. When sparse and quiescent cells were compared, this ratio rose to over 3000 (Table IX).

Taken together, these results demonstrate that an immunotoxin prepared from the TEC-11 antibody displays highly selectively cytotoxicity towards subconfluent, actively proliferating human endothelial cells.

TABLE VIII

Reactivity of TEC-4 and TEC-11 with non-endothelial cells

| | | Antibody | |
|---|---|---|---|
| | Cell type | TEC-4 | TEC-11 |
| Tumor tissue | | | |
| Angiosarcoma | Sarcoma | ++ | ++ |
| Breast carcinoma | Carcinoma | + | − |
| | Myoepithelium | ++ | − |
| Colorectal carcinoma | Smooth muscle | +/++ | − |
| Hodgkins disease | Follicular dendritic cells | + | + |
| Various | Stroma | +/− | +/− |
| Normal tissue | | | |
| Gut | Smooth muscle | +/++ | − |
| Liver | Bile duct | + | − |
| Lymphoid tissues | Follicular dendritic cells | + | + |
| Mammary gland | Myoepithelium | ++ | − |
| Placenta | Syncltiotrophoblast | ++ | ++ |
| Prostate | Fibromuscular stroma | ++ | + |
| Skin | Epidermis | +/− | − |
| Testis | Basal layer of seminiferous tubules | + | + |

[1]Staining intensity was strong (+++), moderate (++), weak (+) or negative (−).

TABLE IX

Immunotoxin cytotoxicity to endothelial cells at different stages of growth.

| | IC$_{50}$ (nm) | | | IC$_{50}$ ratio | |
|---|---|---|---|---|---|
| | Quiescent (Q) | Confluent (C) | Subconfluent (S) | Q/S | C/S |
| Treatment | | | | | |
| MTSA-dgA | 80 | 160[1] | 45 | 1.8 | 3.6 |
| Ricin | 0.00027 | 0.00018 | 0.00015 | 1.8 | 1.2 |
| UV-3-dgA | 37 | 80 | 9 | 4.1 | 8.9 |
| TEC-11-dgA | 230[2] | 180[2] | 0.075 | 3067 | 2400 |

[1]Extrapolated by fitting an exponential curve to the graph shown in FIG. 19a.
[2]Extrapolated by fitting an exponential curve to the graph shown in FIG. 19d.

C. DISCUSSION

In this example, the inventors describe two new monoclonal antibodies, TEC-4 and TEC-11, directed against a marker that is upregulated in tumor-associated vascular endothelial cells. TEC-4 and TEC-11 specifically react with endoglin, which is known to be a proliferation-linked endothelial cell marker that is upregulated on dividing endothelial cells in vitro and on vascular endothelial cells in solid tumors, sites of chronic inflammation and fetal placenta in vivo.

HUVEC rapidly express endoglin after removal from the umbilical cord and establishment in tissue culture. Induction of the antigen was not diminished by depriving the cells of serum or growth factors or increased by addition of cytokines, such as IL-1, TNF-α and IFN-γ, known to activate endothelial cells (Dustin et al., 1986; Rice et al., 1990), in accordance with the findings of Westphal et al. (Westphal et al., 1993). The level of endoglin expression appeared to correlate with entry into or progression through the cell cycle. In HUVEC which had been grown to confluence, two subpopulations were present, one with low endoglin levels and the other with high expression. All endoglin$^{lo}$ cells were in G$_0$, but the endoglin$^{hi}$ population contained significant proportions of activated (G$_1$) and dividing (S+G$_2$M) cells, as indicated by increased levels of protein/RNA and DNA, respectively. The majority of endoglin$^{hi}$ cells were also in G$_0$, suggesting that cell surface endoglin is long-lived and is maintained at high levels in cells that have divided and subsequently enter a non-cycling state.

An association between increased endoglin expression and endothelial cell proliferation is also suggested by strong TEC-4/TEC-11 staining of blood vessels in sites of neovascularization. Moderate to strong labelling of most or all capillaries and venules was observed in cryostat sections of solid tumors of diverse histological types. The only malignant tumors that did not show significant endothelial cell staining were B-lymphomas, in keeping with the fact that lymphomas, unlike carcinomas and non-lymphoid sarcomas, grow by infiltrating existing vascular tracts rather than by inducing de novo blood vessel growth (Denekamp and Hobson, 1982). Endothelial cell staining was absent or weak in all normal healthy tissues examined other than placenta, where endothelial cells proliferate even faster than they do in tumors (Denekamp, 1986; Denekamp and Hobson, 1982). The inventors also observed endoglin upregulation in several cases of ulcerative colitis, a chronic inflammatory condition, and in cat-scratch fever and tonsillitis, which are associated with marked vascular proliferation (Garcia et al., 1990; Fujihara, 1991). By contrast, endoglin levels in reactive hyperplasia, which is not associated with angiogenesis (Jones et al., 1984), were not higher than in normal lymph nodes. Increased endoglin expression by vascular endothelial cells has also been reported in angiogenesis-dependent chronic inflammatory skin lesions, such as psoriasis, dermatitis and granulation tissue, and on one case of cutaneous malignant melanoma (Westphal et al., 1993). Increased endoglin expression appeared to be related to endothelial proliferation rather than to inflammation per se, because a range of inflammatory cytokines had little or no effect on endoglin levels in HUVEC in vitro (Westphal et al., 1993).

The reactivity patterns of TEC-4 and TEC-11 in frozen sections of human tissues and on human cells in vitro were similar to those of other anti-endoglin antibodies (Gougos and Letarte, 1988; Gougos et al., 1992; O'Connel et al., 1992; Bühring et al., 1991; Westphal et al., 1993). TEC-4 and TEC-11 bound to HUVEC and U937 cells in vitro, but were unreactive with the human lymphoma lines K562, CEM and Daudi, in accordance with previous reports (Gougos and Letarte, 1988; Westphal et al., 1993). All the antibodies labelled endothelial cells in miscellaneous human tissues and gave strong staining of fetal endothelium and syncytiotrophoblast in the placenta (Gougos et al., 1992; Westphal et al., 1993).

Several authors have reported stronger staining of endothelial cells in normal organs, especially kidney and liver (Gougos and Letarte, 1988; Westphal et al., 1993) and umbilical cord (Gougos and Letarte, 1988), than the inventors observed with TEC-4 and TEC-11. These discrepancies probably reflect differences in the sensitivity of the immunohistochemical staining techniques employed in different laboratories. In the present study, staining conditions were selected which produced clear staining of tumor endothelium whereas in previous studies (Gougos and Letarte, 1988; Gougos et al., 1992), more sensitive staining conditions were previously used in order to visualize normal endothelium. Evidence that this is indeed true is provided by our finding that 44G4, previously reported to stain normal endothelium, produced identical endothelial staining patterns to that described herein for TEC-4 and TEC-11 when the current techniques were employed. However, TEC-4 and TEC-11 recognize a distinct epitopes from that of 44G4, as shown by the failure of 44G4 to block TEC-4 or TEC-11, even at high ratios.

TEC-11 showed almost complete specificity for endothelial cells whereas TEC-4 also reacted moderately strongly with certain non-endothelial cells, particularly smooth muscle. The inventors interpret these additional reactivities of TEC-4 as being cross-reactivities possibly related to the low affinity of TEC-4. Similar staining of smooth muscle was frequently seen during the screening of the original hybridoma supernatants on tissue sections.

Upregulation of endoglin on vascular endothelial cells in solid tumors and chronic inflammatory disorders might be involved functionally in the regulation of angiogenesis in these pathological conditions. Recent evidence indicates that endoglin is an essential component of the TGF-β (transforming growth factor-β) receptor complex of human endothelial cells. It binds TGF-β1 and TGF-β3 with a $K_D$=50 pM (Cheifetz et al., 1992). TGF-β inhibits endothelial cell proliferation in vitro (Madri et al., 1992) but, paradoxically, is a potent angiogenic agent in vivo (Enenstein et al., 1992). Increased expression of endoglin by proliferating endothelial cells could modulate their response to TGF-β and hence regulate the angiogenic process (Cheifetz et al., 1992).

Antibodies to antigens other than endoglin have been reported to stain endothelial cells in miscellaneous neoplasms but not those in normal tissues. EN7/44 reacts with a predominantly intracellular antigen (Mr 30.5 kDa) in budding capillary sprouts in solid tumors and other neovascular sites whose expression appears to be linked to migration rather than proliferation (Hagemeier et al., 1986). FB-5 recognizes a heavily sialylated glycoprotein (Mr 170 kDa) on reactive fibroblasts and in a proportion of blood vessels in various human tumors (Rettig et al., 1992). E9 reacts with a 95 kD homodimer that is upregulated in tumors, fetal organs and regenerating tissues, but which can be distinguished from endoglin on the basis of lack of reactivity with placental endothelium and different staining of tumor-derived endothelial cells in vitro (Wang et al., 1993). Taken overall, the uniformity of staining of vessels in different tumors and within any individual tumor suggest that TEC-4 and TEC-11 compare favorably with these antibodies.

The TEC-4 and TEC-11 antibodies have important potential for diagnosis and therapy of human cancer. Firstly, the antibodies could be used to distinguish between histologically indistinct benign and malignant lesions. Studies in breast (Weidner et al., 1992; Horak et al., 1992), prostate (Bigler et al., 1993), bladder (Bigler et al., 1993), and cervical (Sillman et al., 1981) carcinomas have established that high vessel density or tumor angiogenic activity is strongly correlated with risk of metastasis and poor prognosis and so could be used to determine when aggressive post-operative therapy is appropriate (Weidner et al., 1992; Eorak et al., 1992). Diagnosis in these studies required laborious enumeration of capillaries labelled with pan-endothelial cell markers (Weidner et al., 1992; Horak et al., 1992; Bigler et al., 1993) or the use of complex and subjective in vivo assays of angiogenesis (Chodak et al., 1980), both of which might be supplanted by a simple immunohistochemical procedure employing TEC-4 or TEC-11. Indeed, the studies of breast tumors reported in this Example indicate that vascular endothelial cell expression of endoglin, as determined using TEC-4 or TEC-11, may distinguish between intraductal carcinoma in situ (CIS), an aggressive preneoplastic lesion and lobular CIS, which is associated with a more indolent clinical course.

Secondly, the antibodies could be used for imaging tumors in cancer patients. Being present on the luminal face of the endothelial cell, endoglin is ideally situated for antibody binding and should therefore permit rapid imaging. The antibodies would not be subject to the major limitation of imaging procedures against the tumor cells themselves, since they need not penetrate into solid tumor masses. In addition, being of the IgM isotype, extravasation of TEC-4 and TEC-11 should be minimal and their specific imaging of antigens in the intravascular compartment should be superior.

Thirdly, the antibodies could be used for therapy. The highly accessible location of endoglin on the luminal surface of the tumor vasculature is especially advantageous for therapeutic application, because all of the target endothelial cells are able to bind the therapeutic antibody, as shown in Example I. Both TEC-4 and TEC-11 are complement-fixing and so might induce selective lysis of endothelial cells in the tumor vascular bed. Also, the antibodies could be used to deliver therapeutic quantities of radioisotopes, toxins, chemotherapeutic drugs or coagulants to the tumor vasculature. Animal studies indicates that anti-tumor endothelial cell immunotoxins are most effective when combined with anti-tumor cell immunotoxins, which kill those tumor cells that have invaded surrounding normal host tissue (as disclosed hereinabove and in Burrows and Thorpe, 1993). Thus, TEC-4 or TEC-11 could be used clinically in combination with antibodies against well-characterized tumor markers such as $p185^{HER-2}$, TAG-72, and CO17-1A (Shepard et al., 1991; Greiner et al., 1991; Kaplan, 1989) or indeed with conventional chemotherapeutic drugs.

EXAMPLE V

Preparation, Characterization and Use of Antibodies Directed Against Tumor-Derived Endothelial Cell Binding Factors This example describes the generation of polyclonal and monoclonal antibodies directed against tumor-derived endothelial cell "binding factors" for use in distinguishing between tumor vasculature and the vasculature of normal tissues. Particularly described is the generation of antibodies directed against vascular permeability factor (VPF), also termed vascular endothelial cell growth factor (VEGF), and against bFGF (basic fibroblast growth factor).

For further details concerning FGF one may refer to Gomez-Pinilla and Cotman (1992); Nishikawa et al. (1992), that describe the localization of basic fibroblast growth factor; Xu et al. (1992), that relates t6 the expression and immunochemical analysis of FGF; Reilly et al. (1989), that concerns monoclonal antibodies; Dixon et al. (1989), that relates to FGF detection and characterization; Matsuzaki et al. (1989), that concerns monoclonal antibodies against heparin-binding growth factor; and Eerbin and Gross (1992), that discuss the binding sites for bFGF on solid tumors associated with the vasculature.

In these studies, rabbits were hyperimmunized with N-terminal peptides of human VEGF, mouse VEGF, guinea pig VEGF, human bFGF, mouse bFGF or guinea pig bFGF coupled to tuberculin (purified protein derivative, PPD) or thyroglobulin carriers. The peptides were 25 to 26 amino acids in length and were synthesized on a peptide synthesizer with cysteine as the C-terminal residue. Antisera were affinity purified on columns of the peptides coupled to Sephraose matrices.

Antibodies to VEGF were identified by ELISA and by their staining patterns on frozen sections of guinea pig tumors and normal tissues. Polyclonal antibodies to guinea pig VEGF and human VEGF reacted with the majority of vascular endothelial cells on frozen sections of guinea pig L10 tumors and a variety of human tumors (parotid, ovarian, mammary carcinomas) respectively. The anti-human VEGF antibody stained mesangial cells surrounding the endothelial cells in normal human kidney glomerulae and endothelial cells in the liver, but did not stain blood vessels in normal human stomach, leg muscle and spleen. The anti-guinea pig VEGF antibody did not stain endothelial cells in any normal tissues, including kidney, brain, spleen, heart, seminal vesicle, lung, large intestine, thymus, prostrate, liver, testicle and skeletal muscle.

Polyclonal antibodies to human FGF stained endothelial cells in parotid and ovarian carcinomas, but not those in mammary carcinomas. Anti-human FGF antibodies stained glomerular endothelial cells in human kidney, but not endothelial cells in normal stomach, leg muscle and spleen.

Monoclonal antibodies to guinea pig VEGF, human VEGF and guinea pig bFGF were prepared by immunizing BALB/c mice with the N-terminal sequence peptides (with cysteine at the C-terminus of the peptide) coupled to PPD or to thyroglobulin. The synthetic peptides immunogens of defined sequence are shown below and are represented by SEQ ID NO:1, SEQ ID NO:2 AND SEQ ID NO:3, respectively:

guinea pig VEGF    A P M A E G E Q K P R E V V K F M D V Y K R S Y C
human VEGF         A P M A E G G G Q N H H E V V K F M D V Y Q R S Y C
guinea pig bFGF    M A A G S I T T L P A L P E G G D G G A F A P G C The peptides were conjugated to thyroglobulin or to PPD by derivatizing the thyroglobulin with succimidyl 4-(N-maleimidomethyl)cyclohexane-1-carboxylate (SMCC) and reacting the derivative with the peptide. This yields a conjugate having one or more peptide sequences linked via a thioether bond to thyroglobulin.

Specifically, the generation of monoclonal antibodies against the above sequences was achieved using the following procedure: BALB/c mice were immunized by serial injections with peptide-PPD or peptide-thyroglobulin into several sites. Four or five days after the last injection, the spleens were removed and splenocytes were fused with P3xG3AgS.653 myeloma cells using polyethyleneglycol according to the procedures published in Morrow, et al. (1991). Individual hybridoma supernatants were screened as follows:

First screen: ELISA on peptide-thyroglobulin-coated plates.
Second screen: ELISA on cysteine linked via SMCC to thyroglobulin.
Third screen: Indirect immunoperoxidase staining of frozen sections of guinea pig line 10 tumor or human parotid carcinoma.
Fourth screen: Indirect immunoperoxidase staining of frozen sections of miscellaneous malignant and normal guinea pig and human tissues.

Antibodies were selected that bound to peptide-thyroglobulin but not to cysteine-thyroglobulin, and which bound to endothelial cells in malignant tumors more strongly than they did to endothelial cells in normal tissues (Table X).

TABLE X

Reactivity of Monoclonal Antibodies

| MoAB | Immunogen+ | Class | Reactivity with Tumor Endothelium g. pig | Reactivity with Tumor Endothelium human | Tumor Reactivity Pattern* |
|---|---|---|---|---|---|
| GV14 | gp VEGF | IgM | + | + | BV + some tumor cells |
| GV35 | gp VEGF | IgM | ± | ± | Tumor cells, weak on BV |
| GV39 | gp VEGF | IgM | + | + | BV and some tumor cells |
| GV59 | gp VEGF | IgM | + | + | BV and some tumor cells |
| GV97 | gp VEGF | IgM | + | + | BV, weak on tumor cells |
| HV55 | hu VEGF | IgG | ? | + | Basement membrane, some BV |
| GF67 | gp FGF | IgM | + | + | BV and tumor cells |
| GF82 | gp FGF | IgM | + | + | BV and tumor cells |

*BV = blood vessels
+gp = guinea pig
hu = human
GV97 Staining of Human and Guinea Pig Tissue Sections The GV97 antibody against guinea pig VEGF N-terminus bound to endothelial cells in miscellaneous human malignant (Table XI) and normal (Table XII) tissues.

Binding to endothelial cells in malignant tumors tended to exceed that to endothelial cells in normal tissues; however, this difference was not striking.

The staining of endothelial cells in guinea pig tumor (line 10 hepatocellular carcinoma) and normal tissues was similar in distribution and intensity to that observed with human tissues (Table XIII).

In Tables XI through XV, + indicates a positive, as opposed to a negative, result. The numbers 2+, 3+ and 4+ refer to a positive signal of increasing strength, as is routinely understood in this field of study.

TABLE XI

Anti-GPVEGF on Human Tumors

| Tumor TISSUE | Purified GV97 20 ug/ml | 10 ug/ml | 5 ug/ml | 1 ug/ml or 2 ug/ml | 0.5 ug/ml | GV97 supt. | GV14 | GV39 | GV59 supt. |
|---|---|---|---|---|---|---|---|---|---|
| DIGESTIVE TRACT | | | | | | | | | |
| 92-01-A073 esophagus carcinoma | | 2+ | 1+ | +/− | −ve | | | 4+ | 4+ |
| M4 Parotid | | | | | | 4+ | | | |
| 87-07-A134 Parotid carcinoma | | 3+ | 2+ | +/− | −ve | | | 3+ | 4+ |
| 88-04-A010 parotid adenoca. | | 1−2+ | 1+ | −ve | −ve | | | | 1−3+ |
| 90-11-B319 Adeno. Ca. of colon to liver | | | | | | 3−4+ | | 3−4+ | |
| 94-02-B021C Adenocarcinoma of colon | | | | | | 3−4+ | | 3−4+ | |
| 93-10-A333 Adeno. Ca. of colon with normal | 4+ | 2−4+ | 1−4+ | −ve−1+ | | 4+ | | | 3+ |
| 93-02-B004 Villous and Adenomatous polyp of colon | 4+ | 3−4+ | 2−4+ | 1−2+ | | 3−4+ | | 2−3+ | |
| 93-02-A130 Leiomyosarcoma in colon | | 3+ | 2+ | +/−−1+ | −ve | 4+ | | 4+ | 3−4+ |
| 93-02-B020 Gastric Ca. | | 4+ | 2+ | 2−3+ | −ve−1+ | | | 1−2+ | 4+ |
| 93-04-A221 Pancreas Adenoca. | | 3−4+ | 2−3+ | 1−2+ | −ve−0.5+ | | | 4+ | 4+ |
| 93-04-A390 rectum adenoca. | | 4+ | 3+ | 1−2+ | 1+ | | | | 3+ |
| 93-12-A160 tongue carcinomaadenoca. | | 1−2+ | +/− | −ve | −ve | | | 3+ | 3+ |
| 101-84a Stomach signet ring Ca. (101-84B pair) | | 3+ | 2+ | −ve−1+ | −ve | most 1−2+ but a few 3−4+ | | | 3+ |
| 90-05-A172 Stomach Adenoca. | | 4+ | 3+ | 1−2+ | −ve−1+ | | | −ve | 3+ |
| REPRODUCTIVE TRACT | | | | | | | | | |
| 91-10-A115 Squam. cell Ca. of vulva | 1−4+ | 1−3+ | 1−2+ | 1−2+ | | 1−4+ | | | 1−3+ |
| 93-03-A343 Prostate Adenoca. | | +/− − 3−+ | +/− to 1−2−3+ | +/− to 1−2+ | +/− | | | 3−4+ | 3−4+ |
| MUSCLE | | | | | | | | | |
| IMMUNE SYSTEM | | | | | | | | | |
| URINARY SYSTEM | | | | | | | | | |
| 93-10-B002 Renal cell Ca. | | | | | | 2+ | | | 3+ |
| 90-01-A225 Renal cell Ca. | | 4+ | 4+ | 3−4+ of most | 1−3+ of some | 3−4+ | | 3+ | 3−4+ |
| 93-01-A257 Transit. cell Ca. of bladder | 3−4+ | 2−3+ | 1−2+ | +/− | | 2−3+ | | | 2−3+ |
| ENDOCRINE SYSTEM | | | | | | | | | |
| 94-01-A246 Pheochromocytoma of adrenal | 4+ | 4+ | 3−4+ | 3+ | | 4+ | | | 3−4+ |
| 93-11-A074 Adrenal Cort. Ca. | 3−4+ | 3−4+ | 2−3+ | 1+ | | 3−4+ | | | 4+ |
| RESPIRATORY SYSTEM | | | | | | | | | |
| 93-08-N009 Lung Adenoca. | | | | | | 3−4+ | | 3−4+ | 3−4+ |
| 92-10-A316 Sq. cell lung Ca. | | 4+ | 3−4+ | 1−2+ | −ve−0.5+ | | | 4+ | 4+ |
| 03-05-A065 Lung adenoca. | | 4+ | 3−4+ | −ve−1+ | 1+ | | | 3+ | 3+ |
| CENTRAL NERVOUS SYSTEM | | | | | | | | | |
| 94-01-A299 malig. metast. schwanoma to Lymph node | 4+ | 4+ | 4+ | 3−4+ | | 4+ | | | 3−4+ |

TABLE XI-continued

Anti-GPVEGF on Human Tumors

| Tumor TISSUE | Purified GV97 | | | | | GV97 supt. | GV14 | GV39 | GV59 supt. |
|---|---|---|---|---|---|---|---|---|---|
| | 20 ug/ml | 10 ug/ml | 5 ug/ml | 1 ug/ml or 2 ug/ml | 0.5 ug/ml | | | | |
| 92-10-A139 Meningioma | 4+ | 3-4+ | 2-3+ | 1-2+ | | 4+ | | | 3-4+ |
| 91-12-A013 Meningioma | 4+ | 2-3+ | -ve-3+ | +/- | | 4+ | | | 3+ |
| 93-03-A361 Atypical meningioma | | 4+ | 4+ | 3+ | 2+ | 4+ | | | 3+ |
| INTEGUMENTARY SYSTEM | | | | | | | | | |
| 94-04-V037 Skin Sq. cell ca. w/normal | | -ve to 4+ | -ve to 3+ | -ve to 1+ | -ve | | | 2-3+ | 2-3+ |
| 89-02-225 leg sarcoma | | 4+ | 3-4+ | 1+ | 1+ | | | 4+ | 2+ |
| MISC. TUMORS | | | | | | | | | |

TABLE XII

Anti-GPVEGF on Human Normal Tumors

| Tumor TISSUE | Purified GV97 | | | | | GV97 supt. | GV14 | GV39 | GV59 supt. |
|---|---|---|---|---|---|---|---|---|---|
| | 20 ug/ml | 10 ug/ml | 5 ug/ml | 1 ug/ml or 2 ug/ml | 0.5 ug/ml | | | | |
| DIGESTIVE SYSTEM | | | | | | | | | |
| 91-01-A128 Bladder w/ cystitis | | 3+ | 2+ | 1+ | -ve | | | 2-3+ | 2-3+ |
| 94-02-B020 uninvolved colon | | | | | | 2-3+ | | 2-3+ | |
| 92-01-A292 N. Colon | 4+ | 4+ | 4+ | 3-4+ | | 4+ | | | 3-4+ |
| 93-10-A116 N. Colon | 2-4+ | 1-4+ | 1-3+ | -ve-2+ | -ve | 3-4+ | | 2-3+ | 3-4+ |
| 90-06-A116 N. colon | | | | | | 3+ of many | | 2+ | |
| 93-02-A350 N. esophagus | | 3-4+ | 3+ | 1+ | +/- | | | 4+ | 4+ |
| 93-05-A503 N. Ileum | | | | | | 4+ | | | 4+ |
| 94-03-A244 N. Liver | | 4+ | 1-3+ | -ve-1+ | -ve | | | 4+ | 4+ |
| 90-02-B132 N. Liver | 1+ of a few | +/- | -ve | -ve | -ve | 1-3+ | 2-3+ | 2-3+ | 2-3+ |
| 94-01-A181 N. Pancreas | | 1-4+ | 1-3+ | 1-3+ of a few | -ve | | | | 3-4+ |
| 90-05-D008 N. Pancreas | | 2-4+ | 1-3+ | +/- | -ve | | | 2-3+ | 2-3+ |
| 93-05-A174 N. Parotid | | 2+ of a few | 1-2+ of a few | 1+ of a few | -ve | -ve | | 3+ of a few | 2-3+ |
| 94-04-A391 N. Small bowel | | 1-3+ | -ve-2+ | -ve | -ve | | | | 3+ |
| 88-06-107 N. Stomach | 3+ | 2+ | +/- | -ve | | 3-4+ | | | 3+ |
| 101-84b N. Stomach (101 = 84a pair) | | 3-4+ in main and periphery | 2-3+ in main and 3-4+ in periphery | +/- in main and 2+ in periphery | -ve in main and 1+ in periphery | 3+ | | | 3-4+ |
| 90-11-B337 N. Stomach | | 2-3+ | +/- -1+ | -ve | -ve | | | 3+ | 3+ |
| REPRODUCTIVE TRACT | | | | | | | | | |
| 93-04-A041 N. Breast | | | | | | 4+ | | 3+ | |
| 94-02-A197 N. Breast w/fibrocystic change | | | | | | 4+ | | 3+ | |
| 93-02-A051 Breast w/fibrocystic change | | -ve-1+ | -ve | -ve | -ve | | | +/- | +/- -2+ |
| 93-02-A103 Breast | 4+ | 3+ | 2+ | 1+ | | | | | |

TABLE XII-continued

Anti-GPVEGF on Human Normal Tumors

| Tumor TISSUE | 20 ug/ml | Purified GV97 10 ug/ml | 5 ug/ml | 1 ug/ml or 2 ug/ml | 0.5 ug/ml | GV97 supt. | GV14 | GV39 | GV59 supt. |
|---|---|---|---|---|---|---|---|---|---|
| w/fibrocyst. change | | | | | | | | | |
| 92-11-A006 N. ectocervix | 2+ of most | 1–2+ of most | 0.5+ | –ve | –ve | 1–2+ of some | | | 3+ of most |
| 91-03-A207 N. ectocervix | | 2.5+ | 1.5+ | 1+ | .5+ | | | | 2–3+ |
| 92-02-A139 N. ovary w/corp. lusteum | 1+ in most but 2+ in one area | –ve in most but 1+ in one area | –ve | –ve | | –ve in most but 3–4+ in one area | | | –ve in most bet 3–4 in one area |
| 93-06-A11B N. Prostate | | 1+ of a few | –ve | –ve | –ve | | | | 3+ |
| 93-11-A317d Prostate chip | | 3–4+ | 2–3+ | –ve–3+ | –ve–1+ | | | 3–4+ | 3–4+ |
| 93-02-A315 Seminal Vesicle | | 0.5–1+ | 0.5+ | –ve | –ve | | | 1+ | 1.2+ |
| 92-04-A069 N. testis | | 1+ | +/– | +/– | +/– | | | 1–2+ | |
| 91-04-A117 Ureter w/inflammation | | 1+ | +/– | –ve | –ve | | | +/– –1+ | 3–4+ |
| MUSCLE | | | | | | | | | |
| 94-01-A065 N. Heart | | 3–4+ | 2+ | +/– | –ve | | | 3–4+ | 4+ |
| 91-07-D007 N. skeletal muscle | 1–4+ | 1–3+ | 1–2+ | –ve | –ve | 1–3+ | | | 1–3+ |
| 95-03-A395 N. Skeletal muscle | | 4+ | 3–4+ | 1–2+ | 0.5–1+ | | | 4+ | 4+ |
| IMMUNE SYSTEM | | | | | | | | | |
| 90-01-A077 N. lymph node | 2–3+ | 2+ | 1+ of some | –ve | –ve | 2–3+ | | | 3–4+ |
| 90-08-A022 N. lymph node | | most 1+ but a few 4+ | most 0,5+ but a few 2+ | most –ve but a few 2+ | most –ve but a few 0.5–1+ | | | 3+ | 3+ |
| 91-03-A057 N. lymph node | | 2+ | 1+ | +/– | –ve | | | 3–4+ | 3–4+ |
| 91-09-B017E uninvolved lymph node | | 3+ | 2+ | +/– –1+ | –ve | | | 2–3+ | 2–3+ |
| 93-07-A236 N. Spicen | | 3–4+ | 3–4+ | –ve–3+ | –ve | | | | 2–4+ |
| 93-07-252 N. spicen | | 3+ | 1+ | +/– | –ve | | | 2–3+ | |
| ENDOCRINE SYSTEM | | | | | | | | | |
| 94-04-A252 N. adrenal w/ medulia and cortex | 4+ | 4+ | 3–4+ | 1–2+ | | 4+ | | 3+ | |
| 93-05-A086 N. Adrenal medulla | | most –ve a few 1–2+ | most –ve a few 1–2+ | –ve | –ve | | | 2–3+ | 3–4+ |
| 92-03-A157 Hyperplasic thyroid | | 1+ | +/– | +/– | –ve | | | 4+ | 4+ |
| 91-03-B019 N. Thyroid | | –ve–3+ | –ve–2+ | –ve–1+ | –ve | | | 2–3+ | 2–3+ |
| URINARY SYSTEM | | | | | | | | | |
| 93-09-A048 N. Kidney | | | | | | 4+ | | | 2–3+ |
| 91-11-A075 N. Kidney | | 4+ | 3+ | 2+ | 1+ | 4+ on glomeruli | | 4+ on glomeruli | 4+ on glomeruli |
| 93-10-B001 N. Kidney | | 4+ | 3+ | +/– | –ve | 4+ on glomeruli | | 4+ on glomeruli | 4+ on glomeruli |
| INTEGUMENTARY SYSTEM | | | | | | | | | |
| 92-08-A029 N. Breast skin | | +/– to 4+ | +/– to 3+ | +/– to 1+ | +/– | | | 2+ | 2+ |
| 89-02-257 cartilage | | 4+ | 3–4+ | 2–3+ | 1–2+ | | | 1+ | 3–4+ |

TABLE XII-continued

Anti-GPVEGF on Human Normal Tumors

| Tumor TISSUE | Purified GV97 | | | | | GV97 supt. | GV14 | GV39 | GV59 supt. |
|---|---|---|---|---|---|---|---|---|---|
| | 20 ug/ml | 10 ug/ml | 5 ug/ml | 1 ug/ml or 2 ug/ml | 0.5 ug/ml | | | | |
| marches 2SS | | | | | | | | | |
| RESPIRATORY SYSTEM | | | | | | | | | |
| 93-05-A203 N. Lung | | –ve–2+ | –ve–1+ | +/– | –ve | | | 2+ | 3+ |
| 92-12-A263 N. Bronchus | | 2–3+ w/ducts staining 3–4+ | 1–2+ w/ ducts staining 2–3+ | –ve | –ve | | | | 2–3+ |

TABLE XIII

Staining Pattern of 9F7 anti-VEGF by direct immunohistochemical staining on 6–8 week old GP tissues

| TISSUE | Purified GV97 | | | | | 9F7 supt. | 3F9 supt. | 5F9 supt. |
|---|---|---|---|---|---|---|---|---|
| | 20 ug/ml | 10 ug/ml | 5 ug/ml | 1 ug/ml or 2 ug/ml | 0.5 ug/ml | | | |
| DIGESTIVE SYSTEM | | | | | | | | |
| LIVER | | 2+ | 1–2+ | +/– | +/– | | 1–2+ | 1–2+ |
| INTESTINE | 4+ | 3+ | 2+ | 1+ | | | 4+ m lymphoid, rest diff. than | 4+ m lymphoid, rest diff. than |
| PANCREAS | 1+ of many and 3+ in islands of cells | | | | | | | |
| SMALL INTESTINE | 4+ of many and 4+ in lymphoid | 2–3+ of many and 4+ in lymphoid, rest diff. than fVIII | 1–2+ of many many and 4+ in lymphoid, rest diff. than fVIII | +/– of many and 4+ in lymphoid, rest diff. than fVIII | | | 3+ of some and 4+ in lymphoid | 3+ of some and 4+ in lymphoid |
| STOMACH | 3–4+ | 1–2+ on most occasional 3+ | +/– on most occasional 2+ | +/– on most occasional 1+ | | | 3–4+ (some fVIII-ve) | 3+ of some fVIII-ve) |
| REPRODUCTIVE SYSTEM | | | | | | | | |
| TESTIS | | | | | | | | |
| MUSCLE AND INTEGUMENTARY SYSTEM | | | | | | | | |
| HEART | –ve | –ve | –ve | –ve | | | 3–4+ (some fVIII-ve) | 3–4+ (some fVIII-ve) |
| MUSCLE | | | | | | | | |
| SKIN | 1–2+ in fatty layer and 3–4+ in cellular layer | 1+ in fatty layer and 3–4+ in cellular layer | +/– in fatty layer and 3–4+ of a few in cellular layer | +/– in fatty layer and 1–2+ of a few in cellular layer | | | 3+ | 3+ |
| IMMUNE SYSTEM | | | | | | | | |
| SPLEEN | 4+ | 3+ | 2+ | –ve | | | 4+ | 4+ |
| THYMUS | | | | | | | | |
| URINARY SYSTEM | | | | | | | | |
| KIDNEY | glomeruli 4+ | glomeruli 3–4+ | glomeruli 2–3+ | glomeruli 1–2+ | | | glomeruli 3–4+ | glomeruli 3–4+ |
| ENDOCRINE SYSTEM | | | | | | | | |
| ADRENAL | | | | | | | | |
| RESPIRATORY SYSTEM | | | | | | | | |
| LUNG | | | | | | | | |
| NERVOUS SYSTEM | | | | | | | | |

TABLE XIII-continued

Staining Pattern of 9F7 anti-VEGF by direct immunohistochemical staining on 6-8 week old GP tissues

| TISSUE | Purified GV97 | | | 1 ug/ml or | | | | |
|---|---|---|---|---|---|---|---|---|
| | 20 ug/ml | 10 ug/ml | 5 ug/ml | 2 ug/ml | 0.5 ug/ml | 9F7 supt. | 3F9 supt. | 5F9 supt. |
| CEREBELLUM | 4+ | 2+ | +/− of most and 1+ of a few | +/− of most and 1+ of a few | | | 4+ | 4+ |
| TUMORS | | | | | | | | |
| TUMOR | 4+ | 4+ | 3–4+ | 2–3+(2) | | 4+ | | 3+ |

Lack of Reactivity of GV97 With Soluble Human VEGF

GV97 did not bind to recombinant VEGF-coated ELISA plates, nor did recombinant human VEGF bind to GV97 coated ELISA plates. Soluble recombinant human VEGF did not block the binding of 5 µg/ml GV97 to tumor endothelium in histological sections even when added at 50 µg/ml.

These data suggest that GV97 recognizes an epitope of VEGF that is concealed in recombinant human VEGF but which becomes accessible when VEGF binds to its receptor on endothelial cells.

GV97 Localization After Injection in Line 10-Bearing Guinea Pigs

In contrast with staining data obtained from histological sections, GV97 antibody localized selectively to tumor endothelial cells after injection into line 10 tumor-bearing guinea pigs (Table XIV). Staining of endothelial cells in the tumor was moderately strong whereas staining of normal endothelium in miscellaneous organs was undetectable.

Anti-bFGF Antibodies Selectively Bind to Tumor Endothelial Cells

GV97 and GF82, which had been raised against guinea pig bFGF N-terminus, bound strongly to endothelial cells in frozen reactions of guinea pig line 10 tumor and to endothelial cells in two types of human malignant tumors (Table XV). By contrast, relatively weak staining of endothelial cells in miscellaneous guinea pig normal tissues was observed.

TABLE XIV

| | GV97 injected into tumor bearing GP | |
|---|---|---|
| TISSUE | GV97 10 ug/ml | GV 97 20 ug/ml serum volume injected |
| DIGESTIVE SYSTEM | | |
| LIVER | 2+ | −ve |
| INTESTINE | 3+ | possible 0.5–1+ of a few |
| PANCREAS | +/− of many and 2+ in islands of cells | possible 0.5–1+ of a few |
| SMALL INTESTINE | 2–3+ of many and 4+ in lymphoid, rest diff. than fVIII | +/− |
| STOMACH | 1–2+ on most occasional 3+ | possibly 0.5+ of a few |
| REPRODUCTIVE SYSTEM | | |
| TESTIS | | +/− |
| MUSCLE AND INTEGUMENTARY SYSTEM | | |
| HEART | −ve | −ve |
| MUSCLE | | −ve |
| SKIN | 1+ in fatty layer and 3–4+ in cellular layer | |
| IMMUNE SYSTEM | | |
| SPLEEN | 3+ | possibly a few 1+ |
| THYMUS | | |
| URINARY SYSTEM | | |
| KIDNEY | glomeruli 3–4+ | |

TABLE XIV-continued

GV97 injected into tumor bearing GP

| TISSUE | GV97 10 ug/ml | GV 97 20 ug/ml serum volume injected |
|---|---|---|
| ENDOCRINE SYSTEM | | |
| ADRENAL | 4+ | –ve |
| RESPIRATORY SYSTEM | | |
| LUNG | 2+ | –ve |
| NERVOUS SYSTEM | | |
| CEREBELLUM | 2+ | –ve |
| TUMORS | | |
| TUMOR | 4+ | 2–3+ |

TABLE XV

Anti-GP FGF Antibody Staining on GP Tissues

| GP TISSUE | GF 67 | GF 82 |
|---|---|---|
| DIGESTIVE SYSTEM | | |
| LIVER | ND | ND |
| INTESTINE | +/– | +/– |
| PANCREAS | 2–3+ | 2+ |
| SMALL INTESTINE | +/– | +/– |
| STOMACH | ND | ND |
| REPRODUCTIVE SYSTEM | | |
| TESTIS | ND | ND |
| MUSCLE AND INTEGUMENTARY SYSTEM | | |
| HEART | 2–3+ | 1+ |
| MUSCLE | +/– | 1+ |
| SKIN | ND | ND |
| IMMUNE SYSTEM | | |
| SPLEEN | 3+ | –ve |
| THYMUS | | |
| URINARY SYSTEM | | |
| KIDNEY | 1–2+ | –ve |
| ENDOCRINE SYSTEM | | |
| ADRENAL | 1–2+ | +/– |
| RESPIRATORY SYSTEM | | |
| LUNG | 1–2+ | 2–3+ |
| NERVOUS SYSTEM | | |
| CEREBELLUM | 1+ | –1+ |
| TUMORS | | |
| LINE 1 TUMOR | 4+ | 4+ |
| HUMAN TUMORS | | |
| PHEOCHROMO CYTOMA | 4+ | 4+ |
| SCHWANOMA | 4+ | 4+ |

EXAMPLE VI

Thrombosis of Line 10 Tumor Vasculature by Administration of GV97-ricin A-chain Immunotoxin to Guinea Pigs This example describes the effects observed following the administration of GV97-ricin A-chain immunotoxin to guinea pigs in vivo.

GV97 was conjugated to deglycosylated ricin A-chain using previously published methods (Thorpe et al., 1988). Guinea pigs having a 2 cm diameter subcutaneous line 10 tumor were injected intravenously with 700 µg/kg of this immunotoxin. The tumor and various normal tissues were removed 24 hours after injection. Killing of endothelial cells throughout the tumor plus thrombosis of the tumor vasculature was apparent. No damage to any normal tissues was observed. The effect was specific; no damage to tumor endothelium was observed in recipients of a class-matched (IgM) immunotoxin of irrelevant specificity.

It is important to note that no toxicity to the guinea pigs was observed. The treated animals maintained normal appearance, activity, and body weight.

REFERENCES

The following references are hereby incorporated herein by reference, to the extent that they explain, further enable, provide a basis for or describe the subject matter to which is referred to in the specification.

Abrams, P. W. et al. (1985) *Monoclonal antibody therapy of human cancer* (Foon and Morgan, eds.), Martinus Nijhoff Publishing, Boston, pp. 103–120.
Anegon, I. (1988) *J. Exp. Med.* 167(2):452–472.
Ausubel et al. (1989) Current Protocols in Molecular Biology, Greene Publishing Associates and Wiley Interscience, N.Y.
Bauer, T. et al., (1991) *Vox Sang,* 61:156–157.
Baxter, L. T. et al. (1991) *Micro. Res.,* 41 (1) :5–23.
Baxter, L. T. et al. (1991) *Micro. Res.,* 41(1):5–23.
Bellon, T., (In press, 1993) *Eur. J. Immunol.*
Bevilacqua, M. P., et al. (1987) *Proc. Natl. Acad. Sci. USA,* 84:9238–9242.
Bhattacharya, A., et al. (1981) *J. Immunol.*, 126 (6): 2488–2495.
Bigler, S. A., et al. (1993) *Hum. Pathol.* 24:220–226.
Billington, W. D. et al. (1986) *J. Reprod. Immunol.,* 9:155–160.
Bindon, C. I. (1988) *Eur. J. Immunol.,* 18:1507–1514.
Bittner et al., (1987) *Methods in Enzymol.,* 153: 516–544.
Bjorndahl, et al. (1989) *Eur. J. Immunol.,* 19:881–887.
Bjorntorp, et al. (1983) *J. Lipid Res.,* 24:105–112.
Blakey, D. C., et al. (1987b) *Biochem Biophys ACTA,* 923Y(1) :59–65.
Blakey, D. C., et al. (1987a) *Cancer Res.,* 47:947–952.
Blanchard, D. K., et al. (1988) *Cancer Res.,* 48:6321–6327.
Borden, E. C., et al. (1990) *Cancer,* 65:800–814.
Boyer, C. M., et al. (1989) *Cancer Res.,* 49:2928–2934.
Boyer, C. M., et al. (1989) *Int. J. Cancer,* 43:55–60.
Bühring, H. J., et al. (1991) *Leukemia,* 5:841–847.

Burchell et al., (1983) *J. Immunol.*, 131(1):508–13.
Burrows, F. J., et al. (1993) *Proc. Natl. Acad. Sci.*, 90:8996–9000.
Burrows, F. J., et al. (1992) *Cancer Res.*, 52:5954–5962.
Burrows, F. J., et al. (1991) *Cancer Res.*, 51:4768–4775.
Byers, V. S., et al. (1989) *Cancer Res.*, 49:6153–6160.
Byers, V. S., et al. (1988) *Immunol.*, 65:329–335.
Capobianchi, M. R. (1985) *Hum. Immunol.*, 13:1.
Cheifetz, S. et al. (1992) *J. Biol. Chem.*, 267:19027–19030.
Chen, T. Y., et al. (1990) *J. Immunol.*, 145:8–12.
Cheresh, D. A., (1987) *Proc. Natl. Acad. Sci. USA*, 84:6471–6475.
Cherwinski, H. M. (1987) *J. Exp. Med.*, 166:1229–1244.
Cherwinski et al. (1989).
Chodak, G. W., et al. (1980) *Ann Surg.*, 192:762–771.
Colberre-Garapin et al., (1981), *J. Mol. Biol.*, 150:1.
Colcher et al, (1987) *Cancer Res.*, 47:1185; and 4218.
Collins, T. et al. (1984) *Proc. Natl. Acad. Sci. U.S.A.*, 81:4917–4921.
Cotran, R. S., et al. (1986) *J. Exp. Med.*, 164:661–666.
Daar, A. S., et al. (1984) *Transplantation*, 38(3):293–298.
Darzynkiewicz, Z., et al. (1976) *Proc. Natl. Acad. Sci. USA*, 73:2881–2884.
de Waal, R. M. W. (1983) *Nature*, 303:426–429.
DeFranco, A. L. (1991) *Nature*, 352:754–755.
Demur, C., et al. (1989) *Leuk. Res.*, 13:1047–1054.
Denekamp, J. et al. (1982) *Brit. J. Cancer*, 461:711–720.
Denekamp, J. (1984) *Prog. Appl. Microcirc.*, 4:28–38.
Denekamp, J. (1986) *Cancer Topics*, 6:6–8.
Denekamp, J. (1990) *Cancer Meta. Rev.*, 9:267–282.
Denekamp, J. (1990) *Cancer Netastasus Rev.*, 9:253–266.
Dillman, R. O., et al. (1988) *Antibody, Immunocon. Radiopharm.*, 1:65–77.
Dixon et al., *Mol. & Cell Biol.*, 7:4896–4902, 1989.
Duijvestijn, A. M., et al. (1987) *J. Immunol.*, 138:713–719.
Duijvestijn, A. M., et al. (1986) *Proc. Natl. Acad. Sci. (USA)*, 83: 9114–9118.
Dunham L. C. et al. (1953) *Cancer Inst.*, 13:1299–1377.
Dustin, M. et al. (1986) *J. Immunol.*, 137:245–254.
Dvorak, H. F. et al. (1991) *Cancer Cells*, 3 (3) :77–85.
Enestein, J. et al. (1992) *Exp. Cell. Res.*, 203:499–503.
Engert, A., et al. (1991) *Leuk. Res.*, 15:1079–1086.
Epenetos, A.A., et al. (1986) *Cancer Res.*, 46:3183–3191.
Fernandez-Botran, R. et al. (1991) *FASEB J.*, 5:2567–2574.
Fett, J. W. et al. (1987) *Biochem. Biophys. Res. Comm.*, 146:1122–1131.
Fett, J. W., et al. (1985) *Biochem.*, 24:5480–5486.
Flickinger & Trost, (1976) *Eu. J. Cancer*, 12(2):159–60.
Folkman, J. (1990) *J. Natl. Cancer Inst.*, 82:4–6.
Folkman, J. (1985) *Adv. Cancer Res.*, 43:175–230.
Folkman, J. (1985) In: V. T. DeVita, S. Hellman and S. A. Rosenberg (eds.), *Important Advances in Oncology*, Part I, pp. 42–62, Philadelphia: J. B. Lippincott.
Fox, B. A. et al. (1990) *J. Biol. Resp.*, 9:499–511.
French, J. E., et al. (1963) *Br. J. Exp. Pathol.*, XLV:467–474.
Fujihara, K., (1991) *Nippon Jibiinkoko Gakkai Kaiho*, 94:1304–1314.
Fujimori, K. et al. (1989) *Cancer Res.*, 49:5956–5663.
Fulton, R. J. et al. (1986) *J. Biol. Chem.*, 261:5314–5319.
Garcia, F. U. et al. (1990) *Am. J. Pathol.*, 136:1125–1135.
Garrido, M. A., et al. (1990) *Cancer Res.*, 50:4227–4232.
Gerlach, H., et al. (1989) *J. Exp. Med.*, 170:913–931.
Ghetie, M. A., et al. (1988) *Cancer Res.*, 48:2610–2617.
Ghetie, M. A., et al. (1991) *Cancer Res.*, 51:5876–5880.
Ghose, et al. (1987) *CRC Critical Reviews in Therapeutic Drug Carrier Systems*, 3:262–359.
Ghose, et al. (1983) *Meth. Enzymology*, 93:280–333.
Girling, et al. (1989) *J. Int. J. Cancer*, 43:1072–1076.
Glenhie, M. J., et al. (1987) *J. Immunol.*, 139:2367–2375.
Gomez-Pinilla and Cotman, *Neuroscience*, 49:771–780, 1992.
Gospodarowicz, D. et al. (1981) *J. Cell. Physiol.*, 107(2) :171–183.
Gospodarowicz, D. et al. (1979) *Exp. Eye Res.*, 29(5) :485–509.
Gougos, A. & Letarte, M. (1990) *J. Biol. Chem.*, 265:8361–8364.
Gougos, A. & Letarte, M. (1988) *J. Immunol.*, 141:1925–1933.
Gougos, A. et al. (1992) *Int. Immunol.*, 4:83–92.
Greiner, J. W. et al. (1991) *J. Surg. Oncol. (Suppl.)*, 2:9–13.
Griffin, T. W., et al. (1989) *J. Cancer Immunol. Immunother.*, 29:43–50.
Griffin, T. W., et al. (1988) *Treat. Res.*, 37:433–455.
Groenewegen, G., et al. (1985) *Nature*, 316:361–363.
Gross, J. A., et al. (1990) *J. Immunol.*, 144:3201–3210.
Hagemeier, H. H., et al. (1986) *Int. J. Cancer*, 38:481–488.
Halling et al. (1985) *Nucl. Acids Res.*, 13:8019–8033.
Hammerling, G. J. (1976) *Transplant. Rev.*, 30:64–82.
Harkhess, J. E. (1983) *The Biology and Medicine of Rabbits*, (Lea & Fabinger, Philadelphia).
Herbin and Gross, "Binding sites for bFGF on solid tumors are associated with the vasculature," In Angiogenesis: Key Principles, R-Steiner, P. Weiss & R. Langer, eds. Birkamser Verlag, Basel, Switzerland, 1992.
Hess, A. D., et al. (1991) *Transplantation*, 6:1232–1240.
Hokland, M. et al. (1988) *Cancer Meta. Rev.*, 7:193–207.
Horak, E. R. et al. (1992) *Lancet*, 340:1122–1124.
Imai, Y., et al. (1991) *J. Cell Biol.*, 113:1213–1221.
Inouye et al., (1985), *Nucleic Acids Res.*, 13:3101–3109
Irie, R. F., et al. (1970) *J. Natl. Cancer Inst.*, 45:515–524.
Irie, R. F. (1971) *Cancer Res.*, 31:1682–1689.
Jaffe, E. A. et al. (1973) *J. Clin. Invest.*, 52:2745–2752.
Jain, R. K. (1990) *Cancer Meta. Rev.*, 9(3):253–266.
Jain, R. K. (1988) *Cancer Res.*, 48:2641–2658.
Jones, E. L. et al. (1984) *J. Pathol.*, 144:131–137.
Jones, P. L., et al. (1986) *Cancer Immunol. Immunother.*, 22:139–143.
June, C. H., et al. (1987) *Molecular Cell Biology*, 12:4472–4481.
Juweid, M. et al. (1992) *Cancer Res.*, 52:5144–5153.
Kandel, et al. (1991) *Cell*, 66:1095–1104.
Kaplan, E. H. (1989) *Hematology/Oncology Clinics of North America*, 3:125–135.
Karasek, M. A. (1989) *J. Invest. Derm.*, 93(2, suppl) :335–385.
Kasahara, T., (1983) *J. Immunol.*, 131(5):2379–2385.
Kennel, S. J., et al. (1991) *Cancer Res.*, 51:1.529–1536.
Kim K. J., (1979) *J. Immunol.*, 122(2):549–554.
Kimura, S., et al. (1980) *Immunogenetics*, 11:373–381.
Knowles & Thorpe (1987) *Anal. Biochem.*, 120:440–443.
Kobayashi, M. et al. (1991) *Human Cell*, 4:296–305.
Kohler, G. & Milstein, C. (1975) *Nature*, 256:495–497.
Koulova, L., et al. (1991) *J. Exp. Med.*, 173:759–762.
Lamb et al. (1985) *Eur. Jrnl. Biochem.*, 148:265–270.
Lan, M. S., et al. (1987) *Int. J. Cancer*, 39:68–72, 1987.
Lee, W. T., et al. (1990) *J. Immunol.*, 144:3288–3295.
Li, J-l, et al. (1989) *Cell. Immunol.*, 118:85–89.
Logan et al., (1984), *Proc. Natl. Acad. Sci. USA*, 81:3655–3659.
Lord et al. (1992), *In Genetically Engineered Toxins* (Ed. A. Frank, M. Dekker Publ., p. 183)
Lowder, J. N. et al. (1987) *Blood*, 69:199.210.
Lowe, J., Ling, et al. (1986) *Immunol Lett.*, 12:263–269.

Lowy et al., (1980), *Cell*, 22:817.
Madri, J. A. et al. (1992) *Mol. Reprod. Devel.*, 32:121–126.
Maeda, K. et al. (1991) *J. Invest. Derm.*, 97:183–189.
Mason, D. W. & Williams, A. F. (1980) *Biochem. J.*, 187:1–20.
Matsuzaki et al., *Proc. Natl. Acad. Sci. USA*, 86:9911–9915, 1989.
Mazzocchi, A. et al. (1990) *Cancer Immunol. Immunother.*, 32:13–21.
Metcalf, D. and Nicola, N. A. (1985) In: *Molecular Biology of Tumor Cells* (Wahren, B. et al., Eds) New York: Raven Press, pages 215–232.
Mignatti, P. et al. (1991) *J. Cell. Biol.*, 113:1193–1201.
Miotti et al., (1987) *Int. J. Cancer*, 39:297.
Morrow, K. J. Jr., et al., (1991) Techniques for the production of Monoclonal and Polyclonal Antibodies. In Colloidal Gold: Principles, Methods and Applications, Vol. 3, Ed. Hayatt, pp. 31–57, Academic Press, San Diego, Calif.
Mulligan et al., (1981), *Proc. Natl. Acad. Sci. USA*, 78:2072.
Murray, J. C., et al. (1989) *Radio. Onc.*, 16:221–234.
Murray et al. (1984) *N. Eng. Jrnl. Med.*, 310:883.
Naieum, M. et al. (1982) *J. Immunol. Methods*, 50:145–160.
Natali, P. G., et al. (1981) *Scand. J Immunol.*, 13:541–546.
Nawroth, P., et al. (1988) *J. Exp. Med.*, 168:637–648.
Nevens, J. R. (1992) *J. Chromatography*, 597:247–256.
Nishikawa et al., *Advances in Experimental Medicine and Biology*, 324:131–139, 1992.
Novick, D. et al. (1989) *J. Exp. Med.*, 170:1409–1414.
O'Connell, K. A. et al. (1990) *J. Immunol.*, 144(2):521–525.
O'Connell, P. J. et al. (1992) *Clin. Exp. Immunol.*, 90:154–159.
Ogata et al. (1990) *J. Biol. Chem.*, 256:20678–20685).
O'Hare et al. (1987) *FEBS Left.*, 210:731.
O'Hare et al., (1981), *Proc. Natl. Acad. Sci. USA*, 78:1527.
Oi & Morrison (1986) *Mt. Sinai J. Med.*, 53(3):175–180.
Oi, V. T. et al. (1978) *Curr. Top. Microbiol. Immunol.*, 81:115–120.
Osborn, L. et al. (1989) *Cell*, 59:1203–1211.
Palleroni, A. V., et al. (1991) *Int. J. Cancer*, 49:296–302.
Perez, P., et al. (1985) *Nature*, 316:354–356.
Peri, G. et al. (1990) *J. Immunol.*, 144(4):1444–1448.
Pervez, S., et al. (1988) *Int. J. Cancer*, 3:30–33.
Pietersz, G. A., et al. (1988) *Antibody, Immunoconj. Radiopharm.*, 1:79–103.
Pober, et al. (1983) *J. Exp. Med.*, 157:1339–1353.
Pober, J. S., et al. (1991) *J. Immunol.*, 137:1893–1896.
Pober, J. S., et al. (1987) *J. Immunol.*, 138:3319–3324.
Qian, J. H., et al. (1991) *Cancer Res.*, 140:3250.
Reilly et al., *Biochem. Biophys. Res. Commun.*, 164:736–743, 1989.
Reisfeld et al., (1982) *Melanoma Antigens and Antibodies*, p. 317.
Rettig, W. J. et al. (1992) *Proc. Natl. Acad. Sci. USA*, 89:10832–10836.
Revtyak, G. E. et al. (1988) *American J. of Physiology*, 254:C8–19.
Rice, G. E. et al. (1990) *J. Exp. Med.*, 171:1369–1374.
Rowlinson-Busza, G. et al. (1991) *Cancer Res.*, 51:3251–3256.
Ruco, L. P., et al. (1990) *Am. J Pathol.*, 137(5):1163–1171.
Ruther et al., (1983), EMBO J., 2:1791
Rybak, S. M. et al. (1987) *Biochem. Biophys. Res. Comm.*, 146:1240–1248.
Sambrook et al., (1989) Molecular Cloning, A Laboratory Manual, Cold Spring Harbor Laboratory, N.Y.
Sanchez-Madrid, F. (1983) *J. Immunol.*, 130(1):309–312.
Sands, H. (1988) "*Immunoconjugates and Radiopharmaceuticals*", 1:213–226.
Sands, H. (1988) *Antibody, Immunoconjugates and Radiopharmaceuticals, 1: 213 –226*.
Santerre et al. (1984) *Gene*, 30:147.
Sarma, V. et al. (1992) *J. Immunology*, 148:3302–3312.
Schlingemann, R. O., et al. (1985) *Lab. Invest.*, 52:71–76.
Schutt, C., et al. (1988) *Immunol. Lett.*, 19:321–328.
Seto, M., et al. (1982) *J. Immunol.*, 128:201–205.
Shen, G. L., et al. (1988) *Int. J. Cancer*, 42:792–797.
Shepard et al., (1991) *J. Clin. Immunol.*, 11:117–127.
Shockley, T. R. et al. (1991) *Ann. N.Y. Acad. Sci.*, 617:367–382.
Sillman, F. et al. (1981) *Am. J. Obstet. Gynecol.*, 139:154–159.
Smith et al., (1983), *J. Virol.*, 46:584.
Spertini, O., et al. (1991) *J. Immunol.*, 147:2565–2573.
Spitler, L. E. (1988) *Cancer Treat. Res.*, 37:493–514.
Steel, G. G. (1977) *Growth Kinetics of Tumours*, p.6, Clarendon Press, Oxford, U.K.
Stevenson, F. K. et al. (1990) *Chem. Immunol.*, 48:126–166.
Stoscheck, C. M. and King, L. E. (1986) *Cancer Res.*, 46:1030–1037.
Stout, R. D. & Suttles, J. T. (1992) *Cell. Immunol.*, 141:433–443.
Street, N. et al. (1989) *Cell. Immunol.*, 120:75–81.
Sung, C. et al. (1990) *Cancer Res.*, 7382–7392.
Szybalska et al., (1962), *Proc. Natl. Acad. Sci. USA*, 48:2026.
Takac, L., et al. (1988) *J. Immunol.*, 141:3081–3095.
Tax, W. J. et al. (1984) *Clin. Exp. Immunol.*, 55:427–436.
Tazzari, P. L. et al. (1987) *Clin. & Exp. Immunol.*, 70:192–200.
Thompson, C. B., et al. (1989) *Proc. Natl. Acad. Sci. USA*, 86:1333–1337.
Thor et al., (1987) *Cancer Res.*, 46:3118.
Thorpe et al., (1988) *Cancer Res.*, 48: 6396–6403.
Thorpe, P. E., et al. (1985) *Eur. J. Biochem.*, 147:197–206.
Thorpe, P. E., et al. (1988) *Cancer Res.*, 48:6396–6403.
Thorpe, P. E., et al. (1987) *Cancer Res.*, 47:5924–5931.
Thorpe, P. E., et al. Selective killing of proliferating vascular endothelial cells by an anti-fibronectin receptor immunotoxin, Presented at the 16th LH Gray Conference, University of Manchester Institute of Science and Technology, Sep. 17–21, 1990.
Till, M., et al. (1988) *Cancer Res.*, 48:1119–1123.
Titus, J. A. et al. (1987) *J. Immunol.*, 138:4018–4022. *Tumor Blood Circulation* (1978) CRC Press Inc., Boca Raton.
Tutt, A. et al. (1991) *Eur. J. Immunol.*, 21:1351–1358.
Vaickus, L., et al. (1991) *Cancer Invest.*, 9:195–209.
Van Deurs, B., et al. (1988) *J. Cell Biol.*, 106:253–267.
Van Deurs, B., et al. (1986) *J. Cell Biol.*, 102:37–47.
Van Duk, J. et al. (1989) *Int. J. Cancer*, 43:344–349.
Van Heeke et al., (1989), *J. Biol. Chem.*, 264:5503–5509.
Vitetta, E. S. et al. (1991) *Cancer Res.*, 15:4052–4058.
Vogel & Muller-Eberhard (1981) *Anal. Biochem.*, 118(2):262–268.
Wang, J. M. et al. (1993) *Int. J. Cancer*, 54:363–370.
Watanabe, Y. et al. (1988) *Eur. J. Immunol.*, 18:1627–1630.
Watanabe, Y., et al. (1989) *Proc. Natl. Acad. Sci. USA*, 86:9456–9460.
Weidner, N. et al. (1992) *J. Natl. Cancer Inst.*, 84:1875–1887.
Weiner, L. M., et al. (1989) *Cancer Res.*, 49:4062–4067.
Westphal, J. R. et al. (1993) *J. Invest. Derm.*, 100:27–34.
Wiglet et al., (1980), *Proc. Natl. Acad. Sci. USA*, 77:3567.
Wiglet et al., (1977), *Cell*, 11:223.
Winter, et al. (1991) *Nature*, 349:293–299.
Wu, M., Tang, et al. (1990) *Int. J. Pharm.*, 12:235–239.
Xu et al., *J. Biol. Chem.*, 267:17792–17803, 1992.
Yamaue, H. et al. (1990) *Biotherapy*, 2:247–259.

What is claimed is:

1. A purified antibody that binds to the same epitope as the monoclonal antibody TEC-4 (ATCC xxxxx).

2. The purified antibody of claim 1, which is a monoclonal antibody.

3. The purified antibody of claim 2, which is monoclonal antibody TEC-4 (ATCC xxxxx).

4. The purified antibody of claim 1, in a pharmaceutically acceptable diluent or excipient.

5. The purified antibody of claim 1, wherein the antibody is linked to an anticellular agent capable of killing or suppressing the growth or cell division of endothelial cells.

6. The purified antibody of claim 5, which is a monoclonal antibody.

7. The purified antibody of claim 6, which is monoclonal antibody TEC-4 (ATCC xxxxx).

8. The purified antibody of claim 5, wherein the antibody is linked to a plant-, fungus- or bacteria-derived toxin.

9. The purified antibody of claim 8, wherein the antibody is linked to an A chain toxin, a ribosome inactivating protein, α-sarcin, aspergillin, restrictocin, a ribonuclease, diphtheria toxin or *Pseudomonas* exotoxin.

10. The purified antibody of claim 9, wherein the antibody is linked to an A chain toxin.

11. The purified antibody of claim 10, wherein the antibody is linked to ricin A chain.

12. The purified antibody of claim 11, wherein the antibody is linked to deglycosylated ricin A chain.

13. The purified antibody of claim 5, wherein the antibody is linked to a chemotherapeutic agent, a radioisotope or a cytotoxin.

14. The purified antibody of claim 13, wherein the antibody is linked to asteroid, an antimetabolite, an anthracycline, a vinca alkaloid, an antibiotic, an alkylating agent or an epipodophyllotoxin.

15. The purified antibody of claim 5, in a pharmaceutically acceptable diluent or excipient.

16. A purified antibody that binds to the same epitope as the monoclonal antibody TEC-11 (ATCC yyyyy).

17. The purified antibody of claim 16, which is a monoclonal antibody.

18. The purified antibody of claim 17, which is monoclonal antibody TEC-11 (ATCC yyyyy).

19. The purified antibody of claim 16, in a pharmaceutically acceptable diluent or excipient.

20. The purified antibody of claim 16, wherein the antibody is linked to an anticellular agent capable of killing or suppressing the growth or cell division of endothelial cells.

21. The purified antibody of claim 20, which is a monoclonal antibody.

22. The purified antibody of claim 21, which is monoclonal antibody TEC-11 (ATCC yyyyy).

23. The purified antibody of claim 20, wherein the antibody is linked to a plant-, fungus- or bacteria-derived toxin.

24. The purified antibody of claim 23, wherein the antibody is linked to an A chain toxin, a ribosome inactivating protein, α-sarcin, aspergillin, restrictocin, a ribonuclease, diphtheria toxin or *Pseudomonas* exotoxin.

25. The purified antibody of claim 24, wherein the antibody is linked to an A chain toxin.

26. The purified antibody of claim 25, wherein the antibody is linked to ricin A chain.

27. The purified antibody of claim 26, wherein the antibody is linked to deglycosylated ricin A chain.

28. The purified antibody of claim 20, wherein the antibody is linked to a chemotherapeutic agent, a radioisotope or a cytotoxin.

29. The purified antibody of claim 28, wherein the antibody is linked to asteroid, an antimetabolite, an anthracycline, a vinca alkaloid, an antibiotic, an alkylating agent or an epipodophyllotoxin.

30. The purified antibody of claim 20, in a pharmaceutically acceptable diluent or excipient.

* * * * *

UNITED STATES PATENT AND TRADEMARK OFFICE
CERTIFICATE OF CORRECTION

PATENT NO. : 5,660,827
DATED : August 26, 1997
INVENTOR(S) : Philip E. Thorpe, et al It is certified that error appears in the above-identified patent and that said Letters Patent is hereby corrected as shown below:

column 9, line 18, after "(TEC4 and TEC11" please insert --, deposited March 12, 1997 with the American Type Culture Collection, 12301 Parklawn Drive, Rockville, MD 20852, and given the ATCC Accession numbers ATCC HB-12312 and ATCC HB-12311, respectively-- .
In the Specification at column 9, line 37, after "TEC-11 mAbs" please insert -- (ATCC HB-12312 and ATCC HB-12311, respectively)-- .
In the Specification at column 17, line 49, after "TEC-11" please insert -- (ATCC HB-12312 and ATCC HB-12311, respectively)-- .
In the Specification at column 21, line 3, after "TEC-11" please insert -- (ATCC HB-12312)-- .
In the Specification at column 22, line 6, after "TEC-4 and TEC-11" please insert -- (ATCC HB-12312 and ATCC HB-12311, respectively)-- .

In the Claims:
In claim 1 at column 103, line 58, please delete "(ATCC xxxxx)", and insert therefor --(ATCC HB-12312)-- .
In claim 3 at column 103, line 62, please delete "(ATCC xxxxx)", and insert therefor --(ATCC HB-12312)-- .
In claim 7 at column 104, line 59, please delete "(ATCC xxxxx)", and insert therefor --(ATCC HB-12312)-- .
In claim 16 at column 105, line 15, please delete "(ATCC yyyyy)", and insert therefor --(ATCC HB-12311)-- .

UNITED STATES PATENT AND TRADEMARK OFFICE
CERTIFICATE OF CORRECTION

PATENT NO. : 5,660,827
DATED : August 26, 1997
INVENTOR(S) : Philip E. Thorpe and Francis J. Burrows It is certified that error appears in the above-identified patent and that said Letters Patent is hereby corrected as shown below:

In claim 18 at column 105, line 19, please delete "(ATCC yyyyy)", and insert therefor --(ATCC HB-12311)-- .

Signed and Sealed this

Twenty-third Day of June, 1998

Attest:

BRUCE LEHMAN

Attesting Officer

Commissioner of Patents and Trademarks